US012173024B2

United States Patent
Yin et al.

(10) Patent No.: US 12,173,024 B2
(45) Date of Patent: Dec. 24, 2024

(54) **METHOD FOR SYNTHESIZING O-ANTIGEN SACCHARIDE CHAIN OF *HELICOBACTER PYLORI* SEROTYPE O:6**

(71) Applicants: Jian Yin, Wuxi (CN); Jing Hu, Wuxi (CN); Guangzong Tian, Wuxi (CN)

(72) Inventors: Jian Yin, Wuxi (CN); Jing Hu, Wuxi (CN); Guangzong Tian, Wuxi (CN)

(73) Assignee: Jiangnan University, Wuxi (CN)

( * ) Notice: Subject to any disclaimer, the term of this patent is extended or adjusted under 35 U.S.C. 154(b) by 892 days.

(21) Appl. No.: 17/221,724

(22) Filed: Apr. 2, 2021

(65) Prior Publication Data

US 2021/0309683 A1 Oct. 7, 2021

Related U.S. Application Data

(63) Continuation of application No. PCT/CN2019/091198, filed on Jun. 14, 2019.

(30) Foreign Application Priority Data

Mar. 1, 2019 (CN) .......................... 201910156533.1

(51) Int. Cl.
*C07H 15/04* (2006.01)
*A61K 39/385* (2006.01)
*C07H 1/00* (2006.01)
*C08B 37/00* (2006.01)
*A61K 39/00* (2006.01)

(52) U.S. Cl.
CPC ............ *C07H 15/04* (2013.01); *A61K 39/385* (2013.01); *C07H 1/00* (2013.01); *C08B 37/00* (2013.01); *A61K 2039/6031* (2013.01)

(58) Field of Classification Search
CPC .......... C07H 15/04; C07H 1/00; C07H 15/18; A61K 39/385; A61K 2039/6031; A61K 39/105; C08B 37/00; C08B 37/006; A61P 1/04; A61P 31/04; C07K 2/00
See application file for complete search history.

(56) References Cited

PUBLICATIONS

Gurjar, M. K., & Talukdar, A. Synthesis of terminal disaccharide unit of *Klebsiella pneumoniae* ssp. R20. Tetrahedron, 60(14), 3267-3271. https://doi.org/10.1016/j.tet.2004.02.017 (Year: 2004).*
Mukherjee, C., Liu, L., & Nicola. Regioselective Benzylation of 2-Deoxy-2-aminosugars using Crown Ethers: Application to a Shortened Synthesis of Hyaluronic Acid Oligomers. Advanced Synthesis & Catalysis, 356(10), 2247-2256. https://doi.org/10.1002/adsc. 201400269 (Year: 2014).*
Scott et al. Protection against Experimental Melioidosis with a Synthetic manno-Heptopyranose Hexasaccharide Glycoconjugate. Bioconjugate Chemistry, 27(6), 1435-1446. https://doi.org/10.1021/acs.bioconjchem.5b00525 (Year: 2016).*
Stanetty et al. Convergent Synthesis of 4-O-Phosphorylated I-glycero-d-manno-Heptosyl Lipopolysaccharide Core Oligosaccharides Based on Regioselective Cleavage of a 6,7-O-Tetraisopropyldisiloxane-1,3-diyl Protecting Group. Journal of Organic Chemistry, 79(2), 582-598. https://doi.org/10.1021/jo402312x (Year: 2014).*
G O Aspinall et al. "Lipopolysaccharides of *Helicobacter pylori* serogroups O:3 and O:6—structures of a class of Lipopolysaccharides with reference to the location of oligomeric units of D-glycero-alpha-D-manno-heptose residues" Eur J Biochem. 1997. 248(2):592-601.

* cited by examiner

*Primary Examiner* — Yih-Horng Shiao
*Assistant Examiner* — Hoi Yan Nmn Lee
(74) *Attorney, Agent, or Firm* — Lili Chen

(57) ABSTRACT

Disclosed is a method for synthesizing an O-antigen saccharide chain of *Helicobacter pylori* serotype O:6 using seven glycosylation building blocks. Inexpensive and easily available D-glucosamine, D-galactose, D-mannose and L-fucose are used as starting materials, and seven glycosylation building blocks are obtained through a series of chemical reactions. The saccharide building blocks are then selectively linked together to produce O-antigen oligosaccharide chains of *Helicobacter pylori* serotype O:6 with different saccharide configuration through a series of glycosylation reactions. Also disclosed is a method to assemble an amino linker at the reducing end of the O-antigen saccharide chain of *Helicobacter pylori* serotype O:6, and the synthesized oligosaccharide chain with an amino linker can be coupled to a carrier molecule or immobilized on a matrix.

10 Claims, 16 Drawing Sheets

METHOD FOR SYNTHESIZING O-ANTIGEN SACCHARIDE CHAIN OF *HELICOBACTER PYLORI* SEROTYPE O:6

CROSS-REFERENCE TO RELATED APPLICATIONS

This application is a continuation of international application PCT/CN2019/091198, filed Jun. 14, 2019, which claims the benefit of priority to Chinese patent application No. 2019101565331, filed Mar. 1, 2019, the content of which is hereby incorporated by reference in its entirety.

BACKGROUND OF THE INVENTION

Field of the Invention

The invention belongs to the field of carbohydrate chemistry, and it specifically relates to a method for synthesizing an O-antigen saccharide chain of *Helicobacter pylori* serotype O:6.

Description of the Related Art

Since Warren Marshall first isolated *Helicobacter pylori* (Hp) from the stomach of patients with gastritis in 1983, after extensive and in-depth research, scholars from various countries have found that Hp is closely related to the onset of chronic active gastritis, gastroduodenal ulcer, gastric mucosa associated lymphoid tissue (MALT) and gastric cancer. In 1994, the International Cancer Research Center classified Hp as a Class I carcinogen. As a kind of Gram-negative bacteria, Hp is a group of prokaryotic microorganisms that are slender, flexible, and curved in a spiral shape, and can move freely. Hp has the characteristics between bacteria and protozoa, and is mainly located in the deep layer of human gastric mucosa, gastric mucosal epithelial cells, mostly in gastric pits, epithelial folds and glandular cavities. About 50% of the world's population are infected with *Helicobacter pylori*. As high as 70% of the infected people in the world are in developing countries, while only 20%-30% of the infected population live in developed countries. Children are susceptible to *Helicobacter pylori* infection. Children's infections in developing countries are mainly caused by low socioeconomic status and outdated medical and health facility. Improving personal hygiene habits has an important impact on the spread of Hp.

The current anti-Hp infection treatment program is triple or quadruple therapy with bismuth or proton pump inhibitor combined with antibiotics. However, these antibiotic-based treatments have many disadvantages, including development of drug resistance due to long-term use, the risk of repeated infections and high cost of antibiotic treatment. Therefore, there is an urgent need for new methods to prevent and eradicate *Helicobacter pylori* infection. Studies have shown that Hp vaccines may become the most effective method to control this global infection. At present, research on Hp vaccine formulations is mainly based on protein components, while the vaccine research on other components such as polysaccharides is relatively rare. Studies have shown that the development of saccharide vaccines against Hp infection is a very plausible option, and polysaccharide-based conjugate vaccines have been successfully used to prevent systemic infection and inhibit host colonization. The current research on enteric pathogens is based on the investigation of its surface lipopolysaccharide (LPS), which can be used as a candidate vaccine for humans. LPS is the main antigen component on the surface of *Helicobacter pylori* cells. Structural identification studies show that LPS is composed of O-chain polysaccharide, core structure and lipid A. The structure of LPS is as follows:

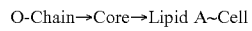

O-Chain→Core→Lipid A~Cell

In the early research of Hp, Penner and his colleagues developed a serotype system based on the difference in the antigenicity of LPS molecules, and defined six different serotypes (O:1-O:6) based on the structural difference of O-chain polysaccharides. Research by Mario and his colleagues proved that the polyvalent Hp lipopolysaccharide-based glycoconjugates induced immunity in mice and produced antibodies that can recognize other serotypes of Hp. The serotype O:6 is one of the Hp serotypes, and is composed of a non-reducing Lewis O-chain linked to heptose. The specific structure is as follows:

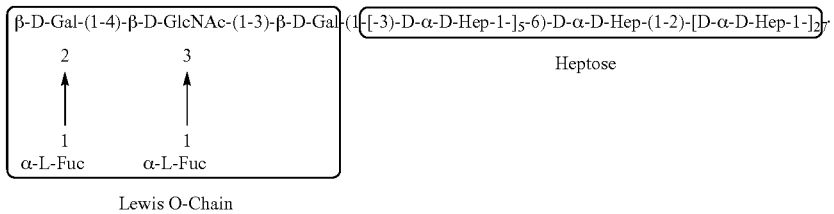

Lewis O-Chain

At present, the research on the lipopolysaccharide of *Helicobacter pylori* is carried out by extraction from inactivated bacteria. The disadvantage of this method is that there are very few products obtained from an extraction. In addition, due to the characteristics of bacterial gene expression and modification, the structure of the extracted lipopolysaccharide is not uniformed with many similar but different structures, which leads to poor experimental repeatability and variable research results. As O-antigen oligosaccharides of Hp serotype O:6 have so far not been chemically synthesized, we developed a method to synthesize an antigen of *Helicobacter pylori* serotype O:6 for use in immunological research. However, in the complex chemical synthesis process of saccharides, the construction of glycosidic bonds is the most basic and also the most difficult and critical issue in saccharide synthesis. Due to the diversity of structures of saccharide compounds and the complexity of stereochemistry, the methodology of saccharide synthesis is still immature and imperfect, and is considered to be the only field of organic chemistry in which there are many methods (dozens of them), but none of them has universal applicability. Because of complex structures of saccharide modules and low selectivity of cis-glycosidic bonds, it is difficult to construct a saccharide with correct stereochemical structure, which limits the research on the chemical synthesis method of O-antigen oligosaccharides of Hp serotype O:6.

SUMMARY OF THE INVENTION

The disclosed is a method for synthesizing an O-antigen saccharide chain fragment of *Helicobacter pylori* serotype O:6. The method uses seven saccharide building blocks to construct the O-antigen saccharide chain fragment of *Helicobacter pylori* serotype O:6, and the seven saccharide building blocks are compounds represented by formulas 1-7, respectively:

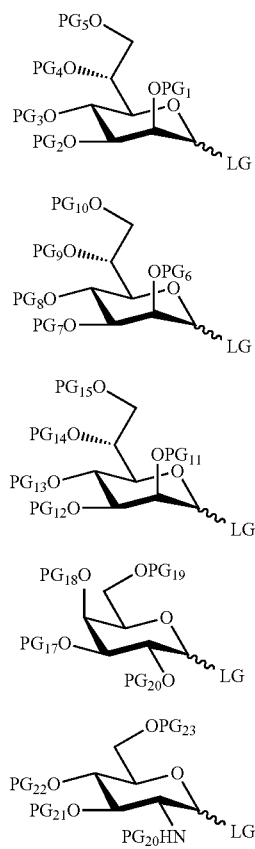

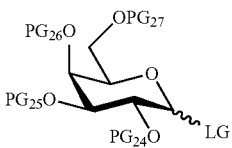

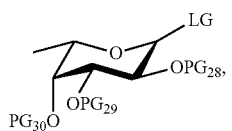

wherein $PG_1$, $PG_2$, $PG_3$, $PG_4$, $PG_5$, $PG_6$, $PG_7$, $PG_8$, $PG_9$, $PG_{10}$, $PG_{11}$, $PG_{12}$, $PG_{13}$, $PG_{14}$, $PG_{15}$, $PG_{17}$, $PG_{18}$, $PG_{19}$, $PG_{21}$, $PG_{22}$, $PG_{23}$, $PG_{25}$, $PG_{26}$, $PG_{27}$, $PG_{28}$, $PG_{29}$ and $PG_{30}$ are independently selected from any one of hydrogen, acyl, 2-naphthylmethyl and its derivatives, benzyl and its derivatives, allyl and silyl; $PG_{16}$ and $PG_{24}$ are independently selected from any one of hydrogen, acyl, alkoxycarbonyl and alkoxycarbonyl (acyl); $PG_{20}$ is selected from any one of alkanoyl, diformyl, carbobenzyloxy and its derivatives; and the leaving groups LG in the structures of formulas 1-7 are independently selected from any one of halogen, iminoester group, thio group and phosphonic acid group.

In one embodiment of the invention, $PG_1$, $PG_2$, $PG_3$, $PG_4$, $PG_5$, $PG_6$, $PG_7$, $PG_8$, $PG_9$, $PG_{10}$, $PG_{11}$, $PG_{12}$, $PG_{13}$, $PG_{14}$, $PG_{15}$, $PG_{18}$, $PG_{19}$, $PG_{21}$, $PG_{23}$, $PG_{25}$, $PG_{26}$, $PG_{27}$, $PG_{28}$, $PG_{29}$ and $PG_{30}$ are independently selected from any one of hydrogen, acyl, 2-naphthylmethyl, benzyl, allyl, allyloxycarbonyl, p-methoxybenzyl and silyl; $PG_{17}$ and $PG_{22}$ are hydrogen; $PG_{16}$ and $PG_{24}$ are independently selected from any one of hydrogen, acyl, alkoxycarbonyl, 9-fluorenylmethoxycarbonyl, and allyloxycarbonyl; and $PG_{20}$ is selected from any one of alkanoyl, trichloroacetyl, phthaloyl, and carbobenzyloxy.

In one embodiment of the invention, the structure of the O-antigen saccharide chain fragment of *Helicobacter pylori* serotype O:6 is shown in formula 28:

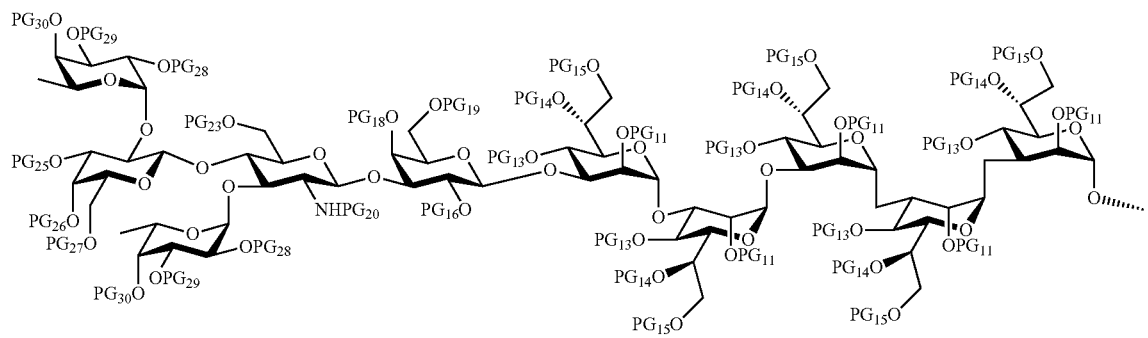

Formula 28

-continued

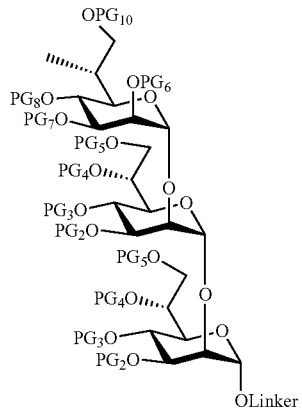

wherein all protecting groups have the same definition as above; the linker is an amino linker —$(CH_2)_n$—N—$Y_1Y_2$; n represents that the linker can have different carbon chain lengths, n=2–40; $Y_1$ and $Y_2$ are protecting groups for amino groups, wherein $Y_1$ is H or benzyl (Bn), and $Y_2$ is H or Cbz.

In one embodiment of the invention, the $PG_1$, $PG_9$, $PG_{12}$, $PG_{17}$, $PG_{21}$, $PG_{22}$ and $PG_{24}$ are temporary protecting groups for hydroxyl, selected from any one of hydrogen (H), acetyl (Ac), benzoyl (Bz), pivaloyl (Piv), chloroacetyl (ClAc), levulinyl (Lev), 9-fluorenylmethoxycarbonyl (Fmoc), allyloxycarbonyl (Alloc), 2-naphthylmethyl (Nap), p-methoxybenzyl (pMBn) or allyl (All).

In one embodiment of the invention, the $PG_2$, $PG_3$, $PG_4$, $PG_6$, $PG_7$, $PG_8$, $PG_{11}$, $PG_{13}$, $PG_{14}$, $PG_{18}$, $PG_{25}$, $PG_{26}$, $PG_{29}$ and $PG_{30}$ are selected from any one of hydrogen (H), acetyl (Ac), benzoyl (Bz), pivaloyl (Piv), chloroacetyl (ClAc), allyloxycarbonyl (Alloc), benzyl (Bn), 2-naphthylmethyl (Nap), p-methoxybenzyl (pMBn) or allyl (All).

In one embodiment of the invention, the $PG_{16}$ and $PG_{24}$ are selected from any one of hydrogen (H), acetyl (Ac), benzoyl (Bz), pivaloyl (Piv), chloroacetyl (ClAc), levulinyl (Lev), 9-fluorenylmethoxycarbonyl (Fmoc), and allyloxycarbonyl (Alloc).

In one embodiment of the invention, the $PG_5$, $PG_{10}$, $PG_{15}$, $PG_{19}$, $PG_{23}$, $PG_{27}$ and $PG_{28}$ are selected from any one of hydrogen (H), acetyl (Ac), benzoyl (Bz), pivaloyl (Piv), chloroacetyl (ClAc), allyloxycarbonyl (Alloc), benzyl (Bn), 2-naphthylmethyl (Nap), p-methoxybenzyl (pMBn), allyl (All), tert-butyldimethylsilyl, tert-butyldiphenylsilyl and triethylsilyl.

In one embodiment of the invention, the $PG_{20}$ is an amino protecting group, selected from any one of trichloroacetyl (TCA), trichloroethoxycarbonyl (Troc), phthaloyl (Phth), and carbobenzyloxy (Cbz).

In one embodiment of the invention, the LG is a leaving group for glycosylation reaction, selected from any one of fluoro (F), chloro (Cl), bromo (Br), iodo (I), trichloroacetimidate ($CCl_3C(=NH)O$—), N-phenyl trifluoroacetimidate glycoside ($CF_3C(=NPh)O$—), ethylthio (SEt), phenylthio (SPh), p-tolylthio (STol), and dibutylphosphonic acid group (—P(=O)—$(OBu)_2$).

In one embodiment of the invention, the method includes the following steps: disaccharide is pre-synthesized, and then O-antigen saccharide chain fragments of *Helicobacter pylori* serotype O:6 are synthesized through the construction of glycosidic bonds.

In one embodiment of the invention, the glycosidic bond is constructed by coupling a glycosyl donor and a receptor with an activating agent to make the D-α-D-Hep-(1-2) linkage.

In one embodiment of the invention, the activating agent includes one or more of NIS (N-Iodosuccinimide), NBS (N-Bromosuccinimide), DBU (1,8-Diazabicyclo[5.4.0]undec-7-ene), and TMSOTf (Trimethylsilyl trifluoromethanesulfonate).

In one embodiment of the invention, the activating agent is preferably a mixture of NIS and TMSOTf.

In one embodiment of the invention, the method includes synthesis of a disaccharide compound, and the synthetic route of making the disaccharide compound is as follows:

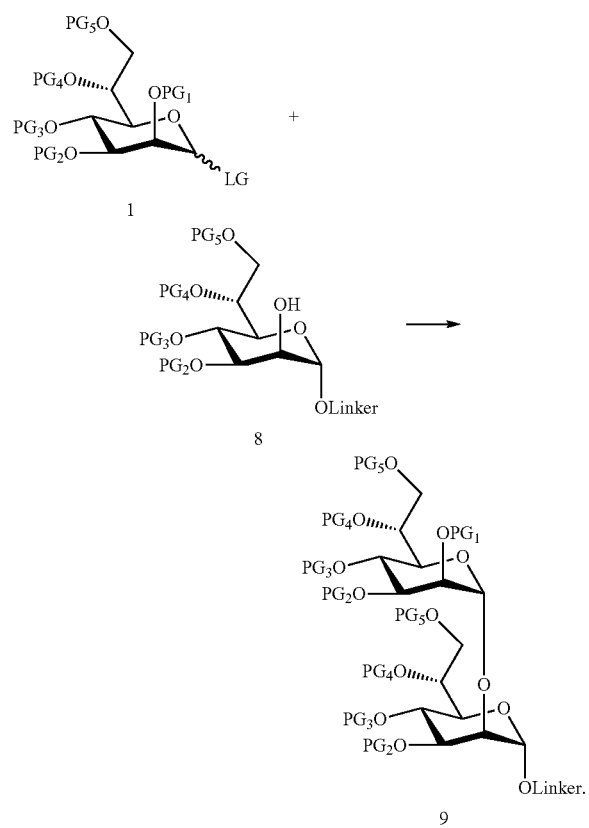

In one embodiment of the invention, the disaccharide is a D-α-D-Hep-(1-2) linked disaccharide compound (compound 9) obtained by coupling the saccharide building block 1 as a glycosyl donor and the saccharide building block 8 as a glycosyl receptor in an organic solvent.

In one embodiment of the invention, the molar ratio of the saccharide building block 1 to the saccharide building block 8 is (1-2):1.

In one embodiment of the invention, the organic solvent is selected from one or more of dichloromethane, tetrahydrofuran, chloroform, and acetonitrile.

In one embodiment of the invention, the organic solvent is preferably dichloromethane.

In one embodiment of the invention, the method for synthesizing the disaccharide includes the following steps: the saccharide building block 1 and the saccharide building block 8 are dissolved in an organic solvent according to the molar ratio, acid-washed molecular sieves are added, and the saccharide building block 1 and the saccharide building block 8 are catalyzed by a Lewis acid and reacted under stirring at −10° C. for 2-4 hours to prepare the D-α-D-Hep-(1-2) linked disaccharide compound 9.

In one embodiment of the invention, the method further includes synthesis of a trisaccharide compound, and the synthetic route of making the trisaccharide compound is as follows:

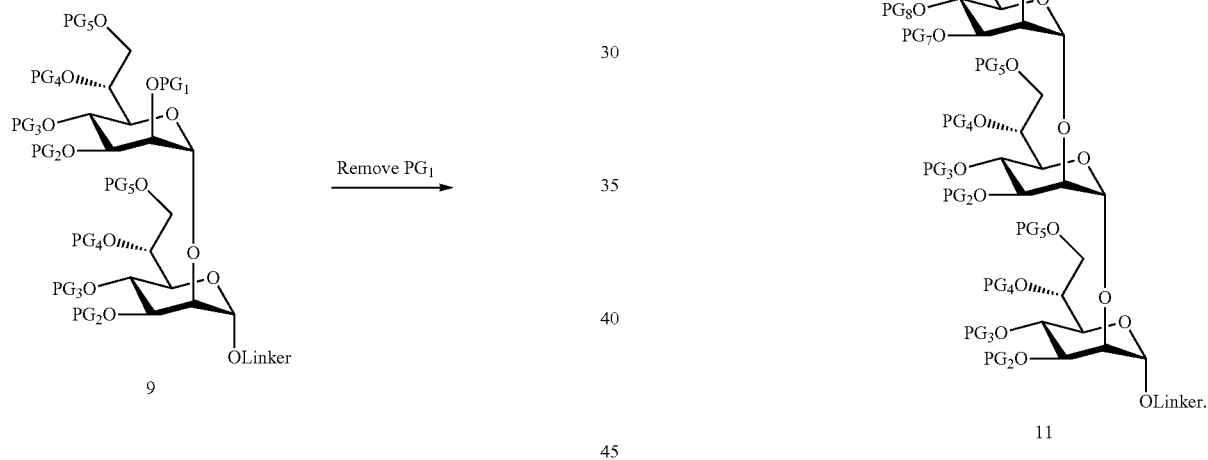

In one embodiment of the invention, the disaccharide compound 9 is deprotected to obtain a glycosyl receptor disaccharide compound 10, and then the compound 2 is used as a glycosyl donor to be coupled with compound 10 to obtain a D-α-D-Hep-(1-2) linked trisaccharide compound 11.

In one embodiment of the invention, the molar ratio of the disaccharide compound 10 to the compound 2 is 1:(1-2).

In one embodiment of the invention, the method for preparing the trisaccharide compound 11 includes the following steps: the disaccharide compound 9 selectively removes a 2-position protecting group of the disaccharide 9 to obtain a glycosyl receptor 10, and then, the glycosyl donor 2 and the glycosyl receptor 10 are catalyzed by Lewis acid according to the molar ratio and reacted under stirring at −10° C. to obtain a D-α-D-Hep-(1-2) linked target trisaccharide compound 11.

In one embodiment of the invention, the method further includes synthesis of a tetrasaccharide compound, and the synthetic route of the tetrasaccharide compound is as follows:

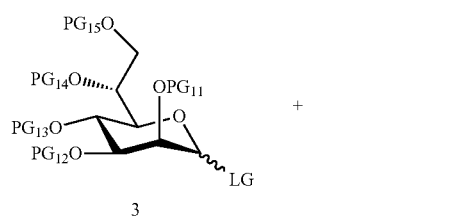

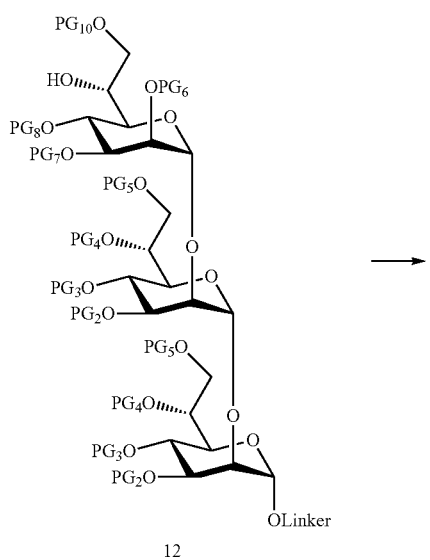

In one embodiment of the invention, the saccharide building block 3 as a glycosyl donor and the trisaccharide compound 12 as a glycosyl receptor are coupled in an organic solvent to obtain the tetrasaccharide compound 13.

In one embodiment of the invention, the molar ratio of the saccharide building block 3 to the trisaccharide compound 12 is (1-2):1.

In one embodiment of the invention, the organic solvent is dichloromethane.

In one embodiment of the invention, the synthesis method of the tetrasaccharide compound 13 includes the following steps: the saccharide building block 3 and the trisaccharide compound 12 are dissolved in dry dichloromethane according to the molar ratio, acid-washed molecular sieves are added, and then the saccharide building block 3 and the trisaccharide compound 12 are catalyzed by Lewis acid and reacted under stirring at −10° C. for 2-4 hours to prepare the target tetrasaccharide compound 13.

In one embodiment of the invention, the method further includes synthesis of a pentasaccharide compound, and the synthetic route of the pentasaccharide compound is as follows:

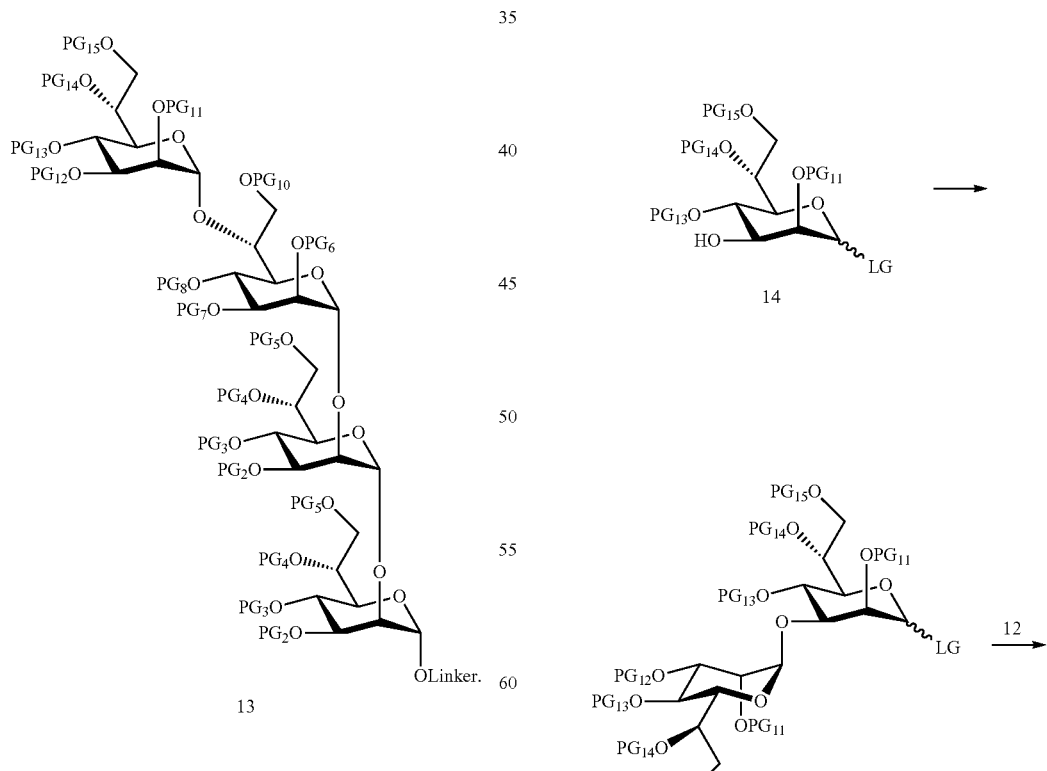

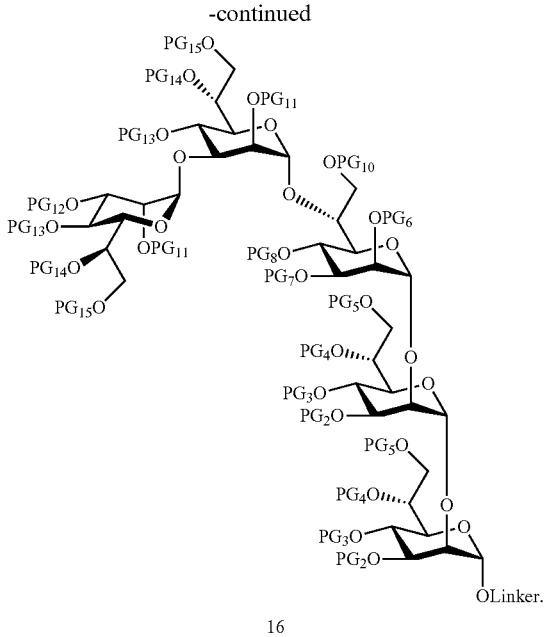

16

In one embodiment of the invention, the saccharide building block 3 as a glycosyl donor and the trisaccharide compound 14 as a glycosyl receptor are coupled in an organic solvent to obtain the tetrasaccharide compound 15; and then the tetrasaccharide compound 15 as a glycosyl donor and the trisaccharide compound 12 as a glycosyl receptor are coupled in an organic solvent to obtain the pentasaccharide compound 16.

In one embodiment of the invention, the preparation method of the pentasaccharide compound 16 includes the following steps: according to the molar ratio of (1-2):1, the saccharide building block 3 and the saccharide building block 14 are dissolved in an organic solvent, molecular sieves and Lewis acid are added, and the reaction is performed at −10° C. for 2-4 hours to obtain a disaccharide donor 15; and then, the disaccharide donor 15 is coupled with 1-2 times molar equivalent of trisaccharide compound 12 to obtain the pentasaccharide compound 16.

In one embodiment of the invention, the method further includes synthesis of an octasaccharide compound, and the synthetic route of the octasaccharide compound is as follows:

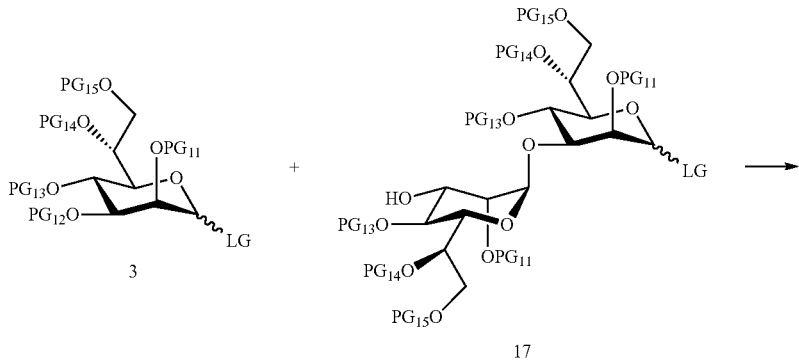

17

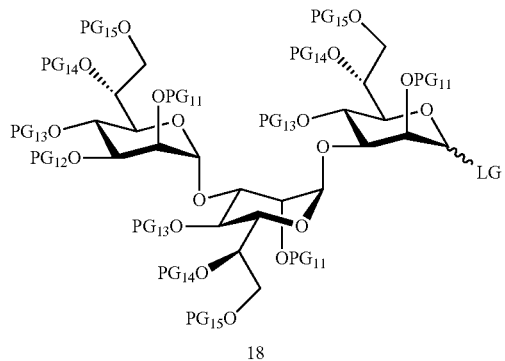

18

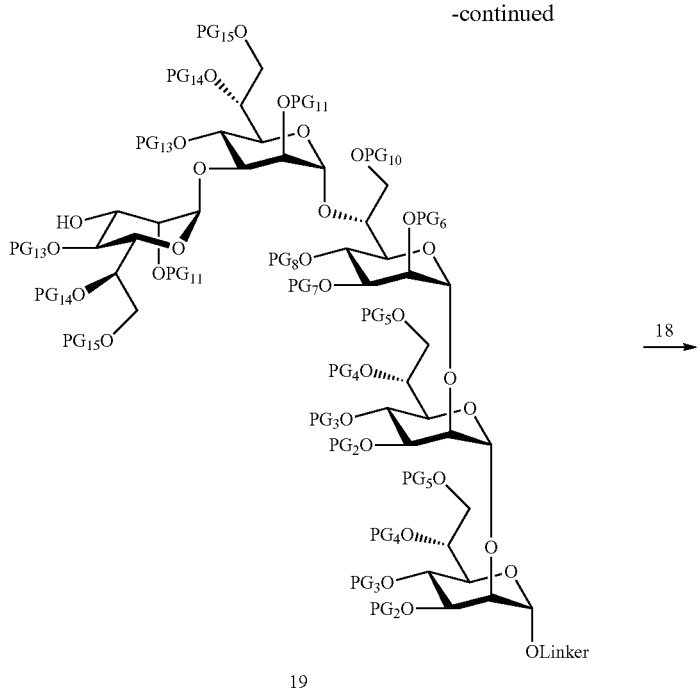

19

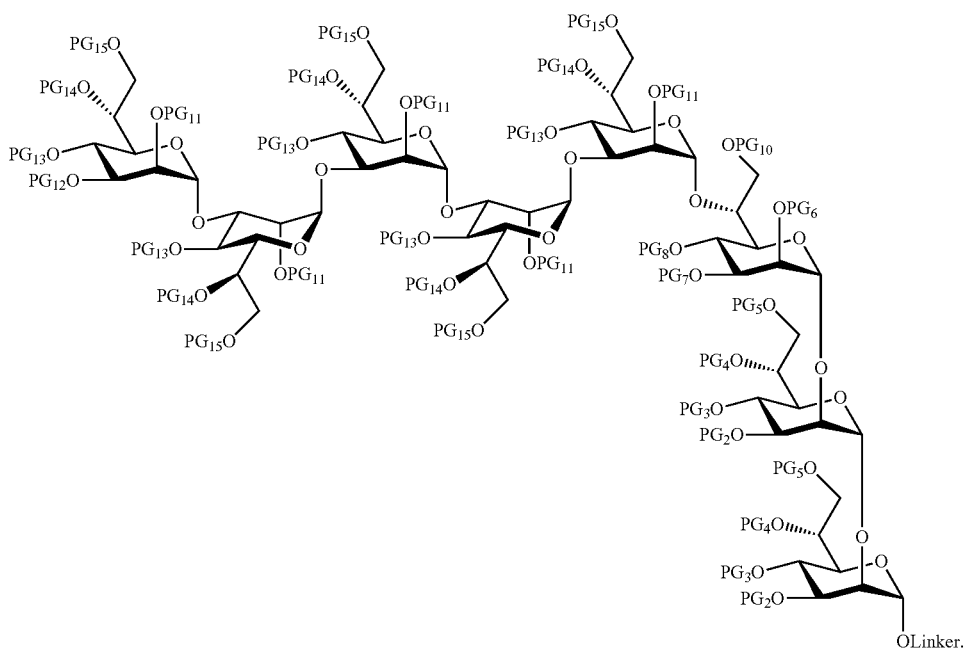

20

In one embodiment of the invention, the saccharide building block 3 as the glycosyl donor and the disaccharide compound 17 as the glycosyl receptor are coupled in an organic solvent to obtain the trisaccharide compound 18; and then, the trisaccharide compound 18 as the glycosyl donor and the pentasaccharide compound 19 as the glycosyl receptor are coupled in an organic solvent to obtain the octasaccharide compound 20.

In one embodiment of the invention, the preparation method of the octasaccharide compound 20 specifically includes the following steps: the saccharide building block 3 and the disaccharide compound 17 are dissolved in an organic solvent at the molar ratio of (1-2):1 (the building block 3: the compound 17), molecular sieves and Lewis acid are added, and the reaction is performed at −10° C. for 2-4 hours to obtain a trisaccharide donor 18; and then, the trisaccharide donor 18 is coupled with 1-2 times molar equivalent of pentasaccharide compound 19 to obtain the octasaccharide compound 20.

In one embodiment of the invention, the method further includes synthesis of a tridecasaccharide compound, and the synthetic route of the tridecasaccharide compound is as follows:

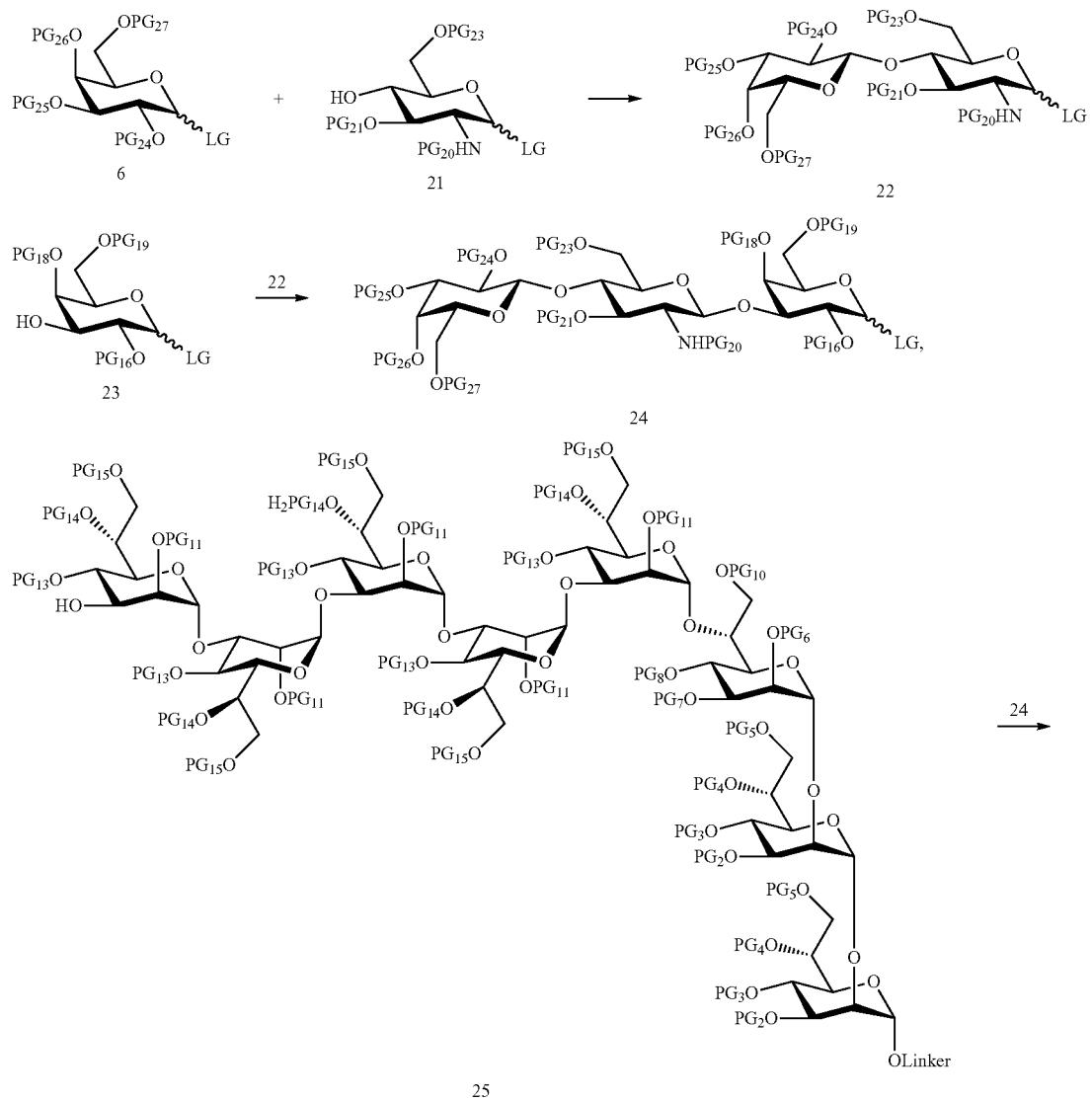
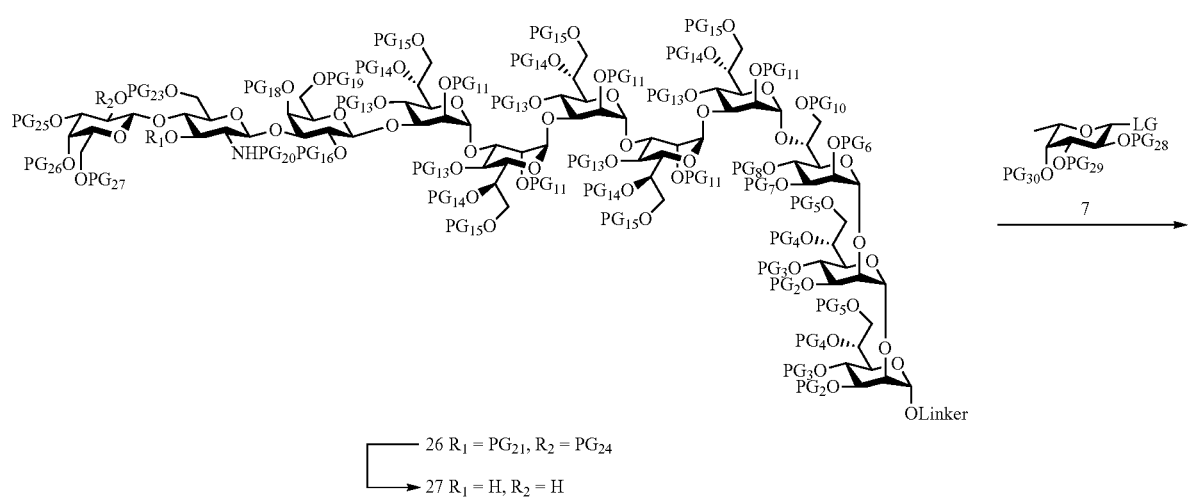
26 $R_1 = PG_{21}$, $R_2 = PG_{24}$
27 $R_1 = H$, $R_2 = H$

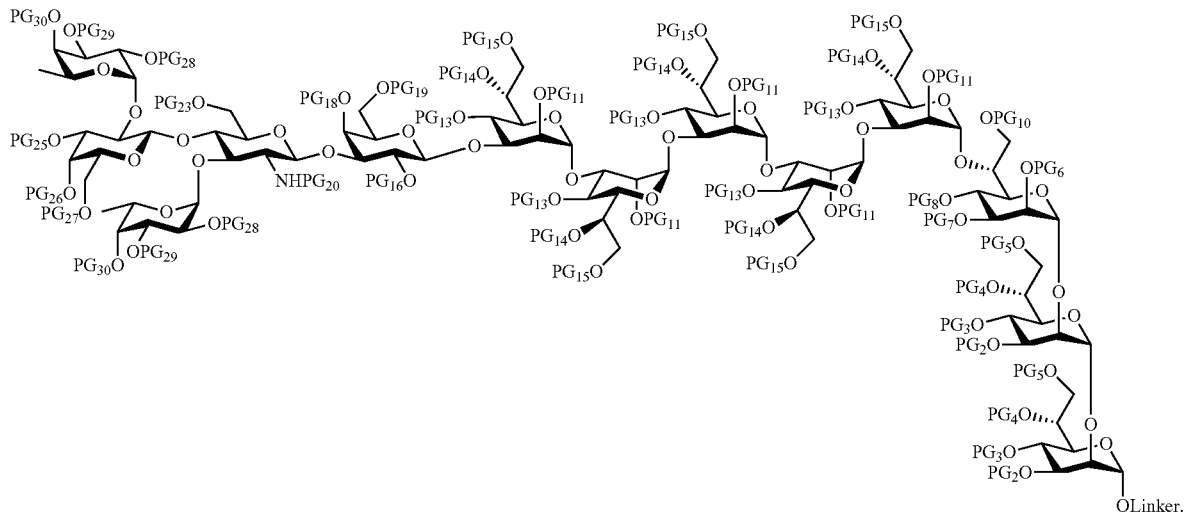

28

In one embodiment of the invention, the synthesis method of the tridecasaccharide compound includes the following steps: (1) the saccharide building block 6 as a glycosyl donor and the saccharide building block 21 as a glycosyl receptor are coupled in an organic solvent to obtain a disaccharide donor 22; and then the disaccharide donor 22 is coupled with the glycosyl receptor 23 to obtain a trisaccharide fragment 24; and (2) the trisaccharide fragment 24 as a glycosyl donor and a glycosyl receptor 25 are catalyzed by Lewis acid and coupled under stirring at −10° C. to obtain an undecasaccharide fragment 26, and protecting groups $PG_{21}$ and $PG_{24}$ are selectively removed to obtain a glycosyl receptor 27; and then the glycosyl receptor 27 and the saccharide building block 7 as a glycosyl donor are coupled to prepare the tridecasaccharide compound 28.

In one embodiment of the invention, the preparation method of the tridecasaccharide compound 28 includes the following steps: (1) 1.5 moles of saccharide building block 6 is used as a glycosyl donor, 1 mole of saccharide building block 21 is used as a glycosyl receptor, the glycosyl donor and the glycosyl receptor are dissolved in dry dichloromethane, acid-washed 4 Å molecular sieves are added, and then the glycosyl donor and the glycosyl receptor are catalyzed by Lewis acid and coupled under stirring at 0° C. for 2-4 hours to prepare the disaccharide donor 22; the glycosyl donor 22 and the glycosyl receptor 23 of an equal molar ratio are catalyzed by Lewis acid and coupled under stirring at −20° C. to obtain the trisaccharide fragment 24; and (2) then the glycosyl donor 24 and the glycosyl receptor 25 of an equal molar ratio are catalyzed by Lewis acid and coupled under stirring at −10° C. to obtain the undecasaccharide fragment 26, two temporary protecting groups $PG_{21}$ and $PG_{24}$ are selectively removed to obtain the glycosyl receptor 27; 4 moles of saccharide building block 7 is used as a glycosyl donor, 1 mole of undecasaccharide 27 is used as a glycosyl receptor, the glycosyl donor and the glycosyl receptor are dissolved in dry dichloromethane/ether (1:1), acid washed 4 Å molecular sieves are added, and then the glycosyl donor and the glycosyl receptor are catalyzed by Lewis acid and coupled under stirring at −40° C. for 2-4 hours to prepare the target tridecasaccharide 28.

The disclosure further discloses an O-antigen oligosaccharide compound of *Helicobacter pylori* serotype O:6 assembled with a linker and synthesized by the above method, and the structure of the compound is shown in formula I:

Formula I

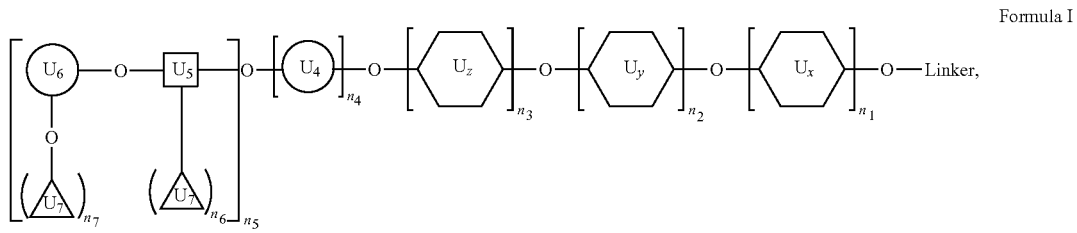

wherein x is 1, 2 or 3; y is 1, 2 or 3; z is 1, 2 or 3; $n_1$, $n_2$, $n_3$, $n_4$ and $n_5$ are integers in a range of 0-5, wherein $n_1$, $n_2$ and $n_3$ are not zero at the same time; $n_6$ and $n_7$ are 0 or 1;

wherein the structural formulas of $U_1$, $U_2$, $U_3$, $U_4$, $U_5$, $U_6$, and $U_7$ are as follows:

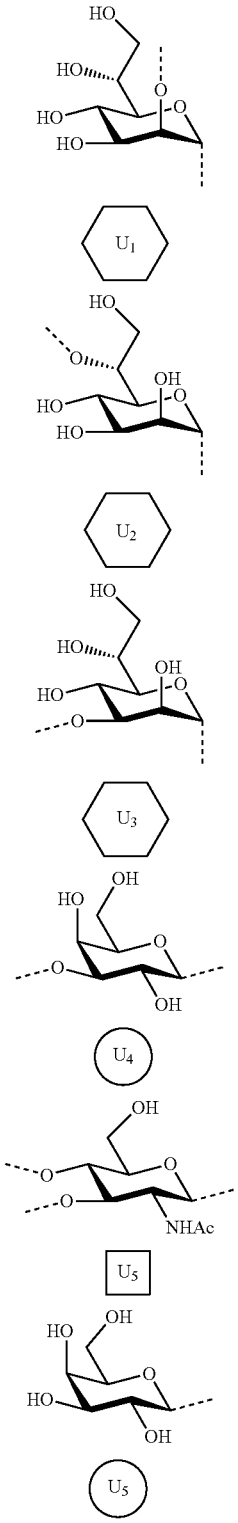

-continued

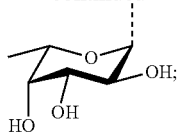

the linker includes an amino linker [—$(CH_2)_n$—N—$Y_1Y_2$]; n represents that the linker can have different carbon chain lengths, n=2-40; $Y_1$ and $Y_2$ are protecting groups for amino groups, wherein $Y_1$ is H or benzyl (Bn), and $Y_2$ is H or carbobenzyloxy (Cbz).

In one embodiment of the invention, the linker can be fully or partially substituted with fluoro.

In one embodiment of the invention, the linker may contain a three-, four-, five- or six-membered saturated carbocyclic ring; a five-membered unsaturated carbocyclic ring (non-aromatic ring); a four-, five-, or six-membered saturated oxygen heterocyclic ring; a four-, five-, or six-membered saturated nitrogen heterocyclic ring; or a six-membered aromatic carbocyclic ring.

In one embodiment of the invention, the linker may also contain an amide bond and/or a carbamido group.

In one embodiment of the invention, the linker may contain one or more substituent groups, and these substituent groups may include: —F, —Cl, —$CH_3$, —$C_2H_5$, —$C_3H_7$, —$C_5H_9$, —$C_6H_{13}$, —$OCH_3$, —$OC_2H_5$, —$CH_2F$, —$CHF_2$, —$CF_3$, —C(O)—$NH_2$, —$SCH_3$, —$SC_2H_5$, —NHC(O)$CH_3$, —N$(CH_3)_2$ and —N$(C_2H_5)_2$.

In one embodiment of the invention, it provides a preparation method of a saccharide-protein conjugate, wherein it uses the above O-antigen oligosaccharide compound of *Helicobacter pylori* serotype O:6 with the linker to make the saccharide-protein conjugate.

In one embodiment of the invention, it provides an application of the O-antigen oligosaccharide compound of *Helicobacter pylori* serotype O:6 assembled with the linker in the development or preparation of *Helicobacter pylori* vaccines or drugs for preventing or treating diseases caused by *Helicobacter pylori* infection.

In the embodiment of the invention, it uses simple and easy-to-obtain glucosamine, galactose, mannose and fucose as starting materials to obtain seven saccharide building blocks through a series of chemical reactions. Then under the action of corresponding activating reagents, based on the neighboring group participation effect, solvent effect, additive effect and other design, after a series of glycosylation reactions, the saccharide building blocks are coupled to obtain an O-antigen saccharide chain of *Helicobacter pylori* serotype O:6. In addition, the reducing end has a linker with an amino group that can be used to link with protein to prepare a glycoconjugate vaccine in the future.

The method of the invention has simple steps, and is time-saving, labor-saving and cost-efficient. It can produce O-antigen disaccharide, trisaccharide, pentasaccharide, octasaccharide and tridecasaccharide of *Helicobacter pylori* serotype O:6 through chemical synthesis. It provides a synthetic route for selectively constructing the linkage of each saccharide building block through the protecting group strategy, temperature effect, solvent effect and additive effect, and the method can be applied to the synthesis of the O-antigen disaccharide, trisaccharide, pentasaccharide, octasaccharide, and tridecasaccharide of *Helicobacter pylori* serotype O:6. The reducing ends of the synthesized O-antigen saccharide chain fragments of *Helicobacter pylori* serotype O:6 are all assembled with amino linkers, and the amino linkers can be used for preparing glycoconjugates with carrier proteins. The glycoconjugates can be used for immunological research, and play an important role in the development of prevention and treatment of *Helicobacter pylori*.

DETAILED DESCRIPTION

Specific embodiments of the invented method are further described in detail with regard to the drawings and the Examples. The specific embodiments are presented here for illustrative purposes only, and are not meant to limit the scope of the invention which is defined by the claims as presented. Various changes and modifications to the disclosed methods known to those skilled in the art shall be covered within the scope of protection.

If no specific conditions are specified in the examples, they are carried out according to the general conditions or the conditions recommended by the manufacturer. Any reagents or instruments of which no manufacturers are indicated are commercially available conventional products.

All reagents are analytically pure unless otherwise specified, and have not been further purified unless otherwise specified. All solvents are dried and redistilled by standard methods before use. Unless otherwise noted, all reactions are carried out under the protection of inert gas in dried glassware under magnetic stirring. A silica gel thin plate used for thin layer chromatography (TLC) is of model GF254, produced by Qingdao Haiyang Chemical Co., Ltd. The TLC plate is dyed by ultraviolet light (UV) and a Hanessian solution (cerium sulfate and ammonium molybdate dissolved in a sulfuric acid solution) or a 5% sulfuric acid-ethanol solution, and can be visually detected. Column chromatography silica gel is produced by Qingdao Haiyang Chemical Co., Ltd. (Qingdao, China), and the column chromatography silica gel is of 300-400 meshes. The 1H NMR, 13C NMR, 1H-13C HSQC and 1H-1H COSY spectrograms are measured by NVANCE III 400-MHz, 600-MHz and 700-MHz NMR spectrometers. Unless otherwise specified, $CDCl_3$ is used as the solvent, TMS (Tetramethylsilane) is used as the internal standard, and the measurement is performed at ambient temperature. Peak type expression methods include: singlet (s), broad singlet (br s), doublet (d), quartet (dd), triplet (t), and multiplet (m). All NMR chemical shifts (δ) are recorded in ppm, and the coupling constant (J) is recorded in Hz. A mass spectrum is measured by a Thermo Scientific TSQ Quantum Ultra instrument (Waltham, MA, USA), and a high resolution mass spectrum is measured by an IonSpec Ultra instrument (Varian, Palo Alto, California, U.S).

Example 1. Synthesis of Saccharide Building Block 8*

Figure 1:
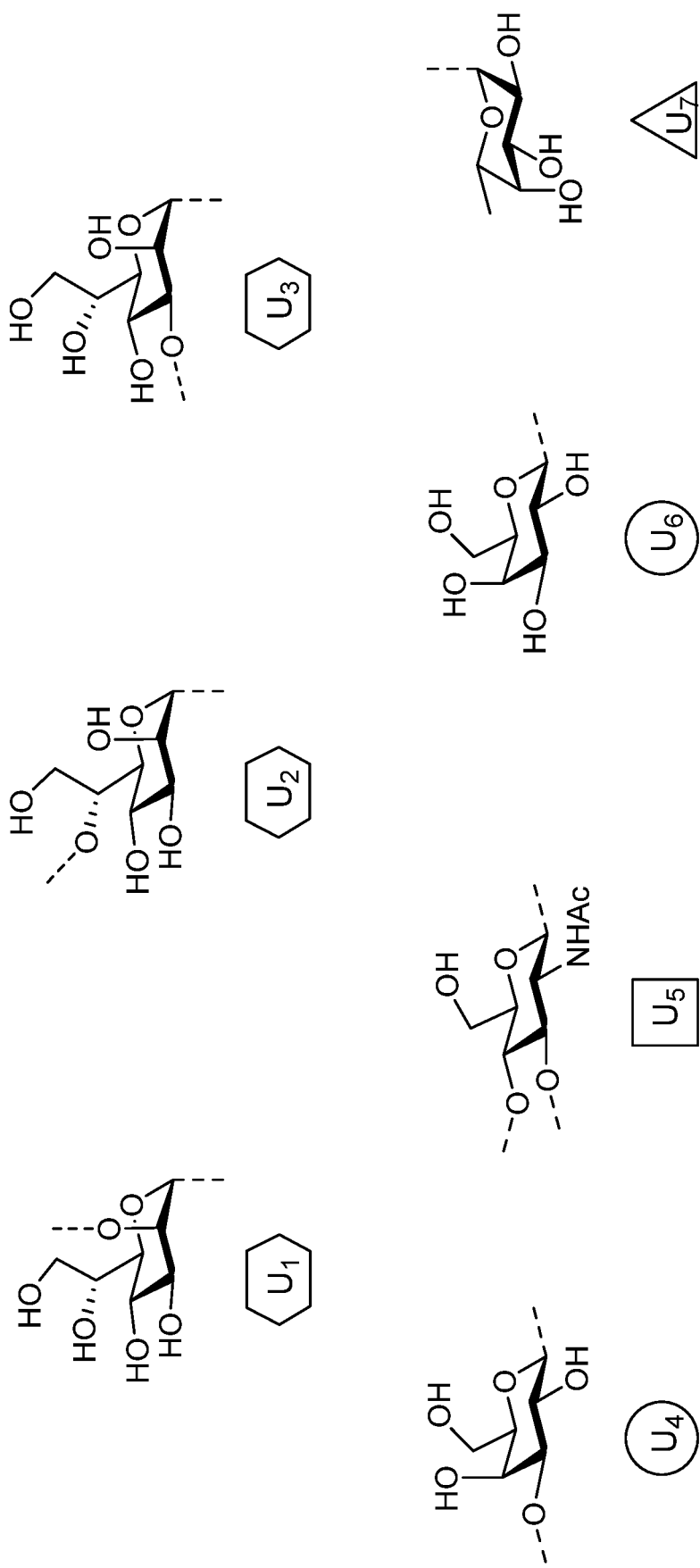
FIG. 1 shows the structural formulas of compounds represented by $U_1$, $U_2$, $U_3$, $U_4$, $U_5$, $U_6$, and $U_7$ in general formula I.
Figure 2:
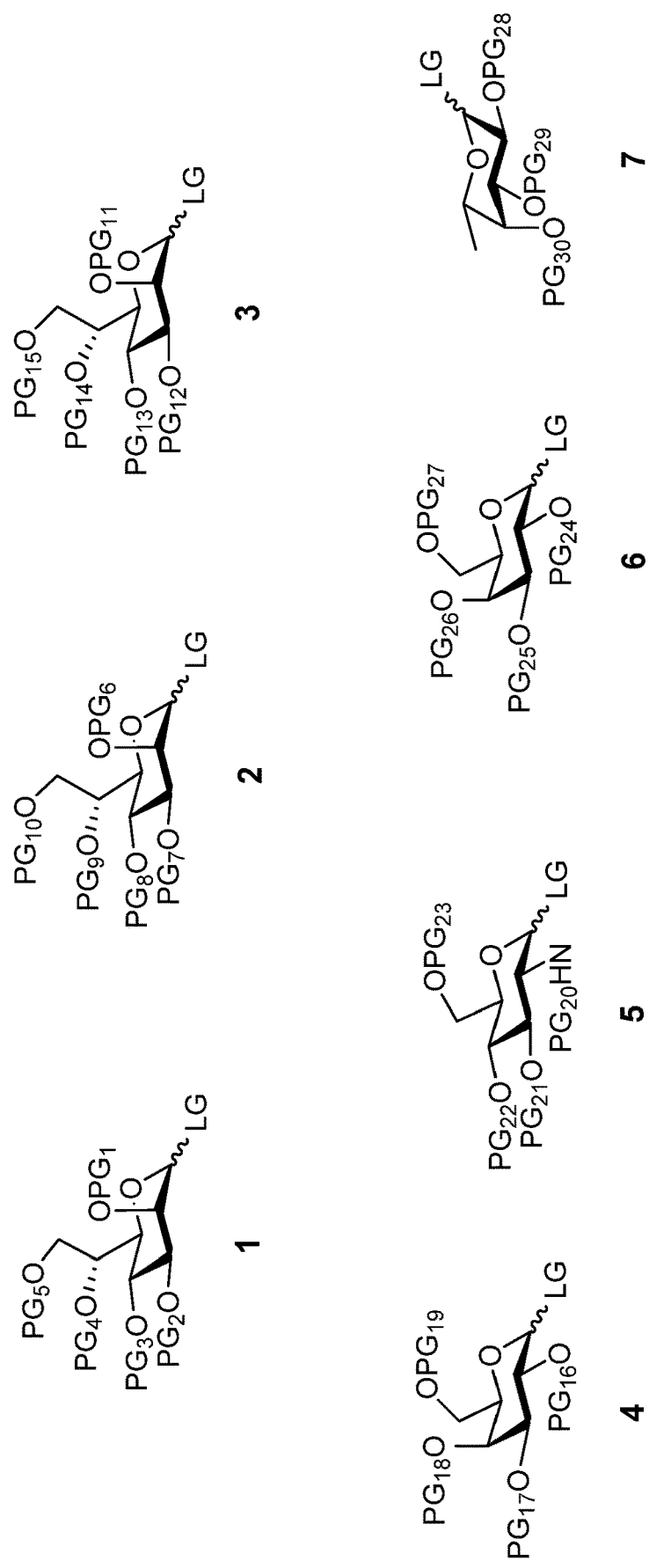
FIG. 2 shows the structural formulas of compounds represented by monosaccharide building blocks 1, 2, 3, 4, 5, 6 and 7.
Figure 3:
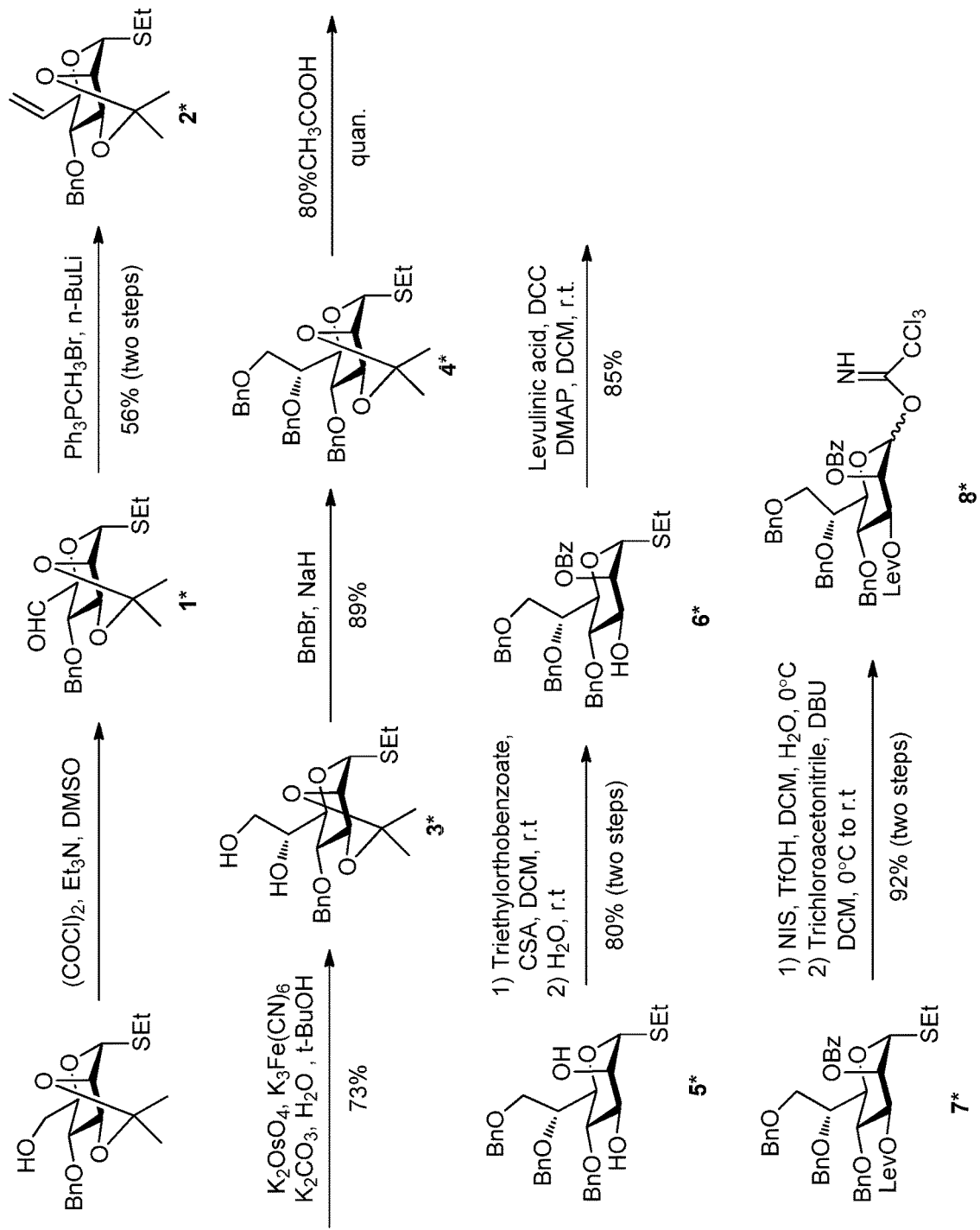
FIG. 3 is a synthetic route diagram of saccharide building blocks 6* and 8*.

The synthetic route is shown in FIG. 3.

2,3-O-propylidene-4-O-benzylmannosethioglycoside was used as a starting material, and after Swern oxidation, the 6-position hydroxyl group was oxidized to aldehyde to obtain compound 1*. Then the carbon chain at position 6 of compound 1* was extended by a Wittig reaction to obtain an olefin compound 2* deoxygenated at position 6. The olefin compound was dihydroxylated under the combined action of potassium osmate ($K_2OsO_4$), potassium ferricyanate ($K_3Fe(CN)_6$) and potassium carbonate ($K_2CO_3$) to obtain a 6,7-di-hydroxy compound 3*. The 6,7-di-hydroxyl group was protected by Bn under the action of sodium hydride (NaH) to obtain a compound 4*. After the propylidene group was removed under the action of 80% acetic acid, a compound 5* was obtained, and then under the action of D(+)-10-camphorsulfonic acid (CSA), the 2,3-position hydroxyl group was ring-protected. Ring-opening was performed under a weak acid condition to obtain a 2-OBz protected compound 6*. The 2-OH was protected by Lev to obtain a compound 7*, and then the terminal-position ethylthio group was hydrolyzed by N-iodosuccinimide (NIS) and trifluoromethanesulfonic acid (TfOH). Finally, a reaction was performed with trichloroacetonitrile to obtain a trichloroacetimidate glycosyl donor 8*.

Specific test operation and steps are as follows:

Compound 2*: Oxalyl chloride (3.6 mL, 42.3 mmol) was dissolved in dichloromethane (22 mL), and at −78° C., DMSO (6.0 mL, 84.6 mmol) in a dichloromethane solution was added dropwise. After stirring for 15 min, the compound 2,3-O-propylidene-4-O-benzylmannosethioglycoside (10.0 g, 28.2 mmol) in a dichloromethane (115 mL) solution was added to the above reaction solution by a constant pressure dropping funnel. After reaction at −78° C. for 1 h, $Et_3N$ (15.7 mL, 112.8 mmol) was added to the above solution, the reaction temperature was raised to room temperature, and then the reaction was performed at room temperature for 4 h. After it was shown by TLC that the reaction was complete, water was added to quench the reaction. The reaction solution was extracted with dichloromethane, the organic phase was washed with water and a saturated saline solution successively, and then the organic phase was dried with anhydrous $Na_2SO_4$. The organic phase was concentrated and dried under vacuum to obtain crude aldehyde, and the crude aldehyde was directly used in the next reaction without purification. Methyltriphenylphosphonium bromide (24.2 g, 67.7 mmol) was dissolved in THF (90 mL) at 0° C., and then n-BuLi (23.5 mL, 56.4 mmol, 2.5 M in hexane) was added. The reaction was performed under stirring for 1 h, then the reaction temperature was lowered to −78° C., and THF (28 mL) in which the crude aldehyde product was dissolved was added dropwise. The reaction temperature was raised to room temperature, and the reaction was continued for 12 h. After it was detected by TLC that the reaction was complete, saturated $NH_4Cl$ was added to quench the reaction, and the reaction solution was extracted with ethyl acetate (5×100 mL). The organic phase was dried with anhydrous $Na_2SO_4$, concentrated, and purified by column chromatography (petroleum ether/ethyl acetate: 100/1→50/1) to obtain the compound 2* (5.5 g, 56%). $R_f$=0.32, petroleum ether/EtOAc=15:1. $[\alpha]^{25}_D$=+129.3 (c 1.0, $CH_3Cl$). $^1H$ NMR (400 MHz, Chloroform-d) δ 7.40-7.23 (m, 5H, arom. H), 5.99 (ddd, J=16.7, 10.6, 5.5 Hz, 1H, 6-H), 5.58 (s, 1H, 1-H), 5.41 (dt, J=17.3, 1.7 Hz, 1H, 7-H), 5.25 (dt, J=10.7, 1.6 Hz, 1H, 7-H'), 4.85 (d, J=11.5 Hz, 1H, Ph-$CH_2$), 4.63 (d, J=11.5 Hz, 1H, Ph-$CH_2$), 4.42 (dd, J=10.0, 5.5 Hz, 1H, 5-H), 4.29 (dd, J=7.2, 5.7 Hz, 1H, 3-H), 4.19 (d, J=5.6 Hz, 1H, 2-H), 3.38 (dd, J=10.0, 7.2 Hz, 1H, 4-H), 2.58 (ddq, J=52.5, 13.1, 7.4 Hz, 2H, $SCH_2$), 1.49 (s, 3H, $CH_3$), 1.36 (s, 3H, $CH_3$), 1.28 (t, J=7.4 Hz, 3H, $CH_3$). $^{13}C$ NMR (101 MHz, Chloroform-d) δ 138.2, 135.0, 128.2, 128.0, 127.6, 117.3, 109.4, 80.1, 79.6, 78.5, 76.7, 73.2, 69.5, 28.0, 26.4, 24.4, 14.6. IR (film): v=2985, 2931, 1454, 1380, 1242, 1219, 1162, 1124, 1090, 1066, 996, 872, 748, 697 $cm^{-1}$. HRMS (ESI) m/z calcd for $C_{19}H_{26}O_4SNa$ $[M+Na]^+$ 373.1449, found 373.1445.

Compound 3*: Potassium ferricyanide ($K_3Fe(CN)6$, 46.2 mmol, 15.2 g), potassium osmate dihydrate ($K_2OsO_4·2H_2O$, 0.385 mmol, 142 mg) and potassium carbonate ($K_2CO_3$, 50.8 mmol, 7.0 g) were added to a solution of tert-butanol (77 mL) and water (77 mL). Then at 0° C., a solution of compound 2* (5.4 g, 15.4 mmol) in toluene (30 mL) was added dropwise to the reaction solution. The reaction mixture was reacted at 0° C. for 36 h. After it was detected by TLC that the reaction was complete, the reaction was quenched by adding sodium sulfite ($Na_2SO_3$, 25 g). After stirring for 15 min, the reaction solution was extracted with ethyl acetate. The organic phase was washed with 1 M KOH, dried with anhydrous $Na_2SO_4$, filtered and concentrated. The organic phase was separated and purified by column chromatography (petroleum ether/ethyl acetate: 5/1→4/1) to obtain the compound 3* (4.3 g, 73%). $R_f$=0.36, petroleum ether/EtOAc=1:1. $[\alpha]^{25}_D$=+173.6 (c 1.0, $CH_3Cl$). $^1H$ NMR (400 MHz, Chloroform-d) δ 7.41-7.28 (m, 5H, arom. H), 5.55 (s, 1H, 1-H), 4.98 (d, J=11.3 Hz, 1H, Ph-$CH_2$), 4.64 (d, J=11.3 Hz, 1H, Ph-$CH_2$), 4.32 (dd, J=6.9, 5.7 Hz, 1H, 3-H), 4.20 (dd, J=5.7, 0.7 Hz, 1H, 2-H), 4.06 (dd, J=9.9, 6.3 Hz, 1H, 5-H), 3.89 (ddt, J=6.8, 4.8, 2.2 Hz, 1H, 6-H), 3.69 (dd, J=10.0, 7.0 Hz, 1H, 4-H), 3.66-3.63 (m, 2H, 7-H/7-H'), 3.54 (d, J=2.8 Hz, 1H, OH), 2.63 (ddq, J=51.1, 12.9, 7.4 Hz, 2H, $SCH_2$), 1.54 (s, 3H, $CH_3$), 1.37 (s, 3H, $CH_3$), 1.29 (t, J=7.4 Hz, 3H, $CH_3$). $^{13}C$ NMR (101 MHz, Chloroform-d) δ 137.2, 109.6, 79.7, 79.5, 78.3, 76.5, 73.2, 72.8, 67.7, 62.8, 28.1, 26.4, 24.1, 14.2. IR (film): v=3446, 2984, 2931, 1454, 1380, 1242, 1219, 1162, 1066, 872, 750, 699 $cm^{-1}$. HRMS (ESI) m/z calcd for $C_{19}H_{28}O_6SNa$ $[M+Na]^+$407.1504, found 407.1507.

Compound 4*: The compound 3* (1.7 g, 4.4 mmol) was dissolved in DMF (22 mL), and sodium hydride (0.7 g, 17.7 mmol) (60% dispersed in mineral oil) was added. The reaction temperature was lowered to 0° C., and then BnBr (2.1 mL, 17.7 mmol) was added. The reaction was performed under stirring at room temperature for 3 h. After it was detected by TLC that the reaction was complete, the reaction was quenched by adding an appropriate amount of methanol. The reaction solution was extracted with dichloromethane, and the organic phase was sequentially washed with water and a saturated saline solution, dried with anhydrous $Na_2SO_4$, and concentrated under reduced pressure. The crude product was separated and purified by column chromatography (petroleum ether/ethyl acetate: 100/1→50/1) to obtain the compound 4* (2.2 g, 89%). $R_f$=0.27, petroleum ether/EtOAc=20:1. $[\alpha]^{25}_D$=+117.7 (c 1.0, $CH_3Cl$). $^1H$ NMR (400 MHz, Chloroform-d) δ 7.40-7.17 (m, 15H, arom. H), 5.54 (s, 1H, 1-H), 4.83 (d, J=11.4 Hz, 1H,) Ph-$CH_2$, 4.72 (d, J=11.8 Hz, 1H, Ph-$CH_2$), 4.67 (d, J=11.8 Hz, 1H, Ph-$CH_2$), 4.53 (d, J=11.4 Hz, 1H, Ph-$CH_2$), 4.49 (d, J=12.0 Hz, 1H, Ph-$CH_2$), 4.43 (d, J=12.0 Hz, 1H, Ph-$CH_2$), 4.32-4.24 (m, 2H, 3-H/5-H), 4.15 (d, J=5.7 Hz, 1H, 2-H), 4.04 (td, J=5.7, 1.5 Hz, 1H, 6-H), 3.68 (d, J=5.7 Hz, 2H, 7-H/7-H'), 3.68 (dd, J=10.0, 7.0 Hz, 1H, 4-H), 2.59 (ddq, J=67.5, 12.8, 7.4 Hz, 2H, $SCH_2$), 1.46 (s, 3H, $CH_3$), 1.35 (s, 3H, $CH_3$), 1.23 (t, J=7.4 Hz, 3H, $CH_3$). $^{13}C$ NMR (101 MHz, Chloroform-d) δ 138.7, 138.5, 138.2, 128.3, 128.2, 128.2, 128.0, 127.7, 127.5, 127.5, 127.4, 127.3, 109.3, 79.5, 79.0, 77.9, 76.4, 76.3, 73.2, 72.7, 72.5, 70.5, 69.3, 28.0, 26.5, 23.8, 14.2. IR (film): v=2929, 1453, 1380, 1218, 1093, 1066, 1027, 870, 734, 696 $cm^1$. HRMS (ESI) m/z calcd for $C_{33}H_{40}O_6SNa$ $[M+Na]^+$587.2443, found 587.2429.

Compound 5*: The compound 4* (2.2 g, 3.8 mmol) was dissolved in an 80% acetic acid solution (40 mL), and the reaction mixture was reacted at 60° C. for 5 h. After it was detected by TLC that the reaction was complete, the reaction solution was concentrated by rotary evaporation, and an appropriate amount of DCM was added for dissolution. Then the organic phase was sequentially washed with saturated $NaHCO_3$ and a saturated saline solution, dried with anhydrous $Na_2SO_4$, filtered and concentrated. The organic phase was separated and purified by column chromatography (petroleum ether/ethyl acetate: 4/1) to obtain the compound 5* (2 g, quan.). $R_f$=0.33, petroleum ether/EtOAc=2:1. $[\alpha]^{25}_D$=+119.6 (c 1.0, $CH_3Cl$). $^1H$ NMR (400 MHz, Chloroform-d) δ 7.45-7.14 (m, 15H, arom. H), 5.25 (d, J=1.8 Hz, 1H, 1-H), 4.74 (d, J=11.9 Hz, 1H, Ph-$CH_2$), 4.69 (d, J=11.8 Hz, 1H, Ph-$CH_2$), 4.68 (d, J=11.7 Hz, 1H, Ph-$CH_2$), 4.63 (d, J=11.5 Hz, 1H, Ph-$CH_2$), 4.53 (d, J=12.0 Hz, 1H, Ph-$CH_2$), 4.48 (d, J=11.9 Hz, 1H, Ph-$CH_2$), 4.28 (dd, J=9.5, 1.6 Hz, 1H, 5-H), 4.00 (ddd, J=6.7, 5.1, 1.6 Hz, 1H, 6-H), 3.93 (ddd, J=7.4, 3.9, 2.2 Hz, 1H, 2-H), 3.89 (dq, J=5.7, 3.4, 2.8 Hz, 1H, 3-H), 3.81 (d, J=5.2 Hz, OH), 3.79 (d, J=10.0, 5.2 Hz, 1H, 7-H), 3.77 (dd, J=10.0, 7.0 Hz, 1H, 4-H), 3.70 (dd, J=10.2, 6.7 Hz, 1H, 7-H'), 2.71-2.50 (m, 2H, $SCH_2$), 2.47 (d, J=4.6 Hz, 1H, 2-OH), 2.28 (d, J=5.7 Hz, 1H, 3-OH), 1.25 (t, J=7.4 Hz, 3H, $CH_3$). $^{13}C$ NMR (101 MHz, Chloroform-d) δ 138.6, 138.3, 138.2, 128.6, 128.4, 128.3, 127.9, 127.9, 127.8, 127.7, 127.6, 127.5, 83.4, 77.8, 76.4, 74.2, 73.4, 72.6, 72.5, 72.2, 71.7, 70.6, 24.7, 14.7. IR (film): v=3420, 2924, 1453, 1075, 1027, 792, 733, 696 $cm^{-1}$. HRMS (ESI) m/z calcd for $C_{30}H_{36}O_6SNa$ $[M+Na]^+$547.2130, found 547.2118.

Compound 6*: The compound 5* (1.06 g, 2.0 mmol) was dissolved in anhydrous DCM (20 mL), and triethyl orthobenzoate (0.7 mL, 3.0 mmol) and CSA (23 mg, 0.1 mmol) were added. The reaction was performed under stirring at room temperature for 1 h. After it was detected by TLC that the raw materials were completely converted into intermediates, water (70 µL, ~4.0 mmol) was added. The reaction was performed under stirring at room temperature for 1 h. After it was detected by TLC that the reaction was complete, an appropriate amount of DCM was added for dilution. The organic phase was washed with saturated NaHCO$_3$, and the aqueous layer was extracted once with DCM. The organic phases were combined and washed with a saturated saline solution, dried with anhydrous Na$_2$SO$_4$, filtered, concentrated, and separated and purified by column chromatography (petroleum ether/ethyl acetate: 15/1→10/1) to obtain the compound 6* (1.0 g, 80%). R$_f$=0.43, petroleum ether/EtOAc=4:1. $[\alpha]^{25}_D$=+47.5 (c 1.0, CH$_3$Cl). $^1$H NMR (400 MHz, Chloroform-d) δ 8.31-7.12 (m, 20H, arom. H), 5.42 (dd, J=3.3, 1.7 Hz, 1H, 2-H), 5.39 (d, J=1.6 Hz, 1H, 1-H), 4.82 (t, J=11.4 Hz, 2H, Ph-CH$_2$), 4.71 (dd, J=12.8, 11.5 Hz, 2H, Ph-CH$_2$), 4.53 (s, 2H, Ph-CH$_2$), 4.38-4.32 (m, 1H, 5-H), 4.20 (ddd, J=8.9, 5.4, 3.3 Hz, 1H, 3-H), 4.04 (t, J=9.4 Hz, 1H, 4-H), 4.04 (m, 1H, 6-H), 3.83 (dd, J=10.3, 5.0 Hz, 1H, 7-H), 3.74 (dd, J=10.3, 6.8 Hz, 1H, 7-H'), 2.76-2.54 (m, 2H, SCH$_2$), 2.08 (d, J=5.4 Hz, 1H, 3-OH), 1.27 (t, J=7.4 Hz, 3H, CH$_3$). $^{13}$C NMR (101 MHz, Chloroform-d) δ 166.1, 138.8, 138.4, 138.2, 133.3, 129.8, 129.7, 128.5, 128.3, 128.3, 128.0, 127.8, 127.5, 127.5, 127.4, 82.1, 78.8, 76.4, 74.8, 74.7, 73.3, 72.7, 72.2, 71.8, 71.1, 25.4, 14.9. IR (film): ν=3435, 3030, 2870, 1719, 1452, 1267, 1089, 1026, 902, 735, 711, 697 cm$^1$. HRMS (ESI) m/z calcd for C$_{37}$H$_{40}$O$_7$SNa [M+Na]$^+$651.2392, found 651.2383.

Compound 7*: The compound 6* (1.6 g, 2.5 mmol) was dissolved in anhydrous DCM (20 mL). Then levulinic acid (0.4 mL, 3.8 mmol), N,N-dicyclohexyl diimide (0.79 g, 3.8 mmol) and 4-dimethylaminopyridine (0.47 g, 3.8 mmol) were added in sequence. The reaction was performed under stirring at room temperature for 1 h. After it was detected by TLC that the reaction was complete, an appropriate amount of DCM was added for dilution. The organic layer was washed sequentially with saturated NaHCO$_3$ and a saturated saline solution, dried with anhydrous Na$_2$SO$_4$, filtered, concentrated, and separated and purified by column chromatography (petroleum ether/ethyl acetate: 10/1→8/1) to obtain the compound 7* (1.5 g, 82%). R$_f$=0.43, petroleum ether/EtOAc=3:1. $[\alpha]^{25}_D$=+27.9 (c 1.0, CH$_3$Cl). $^1$H NMR (400 MHz, Chloroform-d) δ 8.15-7.10 (m, 20H, arom. H), 5.58 (dd, J=3.2, 1.7 Hz, 1H, 2-H), 5.41 (dd, J=9.6, 3.2 Hz, 1H, 3-H), 5.37 (d, J=1.6 Hz, 1H, 1-H), 4.87 (d, J=12.0 Hz, 1H, Ph-CH$_2$), 4.75 (d, J=11.9 Hz, 1H, Ph-CH$_2$), 4.68 (d, J=11.1 Hz, 1H, Ph-CH$_2$), 4.62 (d, J=11.1 Hz, 1H, Ph-CH$_2$), 4.51 (s, 2H, Ph-CH$_2$), 4.45 (d, J=9.9 Hz, 1H, 5-H), 4.24 (t, J=9.7 Hz, 1H, 4-H), 4.04 (ddd, J=6.4, 5.0, 1.2 Hz, 1H, 6-H), 3.80 (dd, J=10.3, 5.0 Hz, 1H, 7-H), 3.72 (dd, J=10.3, 6.8 Hz, 1H, 7-H'), 2.77-2.53 (m, 4H, SCH$_2$/CH$_2$), 2.51-2.33 (m, 2H, CH$_2$), 2.07 (s, 3H, Ac), 1.27 (t, J=7.4 Hz, 3H, SCH$_2$CH$_3$). $^{13}$C NMR (101 MHz, Chloroform-d) δ 206.1, 171.7, 165.4, 138.7, 138.3, 138.0, 133.4, 129.8, 129.6, 128.5, 128.3, 128.3, 127.8, 127.6, 127.5, 127.5, 127.4, 127.4, 82.0, 78.9, 74.6, 73.5, 73.4, 73.3, 72.8, 72.4, 72.1, 71.1, 37.8, 29.7, 27.9, 25.2, 14.8. IR (film): ν=2928, 1719, 1452, 1265, 1151, 1089, 1026, 736, 711, 697 cm$^1$. HRMS (ESI) m/z calcd for C$_{42}$H$_{46}$O$_9$SNa [M+Na]$^+$749.2760, found 749.2763.

Compound 8*: The compound 7* (1.34 g, 1.84 mmol) was dissolved in CH$_2$Cl$_2$ (18 mL), and then water (0.33 mL, 18.4 mmol) was added and stirred. NIS (0.62 g, 2.76 mmol) and TfOH (36 µL, 0.41 mmol) were added at 0° C., and then stirred at 0° C. for 1.5 h. After it was detected by TLC that the reaction was complete, Et$_3$N was added to stop the reaction, and an appropriate amount of DCM was added for dilution. Then the organic phase was washed with 10% Na$_2$S$_2$O$_3$ and a saturated saline solution, dried with anhydrous Na$_2$SO$_4$, filtered, concentrated, and separated and purified by column chromatography (petroleum ether/ethyl acetate: 3/1→2/1) to obtain the corresponding hemiacetal (1.33 g, quan.). R$_f$=0.36, petroleum ether/EtOAc=1:1.

The obtained hemiacetal (238 mg, 0.35 mmol) was dissolved in CH$_2$Cl$_2$ (4 mL), and CCl$_3$CN (107 µL, 1.07 mmol) and DBU (7 µL, 0.046 mmol) were added at 0° C. The reaction was performed under stirring at room temperature for 45 min. After it was detected by TLC that the reaction was complete, the reaction solution was concentrated at 30° C. Then the reaction solution was separated and purified by silicagel column chromatography (petroleum ether/EtOAc: 6/1→4/1) to obtain the compound 8* (266 mg, 92%). R$_f$=0.33, petroleum ether/EtOAc=3:1. $^1$H NMR (400 MHz, Chloroform-d) δ 8.72 (s, 1H, arom. H), 8.13-7.93 (m, 2H, arom. H), 7.71-7.53 (m, 1H, arom. H), 7.44-7.14 (m, 16H, arom. H), 6.40 (d, J=2.1 Hz, 1H, 1-H), 5.70 (dd, J=3.3, 2.1 Hz, 1H, 2-H), 5.54 (dd, J=9.4, 3.3 Hz, 1H, 3-H), 4.89 (d, J=11.9 Hz, 1H, Ph-CH$_2$), 4.76 (d, J=11.9 Hz, 1H, Ph-CH$_2$), 4.72 (d, J=10.9 Hz, 1H, Ph-CH$_2$), 4.64 (d, J=10.9 Hz, 1H, Ph-CH$_2$), 4.47 (d, J=1.8 Hz, 2H, Ph-CH$_2$), 4.37 (t, J=9.7 Hz, 1H, 4-H), 4.30 (d, J=10.0 Hz, 1H, 5-H), 4.10 (t, J=6.4 Hz, 1H, 6-H), 3.76 (dd, J=10.2, 5.7 Hz, 1H, 7-H), 3.71 (dd, J=10.1, 6.8 Hz, 1H, 7'-H), 2.74 (dt, J=18.5, 7.2 Hz, 1H, CH$_2$), 2.62 (dt, J=18.5, 6.4 Hz, 1H, CH$_2$), 2.54-2.36 (m, 2H, CH$_2$), 2.09 (s, 3H, CH$_3$CO). $^{13}$C NMR (101 MHz, Chloroform-d) δ 206.0, 171.8, 165.2, 160.1, 138.7, 138.2, 137.7, 133.6, 129.8, 129.2, 128.6, 128.3, 128.3, 128.0, 127.7, 127.6, 127.5, 127.4, 127.4, 94.9, 90.7, 78.8, 74.9, 74.7, 73.3, 73.1, 72.6, 72.6, 70.8, 68.7, 37.8, 29.7, 27.9.

Example 2. Synthesis of Saccharide Building Block 13*

Figure 4:
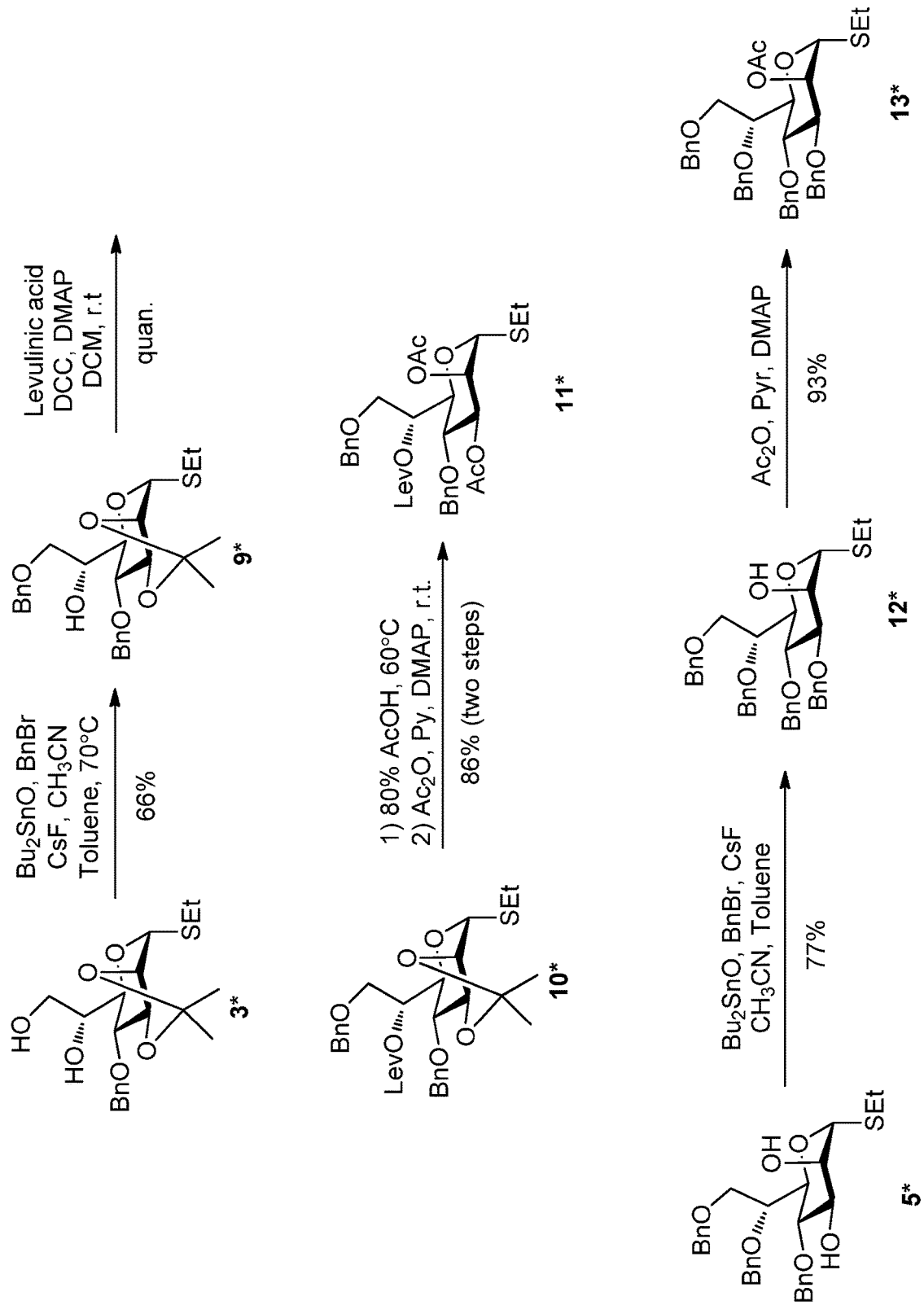
FIG. 4 is a synthetic route diagram of saccharide building blocks 11* and 13*.

The synthetic route is shown in FIG. 4.

As shown in FIG. 4, the compound 3* was used as a starting material, 7-OH was selectively protected by Bn under the action of dibutyltin oxide (Bu$_2$SnO) to obtain a compound 9*, and then 6-OH was protected by Lev to obtain a compound 10*. After the propylidene group of the compound 10* was removed under the action of 80% acetic acid, 2,3-OH was then protected by acetyl groups to obtain a saccharide building block 11*.

The saccharide building block 13* was synthesized as follows: first the previously prepared intermediate compounds 3 and 4 were used as starting materials; under the action of dibutyltin oxide (Bu$_2$SnO), the 3-OH of the compound 5* was selectively protected by Bn to obtain a compound 12*; and finally the 2-OH was protected by an acetyl group to obtain the heptose building block 13*.

The experimental procedure is as follows:

Compound 9*: The compound 3* (0.77 g, 2 mmol) and Bu$_2$SnO (0.75 g, 3 mmol) were dissolved in dry toluene (10 mL), and reflux reaction was performed for 4 h. In the process, the toluene-water azeotropic mixture (~5 mL) was removed by a Dean-Stark device, and then the reaction system was cooled to room temperature, concentrated and dried in vacuum. The above residue was dissolved in CH$_3$CN (5 mL), and then CsF (456 mg, 3 mmol) and BnBr (360 µL, 3 mmol) were added. The reaction was performed under stirring at 70° C. for 10 h. After it was detected by TLC that the reaction was complete, the reaction mixture was filtered with celite and concentrated. The crude product was separated and purified by silica gel column chromatography (petroleum ether/ethyl acetate: 8/1) to obtain the compound 9* (0.63 g, 66%). $R_f$=0.56, petroleum ether/EtOAc=3:1. $[\alpha]^{25}_D$+124.6 (c 1.0, $CH_3Cl$). $^1$H NMR (400 MHz, Chloroform-d) δ 7.48-7.21 (m, 10H, arom. H), 5.52 (s, 1H, 1-H), 4.92 (d, J=11.4 Hz, 1H, Ph-$CH_2$), 4.59 (d, J=11.3 Hz, 1H, Ph-$CH_2$), 4.53 (d, J=12.0 Hz, 1H, Ph-$CH_2$), 4.49 (d, J=12.0 Hz, 1H, Ph-$CH_2$), 4.34-4.27 (m, 1H, 3-H), 4.18 (dd, J=5.7, 0.8 Hz, 1H, 2-H), 4.13-4.04 (m, 2H, 6-H/5-H), 3.69 (dd, J=9.4, 6.9 Hz, 1H, 4-H), 3.58 (dd, J=10.3, 6.5 Hz, 1H, 7-H), 3.54 (dd, J=10.4, 3.5 Hz, 1H, 7-H'), 3.00 (d, J=2.7 Hz, 1H, 6-OH), 2.57 (ddq, J=57.7, 12.8, 7.4 Hz, 2H, $SCH_2$), 1.52 (s, 3H, $CH_3$), 1.36 (s, 3H, $CH_3$), 1.24 (t, J=7.4 Hz, 3H, $CH_3$). $^{13}$C NMR (101 MHz, Chloroform-d) δ 138.2, 137.7, 128.4, 128.3, 128.2, 127.8, 127.7, 127.6, 109.5, 79.6, 78.6, 77.9, 76.5, 73.5, 72.8, 72.3, 70.9, 68.5, 28.0, 26.4, 24.1, 14.2. IR (film): v=3482, 2984, 2930, 1454, 1380, 1241, 1219, 1162, 1068, 1027, 870, 736, 698 $cm^1$. HRMS (ESI) m/z calcd for $C_{26}H_{34}O_6SNa$ [M+Na]$^+$497.1974, found 497.1969.

Compound 10*: The compound 9* (567 mg, 1.2 mmol) was dissolved in dry $CH_2Cl_2$ (23 mL), and then LevOH (185 μL, 1.8 mmol), DCC (370 mg, 1.8 mmol) and DMAP (220 mg, 1.86 mmol) were added. The reaction was performed under stirring at room temperature for 1 h. After it was detected by TLC that the reaction was complete, an appropriate amount of DCM was added for dilution. The reaction solution was washed with saturated $NaHCO_3$ and a saturated saline solution, dried with anhydrous $Na_2SO_4$, filtered, concentrated, and purified by silica gel column chromatography (petroleum ether/ethyl acetate: 8/1→4/1) to obtain the compound 10* (707 mg, quan.). $R_f$=0.32, petroleum ether/EtOAc=4:1. $[\alpha]^{25}_D$=+105.8 (c 1.0, $CH_3Cl$). $^1$H NMR (400 MHz, Chloroform-d) δ 7.45-7.16 (m, 10H, arom. H), 5.57-5.52 (m, 1H, 6-H), 5.52 (s, 1H, 1-H), 4.87 (d, J=11.6 Hz, 1H, Ph-$CH_2$), 4.55 (d, J=11.6 Hz, 1H, Ph-$CH_2$), 4.47 (d, J=12.0 Hz, 1H, Ph-$CH_2$), 4.43 (d, J=12.0 Hz, 1H, Ph-$CH_2$), 4.26 (t, J=6.3 Hz, 1H, 3-H), 4.19 (dd, J=10.3, 2.2 Hz, 1H, 5-H), 4.13 (dd, J=5.7, 0.7 Hz, 1H, 2-H), 3.68-3.58 (m, 3H, 4-H/7-H/7-H'), 2.75-2.63 (m, 3H, $CH_2$), 2.62-2.44 (m, 3H, $SCH_2/CH_2$), 2.16 (s, 3H, OAc), 1.46 (s, 3H, $CH_3$), 1.34 (s, 3H, $CH_3$), 1.28 (t, J=7.4 Hz, 3H, $CH_3$). $^{13}$C NMR (101 MHz, Chloroform-d) δ 206.4, 171.8, 138.1, 138.1, 128.3, 128.0, 127.6, 127.5, 127.5, 109.4, 79.5, 78.8, 76.4, 76.2, 73.0, 72.5, 71.6, 68.9, 68.0, 37.9, 29.9, 28.0, 28.0, 26.4, 23.9, 14.4. IR (film): v=2984, 2931, 1739, 1719, 1361, 1218, 1159, 1096, 1066, 871, 748, 698 $cm^1$. HRMS (ESI) n/z calcd for $C_{31}H_{40}O_8SNa$ [M+Na]$^+$595.2342, found 595.2331.

Compound 11*: The compound 10* (652 mg, 1.14 mmol) was dissolved in a 80% acetic acid solution (11 mL), and the reaction mixture was reacted at 60° C. for 5 h. After it was detected by TLC that the reaction was complete, the reaction solution was concentrated by rotary evaporation. An appropriate amount of DCM was added for dissolution, and then the reaction solution was washed with saturated $NaHCO_3$ and a saturated saline solution sequentially, dried with anhydrous $Na_2SO_4$, filtered, concentrated, and dried in vacuum. The above residue was dissolved in pyridine (4 mL), then $Ac_2O$ (1.1 mL, 11.4 mmol) and DMAP (cat.) were added, and the reaction was performed under stirring at room temperature for 3 h. After it was detected by TLC that the reaction was complete, the reaction mixture was evaporated to dryness, and an appropriate amount of DCM was added for dilution. The reaction solution was sequentially washed with 1 M HCl (aq), a saturated $NaHCO_3$ and a saturated saline solution, dried with anhydrous $Na_2SO_4$, concentrated, and separated and purified by silica gel column chromatography (petroleum ether/ethyl acetate: 10/1→6/1) to obtain the compound 11* (605 mg, 86%). $R_f$=0.35, petroleum ether/EtOAc=3:1. $[\alpha]^{25}_D$=+79.9 (c 1.0, $CH_3Cl$). $^1$H NMR (400 MHz, Chloroform-d) δ 7.37-7.20 (m, 10H, arom. H), 5.51 (td, J=6.2, 2.1 Hz, 1H, 6-H), 5.30 (dd, J=3.3, 1.8 Hz, 1H, 2-H), 5.25 (dd, J=9.3, 3.3 Hz, 1H, 3-H), 5.21 (d, J=1.7 Hz, 1H, 1-H), 4.64 (s, 2H, Ph-$CH_2$), 4.51 (d, J=2.6 Hz, 2H, Ph-$CH_2$), 4.33 (dd, J=9.9, 2.1 Hz, 1H, 5-H), 4.01 (t, J=9.6 Hz, 1H, 4-H), 3.77 (dd, J=10.3, 5.8 Hz, 1H, 7-H), 3.62 (dd, J=10.2, 6.5 Hz, 1H, 7-H'), 2.74 (t, J=6.7 Hz, 2H, $CH_2$), 2.69-2.52 (m, 4H, $SCH_2/CH_2$), 2.17 (s, 3H, OAc), 2.11 (s, 3H, OAc), 1.92 (s, 3H, OAc), 1.27 (t, J=7.4 Hz, 3H, $CH_3$). $^{13}$C NMR (101 MHz, Chloroform-d) δ 206.3, 171.7, 169.9, 169.6, 138.0, 137.9, 128.4, 128.4, 127.7, 127.6, 127.6, 127.5, 81.8, 74.3, 73.8, 73.2, 72.3, 71.6, 71.5, 68.3, 37.9, 29.8, 28.0, 25.1, 20.9, 20.8, 14.8. IR (film): v=2922, 1744, 1719, 1365, 1236, 1157, 1093, 914, 734, 698 $cm^1$. HRMS (ESI) m/z calcd for $C_{32}H_{40}O_{10}SNa$ [M+Na]$^+$ 639.2240, found 639.2229.

Compound 12*: The compound 5* (600 mg, 1.14 mmol) and $Bu_2SnO$ (426 mg, 1.71 mmol) were dissolved in dry toluene (5.7 mL), and reflux reaction was performed for 4 h. In the process, the toluene-water azeotropic mixture (~3 mL) was removed by a Dean-Stark device, and then the reaction system was cooled to room temperature, concentrated and dried in vacuum. The above residue was dissolved in $CH_3CN$ (3 mL), then CsF (260 mg, 1.71 mmol) and BnBr (200 μL, 1.71 mmol) were added, and the reaction was performed under stirring at 70° C. for 10 h. After it was detected by TLC that the reaction was complete, the reaction mixture was filtered with celite and concentrated. The crude product was separated and purified by silica gel column chromatography (petroleum ether/ethyl acetate: 6/1) to obtain the compound 12* (540 mg, 77%). $R_f$=0.38, petroleum ether/EtOAc=3:1. $[\alpha]^{25}_D$=+95.5 (c 1.0, $CH_3Cl$). $^1$H NMR (400 MHz, Chloroform-d) δ 7.43-7.12 (m, 20H, arom. H), 5.33 (d, J=1.5 Hz, 1H, 1-H), 4.79 (d, J=10.9 Hz, 1H, Ph-$CH_2$), 4.75 (d, J=12.0 Hz, 1H, Ph-$CH_2$), 4.68 (d, J=12.0 Hz, 1H, Ph-$CH_2$), 4.65-4.63 (m, 2H, Ph-$CH_2$), 4.59 (d, J=10.9 Hz, 1H, Ph-$CH_2$), 4.50 (d, J=12.0 Hz, 1H, Ph-$CH_2$), 4.45 (d, J=12.1 Hz, 1H, Ph-$CH_2$), 4.30 (dd, J=9.5, 1.3 Hz, 1H, 5-H), 4.05 (dt, J=3.4, 1.7 Hz, 1H, 2-H), 3.99 (ddd, J=6.4, 4.7, 1.5 Hz, 1H, 6-H), 3.90 (t, J=9.2 Hz, 1H, 4-H), 3.85 (dd, J=8.8, 3.1 Hz, 1H, 3-H), 3.76 (dd, J=10.4, 4.6 Hz, 1H, 7-H), 3.69 (dd, J=10.5, 6.9 Hz, 1H, 7-H'), 2.72-2.47 (m, 2H, $SCH_2$), 2.58 (d, J=2.2 Hz, 1H, 2-OH), 1.24 (t, J=7.4 Hz, 3H, $CH_3$). $^{13}$C NMR (101 MHz, Chloroform-d) δ 138.7, 138.4, 138.3, 137.6, 128.6, 128.3, 128.3, 128.2, 128.1, 128.0, 127.8, 127.7, 127.6, 127.6, 127.4, 127.3, 83.0, 80.9, 78.1, 74.7, 74.6, 73.2, 72.3, 72.1, 71.9, 70.8, 69.6, 29.7, 24.6, 14.7. IR (film): v=2917, 2849, 1453, 1088, 1027, 790, 733, 696 $cm^{-1}$. HRMS (ESI) m/z calcd for $C_{37}H_{42}O_6SNa$ [M+Na]$^+$ 637.2600, found 637.2585.

Compound 13*: The compound 12* (1.2 g, 2 mmol) was dissolved in pyridine (6 mL), then $Ac_2O$ (1.1 mL, 11.4 mmol) and DMAP (cat.) were added, and the reaction was performed under stirring at room temperature for 3 h. After it was detected by TLC that the reaction was complete, the reaction mixture was evaporated to dryness, and an appropriate amount of DCM was added for dilution. The reaction solution was sequentially washed with 1 M HCl (aq), a saturated $NaHCO_3$ and a saturated saline solution, dried with anhydrous $Na_2SO_4$, concentrated, and separated and purified by silica gel column chromatography (petroleum ether/ethyl acetate: 10/1→5/1) to obtain the compound 13* (1.2 g, 93%). $R_f$=0.36, petroleum ether/EtOAc=3:1. $[\alpha]^{25}_D$=+67.4 (c 1.0, CH$_3$Cl). $^1$H NMR (400 MHz, Chloroform-d) δ 7.48-7.11 (m, 20H, arom. H), 5.39 (dd, J=3.0, 1.7 Hz, 1H, 2-H), 5.25 (d, J=1.7 Hz, 1H, 1-H), 5.25 (d, J=1.7 Hz, 1H, 1-H, Ph-CH$_2$), 4.84 (d, J=10.8 Hz, 1H, Ph-CH$_2$), 4.77 (d, J=11.9 Hz, 1H, Ph-CH$_2$), 4.68 (d, J=11.90 Hz, 1H, Ph-CH$_2$), 4.66 (d, J=11.19 Hz, 1H, Ph-CH$_2$), 4.57 (d, J=10.8 Hz, 1H, Ph-CH$_2$), 4.50 (d, J=11.8 Hz, 1H, Ph-CH$_2$), 4.50 (d, J=11.1 Hz, 1H, Ph-CH$_2$), 4.46 (d, J=12.1 Hz, 1H, Ph-CH$_2$), 4.29 (dd, J=9.3, 1.2 Hz, 1H, 5-H), 3.99 (ddd, J=6.4, 4.7, 1.5 Hz, 1H, 6-H), 3.97 (t, J=9.3 Hz, 1H, 4-H), 3.92 (dd, J=9.1, 3.0 Hz, 1H, 3-H), 3.75 (dd, J=10.4, 4.6 Hz, 1H, 7-H), 3.68 (dd, J=10.4, 6.9 Hz, 1H, 7-H'), 2.72-2.50 (m, 2H, SCH$_2$), 2.10 (s, 3H, OAc), 1.25 (t, J=7.4 Hz, 3H, CH$_3$). $^{13}$C NMR (101 MHz, Chloroform-d) δ 170.2, 138.8, 138.8, 138.4, 137.6, 128.4, 128.3, 128.2, 128.2, 127.8, 127.8, 127.5, 127.5, 127.4, 82.1, 79.0, 78.6, 74.8, 74.6, 73.3, 72.4, 72.3, 71.8, 71.1, 70.4, 25.3, 21.1, 14.8. IR (film): v=3029, 2869, 1742, 1453, 1369, 1230, 1091, 1027, 734, 696 cm$^1$. HRMS (ESI) m/z calcd for C$_{39}$H$_{44}$O$_7$SNa [M+Na]$^+$679.2705, found 679.2694.

Example 3. Synthesis of Reducing-End Trisaccharide

Figure 5:
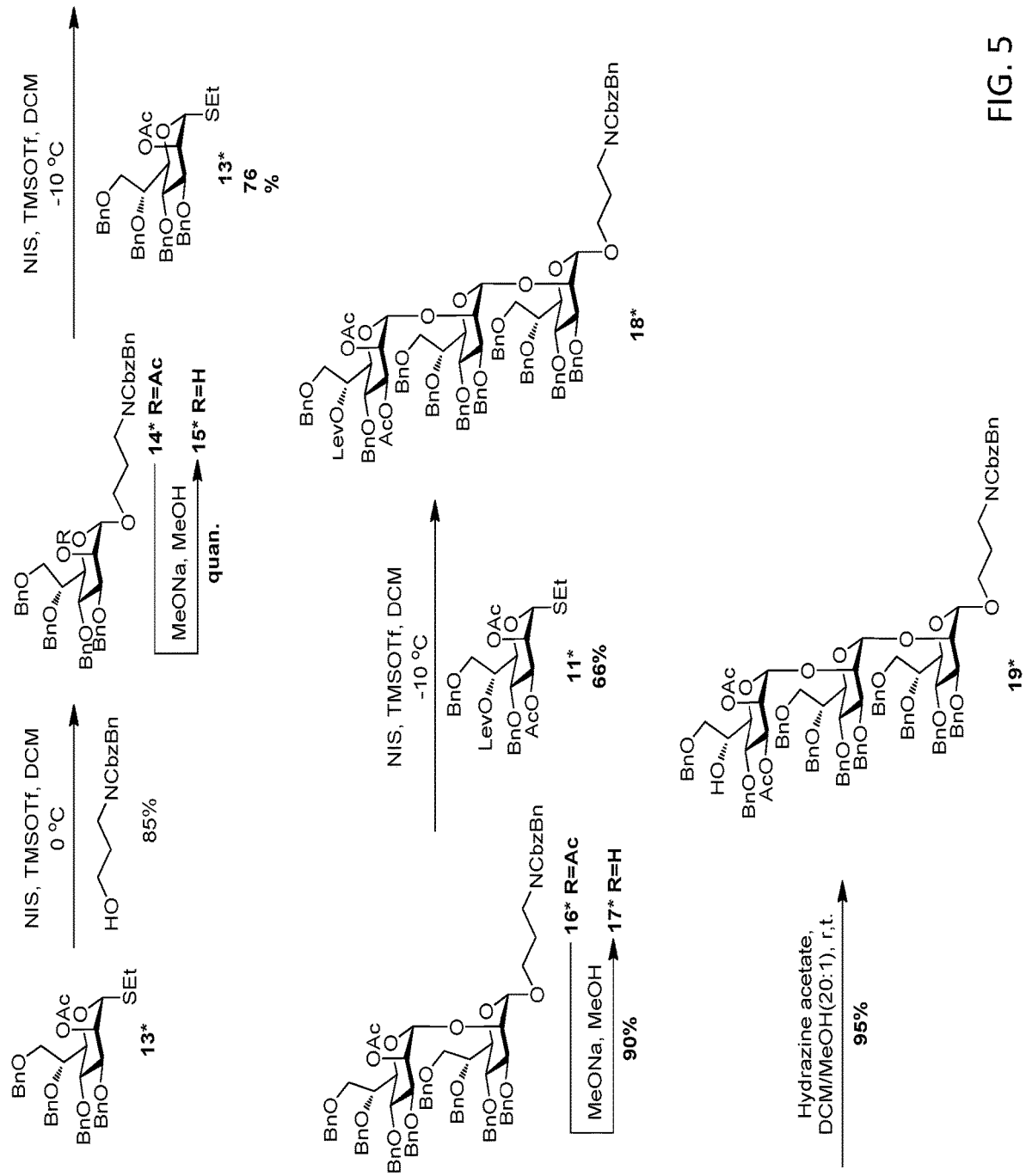
FIG. 5 is a synthetic route diagram of reducing-end trisaccharide.

The synthetic route of reducing-end trisaccharide is shown in FIG. 5.

3.1 The glycosylation reaction conditions of the reducing-end trisaccharide shown in FIG. 5 were optimized (Table 1), and the optimal glycosylation reaction conditions were determined as follows: the glycosyl donor and receptor were steamed three times in toluene; anhydrous DCM was added, the reaction concentration was 0.1 M, and activated 3 Å or 4 Å molecular sieves were added; after the mixture was cooled to −10° C. and stirred for 15 min, activating reagents TMSOTf (0.12 eq) and NIS (1.2 eq) were added, and the reaction time was 3 h. After the end of the reaction, the reaction was terminated with triethylamine (Et$_3$N). The reaction solution was filtered, diluted with DCM, washed with saturated NaHCO$_3$, dried with anhydrous Na$_2$SO$_4$, concentrated, and separated and purified by silica gel column chromatography.

Table 1. Optimization of glycosylation reaction conditions

| | Activating agent | Reaction temperature | Reaction time | Yield |
|---|---|---|---|---|
| 1 | 1. NBS, THF, H$_2$O 2. DBU, CCl$_3$CN 3. TMSOTf | −10° C. | 3 h | ≤63% |
| 2 | NIS, TMSOTf | −10° C. | 3 h | 85% |
| 3 | NIS, TMSOTf | −20° C. | 3 h | 81% |
| 4 | NIS, TMSOTf | 0° C. | 3 h | 76% |

3.2 The conditions for removing the acetyl group are as follows: the starting material was dissolved in MeOH/THF (v/v, 1:1), the reaction concentration was 0.05 M, and 0.5 equivalent of MeONa (5M in MeOH) was added. The reaction temperature was room temperature. After it was detected by TLC that the reaction was complete, the reaction solution was neutralized with Amerlite IR 120 (H$^+$) resin to reach a pH of 7. The reaction solution was filtered, concentrated, and separated and purified by silica gel column chromatography.

The experimental procedure is as follows:

Compound 14*: According to reaction conditions 3.1, the glycosyl donor 13* (980 mg, 1.49 mmol) and the glycosyl receptor linker (1.04 g, 3.43 mmol) reacted to obtain the compound 14* (1.13 g, 85%). $R_f$=0.33, petroleum ether/EtOAc=4:1. $[\alpha]^{25}_D$=+14.8 (c 1.0, CH$_3$Cl). $^1$H NMR (400 MHz, Chloroform-d) δ 7.46-7.11 (m, 30H, arom. H), 5.27 (s, 1H, 2-H), 5.17 (s, 2H, Ph-CH$_2$), 4.84 (d, J=10.7 Hz, 1H, Ph-CH$_2$), 4.78-4.59 (m, 3H, Ph-CH$_2$), 4.68 (s, 1H, 1-H), 4.56 (d, J=10.8 Hz, 1H, Ph-CH$_2$), 4.53-4.37 (m, 5H), 3.98 (t, J=5.8 Hz, 1H, 6-H), 3.94-3.78 (m, 3H, 3-H/4-H/−5-H), 3.73 (dd, J=10.4, 4.7 Hz, 1H, 7-H), 3.67 (dd, J=10.4, 6.7 Hz, 1H, 7-H'), 3.74-3.56 (m, 1H, CH$_2$), 3.44-3.20 (m, 3H, CH$_2$), 2.09 (s, 3H, CH$_3$CO), 1.89-1.64 (m, 2H, CH$_2$). $^{13}$C NMR (101 MHz, Chloroform-d) δ 170.2, 156.4 (d, J=52.1 Hz), 138.7, 138.4 (d, J=3.1 Hz), 137.8, 137.8, 136.8, 128.6, 128.4, 128.3, 128.2, 128.1, 127.9, 127.9, 127.7, 127.5, 127.4, 97.5, 78.5, 78.4, 74.8, 74.3, 73.3, 72.5, 72.2, 71.8, 70.8, 68.7, 67.2, 65.3 (d, J=22.4 Hz), 50.7 (d, J=24.7 Hz), 44.1 (d, J=91.4 Hz), 27.9 (d, J=48.9 Hz), 21.0. IR (film): v=3030, 2919, 1744, 1698, 1453, 1368, 1232 1090, 1027, 734, 696 cm$^1$. HRMS (ESI) m/z calcd for C$_{55}$H$_{59}$O$_{10}$NNa [M+Na]$^+$ 916.4037, found 916.4020.

Compound 15*: According to reaction conditions 3.2, the ester group of the compound 14* (960 mg, 1.12 mmol) was removed to obtain the compound 15* (908 mg, quan.). $R_f$=0.34, petroleum ether/EtOAc=2:1. $[\alpha]^{25}_D$=+26.8 (c 1.0, CH$_3$Cl). $^1$H NMR (400 MHz, Chloroform-d) δ 7.46-7.08 (m, 30H, arom. H), 5.23-5.11 (m, 2H, Ph-CH$_2$) 4.79 (d, J=10.8 Hz, 1H, Ph-CH$_2$), 4.75-4.60 (m, 3H, Ph-CH$_2$), 4.66 (s, 1H, 1-H), 4.58 (d, J=10.8 Hz, 1H, Ph-CH$_2$), 4.51-4.39 (m, 5H, Ph-CH$_2$), 4.02-3.93 (m, 1H, 6-H), 3.89 (s, 1H, 2-H), 3.88-3.77 (m, 3H, 3-H/4-H/5-H), 3.74 (dd, J=10.4, 4.7 Hz, 1H, 7-H), 3.68 (dd, J=10.4, 6.7 Hz, 1H, 7-H'), 3.74-3.58 (m, 1H, CH$_2$), 3.45-3.11 (m, 3H, CH$_2$), 2.35 (d, J=13.5 Hz, 1H, 2-OH), 1.88-1.62 (m, 2H, CH$_2$). $^{13}$C NMR (101 MHz, Chloroform-d) δ 156.4 (d, J=47.1 Hz), 138.7, 138.4, 138.4, 137.9, 137.8, 136.8, 128.6, 128.5, 128.5, 128.3, 128.3, 128.2, 127.9, 127.9, 127.8, 127.7, 127.6, 127.4, 127.4, 99.0, 80.7, 78.0, 74.7, 74.3, 73.2, 72.5, 72.0, 71.9, 70.6, 68.2, 67.2, 65.0, 50.7, 44.2 (d, J=86.6 Hz), 27.9 (d, J=40.6 Hz). IR (film): v=3482, 3030, 2920, 1698, 1453, 1217, 1092, 1053, 1027, 734, 696 cm$^{-1}$. HRMS (ESI) m/z calcd for C$_{53}$H$_{57}$O$_9$NNa [M+Na]$^+$874.3931, found 874.3916.

Compound 16*: According to reaction conditions 3.1, the glycosyl donor 13* (472 mg, 0.72 mmol) and the glycosyl receptor 15* (908 mg, 1.06 mmol) reacted to obtain the

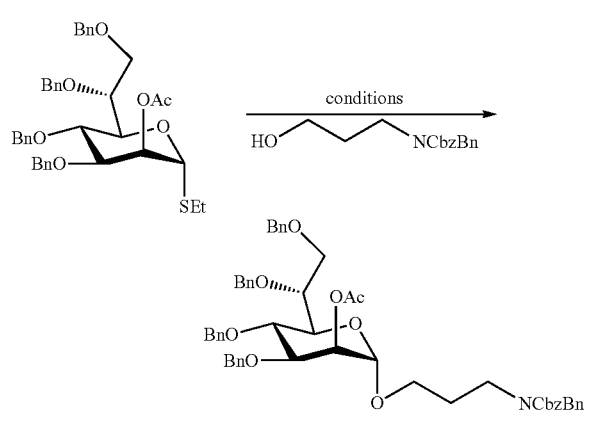

compound 16* (793 mg, 76%). $R_f$=0.51, petroleum ether/EtOAc=3:1. $[\alpha]^{25}_D$=+11.7 (c 1.0, $CH_3Cl$). $^1H$ NMR (400 MHz, Chloroform-d) δ 7.72-6.78 (m, 50H, arom. H), 5.45 (t, J=2.3 Hz, 1H, 2-H), 5.14 (d, J=11.4 Hz, 2H, Ph-$CH_2$), 4.89 (s, 1H, 1'-H), 4.88 (s, 1H, 1-H), 4.88-4.30 (m, 14H, Ph-$CH_2$), 4.25 (d, J=11.0 Hz, 1H, Ph-$CH_2$), 4.15-4.09 (m, 1H), 3.99 (dt, J=12.5, 5.8 Hz, 2H), 3.94-3.80 (m, 3H), 3.77 (dd, J=10.3, 4.9 Hz, 2H), 3.71 (dd, J=5.8, 2.6 Hz, 2H), 3.67 (dd, J=10.4, 6.5 Hz, 1H, 7-H), 3.50-3.27 (m, 1H, $CH_2$), 3.27-3.05 (m, 2H, $CH_2$), 3.05-2.83 (m, 1H, $CH_2$), 2.07 (s, 3H, $CH_3CO$), 1.72-1.43 (m, 2H, $CH_2$). $^{13}C$ NMR (101 MHz, Chloroform-d) δ 169.9, 156.3, 156.3, 138.8, 138.5, 138.4, 138.4, 138.3, 137.8, 128.5, 128.4, 128.3, 128.3, 128.3, 128.2, 128.2, 128.0, 128.0, 127.9, 127.7, 127.7, 127.6, 127.6, 127.6, 127.5, 127.5, 127.4, 127.3, 127.2, 99.9 (C-1), 98.2 (C-1'), 79.9, 78.7, 78.5, 77.6, 76.3, 74.9, 74.5, 74.4, 73.3, 73.1, 72.5, 72.4, 72.3, 72.2, 72.0, 71.7, 71.2, 70.3, 68.6, 67.1, 64.8, 60.4, 50.6, 44.0 (d, J=83.2 Hz), 27.9 (d, J=38.4 Hz), 21.0. IR (film): v=3030, 2922, 1744, 1699, 1454, 1368, 1234, 1095, 1028, 736, 697 $cm^{-1}$. HRMS (ESI) m/z calcd for $C_{90}H_{95}O_{16}NNa$ $[M+Na]^+$1468.6549, found 1468.6521.

Compound 17*: According to reaction conditions 3.2, the compound 16* (753 mg, 0.52 mmol) was deacetylated to obtain the compound 17* (657 mg, 90%). $R_f$=0.32, petroleum ether/EtOAc=3:1. $[\alpha]^{25}_D$=+13.5 (c 1.0, $CH_3Cl$). $^1H$ NMR (400 MHz, Chloroform-d) δ 7.50-6.97 (m, 36H, arom. H), 5.14 (d, J=11.3 Hz, 2H), 4.94 (s, 1H, 1'-H), 4.93 (s, 1H, 1-H), 4.87 (d, J=10.7 Hz, 1H), 4.77 (d, J=11.0 Hz, 1H), 4.68 (s, 1H), 4.66-4.53 (m, 4H), 4.50-4.34 (m, 7H), 4.10 (d, J=9.6 Hz, 1H), 4.06 (s, 1H), 3.99 (q, J=6.1 Hz, 2H), 3.92 (d, J=9.5 Hz, 1H), 3.85-3.65 (m, 7H), 3.35 (d, J=37.4 Hz, 1H), 3.14 (d, J=34.3 Hz, 2H), 2.93 (d, J=42.3 Hz, 1H), 2.33 (d, J=2.3 Hz, 1H), 1.79-1.44 (m, 2H). $^{13}C$ NMR (101 MHz, Chloroform-d) δ 156.6, 156.0, 138.9, 138.5, 138.5, 138.4, 138.4, 138.3, 137.8, 136.9, 128.5, 128.4, 128.4, 128.3, 128.2, 128.2, 128.2, 127.9, 127.9, 127.8, 127.8, 127.7, 127.7, 127.5, 127.5, 127.4, 127.4, 127.4, 127.3, 127.2, 101.6, 98.3, 80.5, 80.0, 78.9, 76.3, 74.8, 74.6, 74.4, 73.2, 73.1, 72.3, 72.3, 72.2, 71.9, 71.3, 70.2, 68.3, 67.1, 64.8, 50.6, 50.4, 44.4, 43.6, 29.7, 28.1, 27.7. IR (film): v=3030, 2918, 1698, 1453, 1216, 1054, 1027, 734, 696 $cm^{-1}$. HRMS (ESI) m/z calcd for $C_{88}H_{93}O_{15}NNa$ $[M+Na]^+$1426.6443, found 1426.6480.

Compound 18*: According to reaction conditions 3.1, the glycosyl donor 11* (258 mg, 0.42 mmol) and the glycosyl receptor 17* (487 mg, 0.42 mmol) reacted to obtain the compound 18* (441 mg, 66%). $R_f$=0.37, toluene/EtOAc=9:1. $[\alpha]^{25}_D$=+16.8 (c 1.0, $CH_3Cl$). $^1H$ NMR (400 MHz, Chloroform-d) δ 7.48-6.99 (m, 60H, arom. H), 5.61-5.54 (m, 1H), 5.38 (d, J=3.3 Hz, 1H), 5.36 (s, 1H), 5.13 (d, J=9.9 Hz, 2H), 5.11 (s, 1H, 1"-H), 4.93 (s, 1H, 1'-H), 4.82 (t, J=10.8 Hz, 3H), 4.75 (s, 1H, 1-H), 4.72-4.57 (m, 7H), 4.53-4.28 (m, 12H), 4.10 (dd, J=10.1, 5.5 Hz, 2H), 3.98 (q, J=6.9, 4.7 Hz, 3H), 3.93-3.63 (m, 12H), 3.54 (dd, J=10.1, 6.6 Hz, 1H), 3.44-3.21 (m, 1H), 3.20-2.96 (m, 2H), 2.98-2.71 (m, 1H), 2.61 (qd, J=10.9, 6.6, 5.4 Hz, 1H), 2.50 (t, J=6.4 Hz, 2H), 2.37 (m, 1H), 2.06 (s, 3H), 1.98 (s, 3H), 1.94 (s, 3H), 1.64-1.47 (m, 2H). $^{13}C$ NMR (101 MHz, Chloroform-d) δ 206.2, 171.8, 169.6, 169.4, 156.2, 156.2, 138.9, 138.8, 138.7, 138.5, 138.5, 138.0, 137.9, 136.8, 128.5, 128.3, 128.3, 128.3, 128.2, 128.2, 128.1, 128.0, 127.9, 127.8, 127.7, 127.7, 127.6, 127.6, 127.6, 127.5, 127.4, 127.4, 127.3, 127.1, 101.2, 99.5, 98.4, 79.9, 79.6, 78.9, 74.9, 74.8, 74.7, 74.5, 74.4, 73.5, 73.1, 73.1, 72.9, 72.4, 72.1, 71.7, 71.3, 70.2, 70.0, 68.1, 67.1, 65.0, 65.0, 60.4, 50.7, 50.4, 44.5, 43.7, 37.7, 29.7, 28.2, 27.8, 20.8, 20.8, 14.2. IR (film): v=3030, 2919, 1749, 1698, 1453, 1365, 1238, 1216, 1070, 1027, 735, 696 $cm^{-1}$. HRMS (ESI) m/z calcd for $C_{118}H_{131}O_{25}N_2[M+NH_4]^+$1975.9035, found 1975.9043.

Compound 19*: The compound 18* (550 mg, 0.28 mmol) was dissolved in $CH_2Cl_2$/MeOH (20/1) (3.3 mL), hydrazine acetate (40 mg, 0.42 mmol) was added, and the reaction was performed under stirring at room temperature for 3 h. After it was detected by TLC that the reaction was complete, an appropriate amount of DCM was added for dilution. Then the reaction mixture was washed with saturated $NaHCO_3$ and a saturated saline solution, dried with anhydrous $Na_2SO_4$, concentrated, and separated and purified by silica gel column chromatography (petroleum ether/ethyl acetate: 6/1→4/1) to obtain the compound 19* (494 mg, 95%). $R_f$=0.35, petroleum ether/EtOAc=3:1. $[\alpha]^{25}_D$=+25.2 (c 1.0, $CH_3Cl$). $^1H$ NMR (400 MHz, Chloroform-d) δ 7.49-7.02 (m, 60H, arom. H), 5.39 (m, 2H), 5.15 (s, 2H, $1^c$-H), 5.10 (s, 1H), 4.97 (s, 1H, $1^a$-H), 4.88 (s, 1H, $1^b$-H), 4.78 (d, J=11.0 Hz, 2H), 4.74-4.26 (m, 19H), 4.12 (m, 2H), 4.05-3.67 (m, 15H), 3.57 (dd, J=9.9, 4.4 Hz, 1H), 3.48 (dd, J=9.8, 7.4 Hz, 1H), 3.42-3.19 (m, 1H), 3.16-3.01 (m, 2H), 3.01-2.77 (m, 1H), 2.66 (s, 1H), 2.07 (s, 3H, OAc), 1.93 (s, 3H, OAc), 1.69-1.41 (m, 2H, $CH_2$). $^{13}C$ NMR (101 MHz, Chloroform-d) δ 169.8, 169.6, 156.8, 156.2, 139.1, 139.0, 138.9, 138.7, 138.7, 138.6, 138.6, 138.0, 128.7, 128.6, 128.6, 128.5, 128.4, 128.4, 128.3, 128.2, 128.1, 128.0, 127.9, 127.8, 127.8, 127.6, 127.5, 127.4, 127.4, 127.3, 101.3, 99.3, 98.4, 80.2, 79.7, 79.2, 76.7, 75.5, 75.1, 75.0, 74.8, 74.6, 73.7, 73.6, 73.4, 73.3, 73.3, 73.1, 72.5, 72.4, 72.3, 71.6, 70.9, 70.6, 70.2, 67.3, 65.1, 28.0, 21.1. IR (film): v=3030, 2920, 2360, 1750, 1698, 1453, 1366, 1239, 1218, 1072, 1028, 913, 735, 696 $cm^1$. HRMS (ESI) m/z calcd for $C_{113}H_{125}O_{23}N_2[M+NH_4]^+$ 1877.8668, found 1877.8698.

Example 4. Synthesis of Repeated Disaccharide and Trisaccharide

Figure 6:
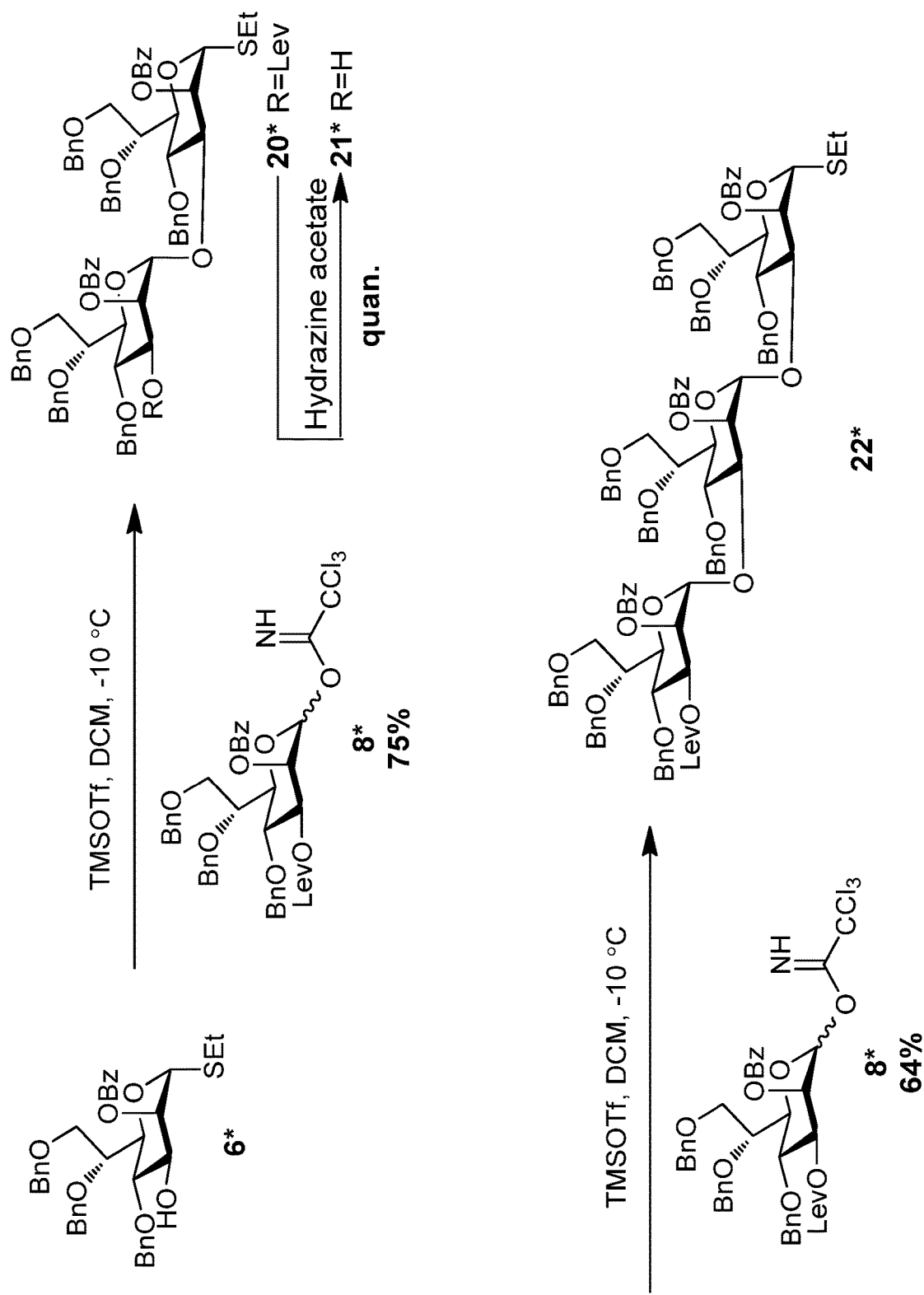
FIG. 6 is a synthetic route diagram of repeated disaccharide and trisaccharide.

The synthetic route is shown in FIG. 6. Specific test operation and steps are as follows:

4.1 If it is not specified in the disclosure, the conditions for removing the Lev group are as follows: the starting material was dissolved in $CH_2Cl_2$/MeOH (20/1, 0.1 M), hydrazine acetate (2 eq) was added, and the reaction was performed under stirring at room temperature for 3 hr. After it was detected by TLC that the reaction was complete, an appropriate amount of DCM was added for dissolution. Then the reaction mixture was washed with saturated $NaHCO_3$ and a saturated saline solution, dried with anhydrous $Na_2SO_4$, concentrated, and separated and purified by silica gel column chromatography to obtain a Lev-removed receptor.

Compound 20*: According to reaction conditions 3.1, only the activating reagent TMSOTf (0.12 eq) was added, and the glycosyl donor 8* (674 mg, 0.817 mmol) and the glycosyl receptor 6* (428 mg, 0.68 mmol) reacted to obtain the compound 20* (670 mg, 75%). $R_f$=0.36, petroleum ether/EtOAc=3:1. $[\alpha]^{25}_D$=+18.3 (c 1.0, $CH_3Cl$). $^1H$ NMR (400 MHz, Chloroform-d) δ 8.17-6.93 (m, 40H, arom. H), 5.58-5.53 (m, 2H), 5.40 (d, J=1.7 Hz, 2H, 1-H/2-H), 5.21 (d, J=2.0 Hz, 1H, 1-H), 4.94 (d, J=12.1 Hz, 1H), 4.88 (d, J=10.6 Hz, 1H), 4.80 (d, J=12.1 Hz, 1H), 4.73 (d, J=10.7 Hz, 1H), 4.69 (d, J=12.3 Hz, 1H), 4.58 (d, J=11.0 Hz, 1H), 4.55-4.45 (m, 3H), 4.39-4.35 (m, 2H), 4.30 (dd, J=9.5, 3.3 Hz, 1H), 4.27 (d, J=7.2 Hz, 1H), 4.20 (t, J=9.6 Hz, 1H), 4.06-3.94 (m, 3H), 3.78 (dd, J=10.2, 5.0 Hz, 1H), 3.70 (dd, J=10.2, 6.7 Hz, 1H), 3.52 (dd, J=10.5, 7.8 Hz, 1H), 3.29 (dd, J=10.5, 3.6 Hz, 1H), 2.71-2.46 (m, 5H), 2.43-2.27 (m, 2H, $CH_2$), 2.03 (s, 3H, $CH_3CO$), 1.25 (t, J=7.4 Hz, 3H, $CH_3$). $^{13}C$ NMR (101

MHz, Chloroform-d) δ 206.1, 171.6, 165.7, 165.2, 139.3, 138.6 (d, J=2.7 Hz), 138.3, 138.0, 137.8, 133.3, 129.9, 129.7, 129.7, 129.4, 128.6, 128.5, 128.3, 128.3, 128.2, 128.2, 127.5, 127.4, 127.4, 127.4, 127.3, 127.3, 127.1, 99.7, 82.0, 79.7, 79.4, 78.5, 75.3, 75.0, 74.2, 74.0, 73.6, 73.5, 73.3, 72.8, 72.6, 72.5, 72.5, 71.8, 70.9, 70.3, 37.8, 29.7, 28.0, 25.5, 14.9. IR (film): ν=3030, 2870, 1720, 1452, 1264, 1148, 1093, 1026, 736, 712, 697 cm$^{-1}$. HRMS (ESI) m/z calcd for C$_{77}$H$_{84}$O$_{16}$SN [M+NH$_4$]$^+$ 1310.5505, found 1310.5540.

Compound 21*: According to the reaction conditions 4.1, the Lev group of the compound 20* (440 mg, 0.34 mmol) was removed to obtain the compound 21* (405 mg, quan.). R$_f$=0.45, petroleum ether/EtOAc=3:1. [α]$^{25}_D$=+18.3 (c 1.0, CH$_3$Cl). $^1$H NMR (400 MHz, Chloroform-d) δ 8.20-6.99 (m, 40H, arom. H), 5.56 (dd, J=3.1, 1.7 Hz, 1H), 5.36 (d, J=1.6 Hz, 1H), 5.34 (dd, J=3.2, 1.8 Hz, 1H), 5.25 (d, J=1.7 Hz, 1H), 4.92 (d, J=12.1 Hz, 1H), 4.85-4.75 (m, 3H), 4.70 (dd, J=11.3, 7.8 Hz, 3H), 4.60 (d, J=11.4 Hz, 1H), 4.49 (d, J=1.2 Hz, 2H), 4.46 (d, J=12.2 Hz, 1H), 4.41-4.36 (m, 2H), 4.32 (dd, J=9.3, 3.1 Hz, 1H), 4.22 (t, J=9.6 Hz, 1H), 4.09 (pd, J=6.6, 6.0, 3.5 Hz, 1H), 4.01 (dq, J=5.5, 2.6, 1.9 Hz, 4H), 3.79 (dd, J=10.2, 5.1 Hz, 1H), 3.70 (dd, J=10.2, 6.7 Hz, 1H), 3.63 (dd, J=10.4, 7.5 Hz, 1H), 3.52 (dd, J=10.3, 4.3 Hz, 1H), 2.72-2.46 (m, 2H, CH$_2$), 1.91 (d, J=5.0 Hz, 1H, OH), 1.23 (t, J=7.4 Hz, 3H, CH$_3$). $^{13}$C NMR (101 MHz, Chloroform-d) δ 165.8, 165.4, 139.2, 138.7, 138.6, 138.3, 138.2, 137.7, 133.3, 133.2, 129.8, 129.8, 129.5, 128.6, 128.4, 128.3, 128.3, 128.2, 128.2, 128.0, 127.8, 127.6, 127.5, 127.5, 127.4, 127.4, 127.3, 127.2, 99.4, 82.1, 79.2, 78.6, 77.7, 75.6, 75.4, 75.1, 74.2, 73.8, 73.3, 73.2, 73.0, 72.8, 72.5, 72.5, 71.4, 71.0, 70.4, 25.4, 14.8. IR (film): ν=3050, 2926, 1720, 1452, 1265, 1093, 1070, 1026, 825, 736, 711, 698 cm$^{-1}$. HRMS (ESI) m/z calcd for C$_{72}$H$_{78}$O$_{14}$SN [M+NH$_4$]$^+$ 1212.5138, found 1212.5189.

Compound 22*: According to reaction conditions 3.1, only the activating reagent TMSOTf (0.12 eq) was added, and the glycosyl donor 8* (239 mg, 0.29 mmol) and the glycosyl receptor 21* (288 mg, 0.24 mmol) reacted to obtain the compound 22* (285 mg, 64%). R$_f$=0.23, petroleum ether/EtOAc=3:1. [α]$^{25}_D$=+10.2 (c 1.0, CH$_3$Cl). $^1$H NMR (400 MHz, Chloroform-d) δ 8.24-6.85 (m, 60H, arom. H), 5.57 (s, 1H), 5.56-5.52 (m, 1H), 5.49-5.42 (m, 1H), 5.39-5.36 (m, 1H), 5.37 (d, J=1.8 Hz, 1H, 1$^c$-H), 5.33 (d, J=1.9 Hz, 1H, 1$^b$-H), 4.97 (d, J=1.9 Hz, 1H, 1$^a$-H), 4.93 (d, J=10.6 Hz, 1H), 4.87 (dd, J=11.6, 5.7 Hz, 2H), 4.78 (d, J=12.1 Hz, 1H), 4.75-4.62 (m, 4H), 4.58-4.50 (m, 2H), 4.49-4.41 (m, 2H), 4.41-4.31 (m, 3H), 4.28 (d, J=12.3 Hz, 1H), 4.17 (t, J=9.8 Hz, 1H), 4.10 (d, J=12.4 Hz, 1H), 3.97 (ddd, J=11.9, 7.3, 4.2 Hz, 3H), 3.87 (d, J=9.7 Hz, 1H), 3.82 (dd, J=8.5, 2.9 Hz, 1H), 3.72 (dd, J=10.3, 4.8 Hz, 1H), 3.65 (dd, J=10.3, 6.9 Hz, 1H), 3.57 (dd, J=10.4, 7.6 Hz, 1H), 3.40-3.30 (m, 2H), 3.03 (dd, J=10.5, 3.0 Hz, 1H), 2.71-2.42 (m, 4H, CH$_2$), 2.40-2.23 (m, 2H, CH$_2$), 2.01 (s, 3H, CH$_3$CO), 1.22 (t, J=7.4 Hz, 3H, CH$_3$). $^{13}$C NMR (101 MHz, Chloroform-d) δ 206.1, 171.6, 165.5, 165.5, 165.1, 139.4, 139.2, 138.7, 138.7, 138.3, 137.9, 137.9, 137.7, 133.2, 133.2, 129.9, 129.8, 129.8, 129.7, 129.4, 129.4, 128.5, 128.4, 128.3, 128.2, 128.2, 128.1, 128.1, 128.1, 127.5, 127.5, 127.4, 127.4, 127.4, 127.3, 127.2, 127.2, 127.2, 127.1, 127.0, 127.0, 99.8, 98.7, 82.0, 80.3, 79.2, 78.6, 78.2, 75.4, 75.3, 74.9, 74.2, 74.0, 73.7, 73.6, 73.2, 73.2, 72.9, 72.6, 72.5, 72.4, 72.2, 72.1, 71.6, 71.0, 70.2, 37.8, 29.7, 27.9, 25.4, 14.9. IR (film): ν=3030, 2868, 1721, 1452, 1263, 1149, 1092, 1026, 735, 711, 696 cm$^{-1}$. HRMS (ESI) m/z calcd for C$_{112}$H$_{118}$O$_{23}$SN [M+NH$_4$]$^+$ 1876.7810, found 1876.7877.

Figure 7:
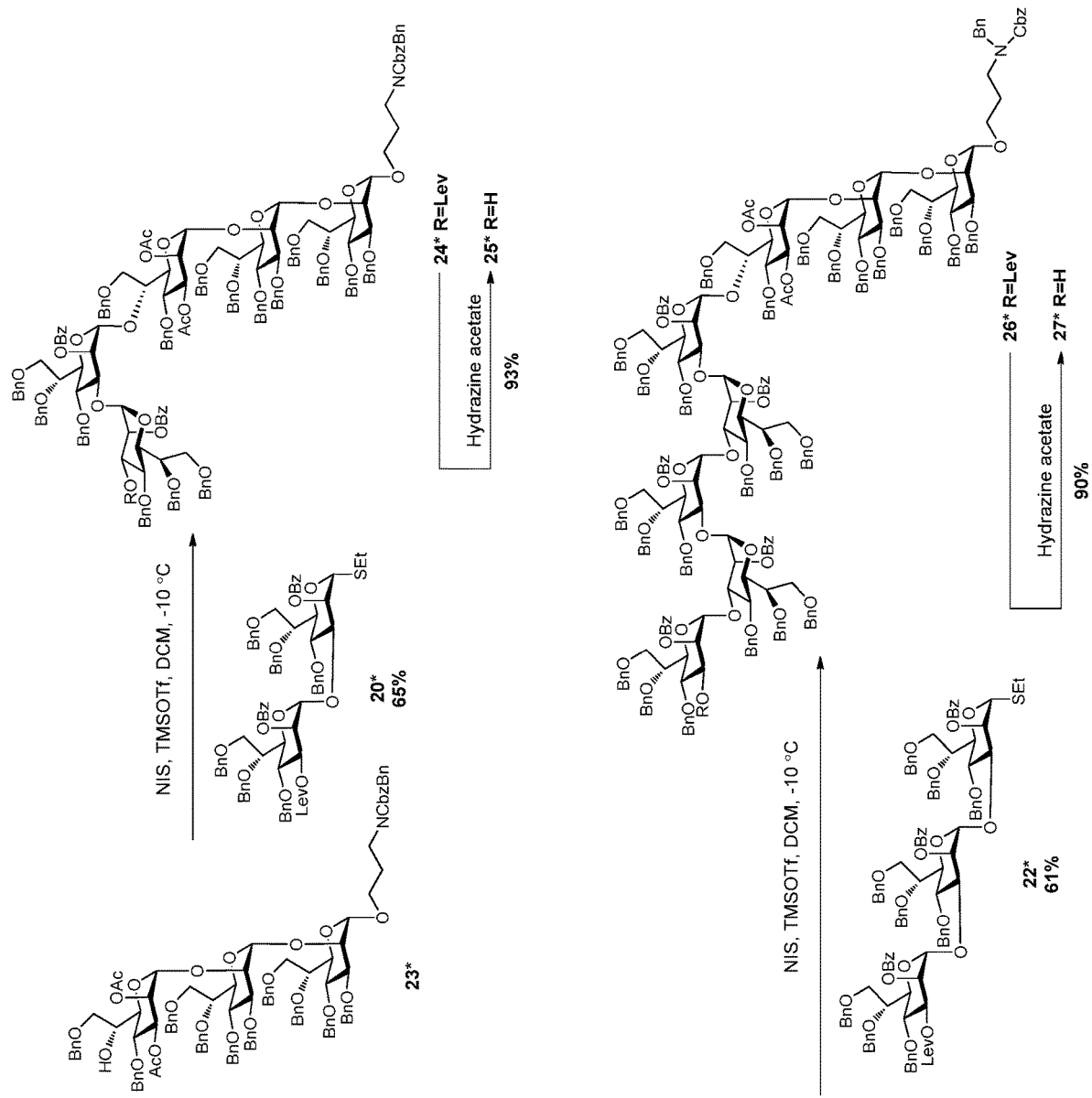
FIG. 7 is a synthetic route diagram of reducing-end pentasaccharide and octasaccharide.

The synthetic routes of reducing-end pentasaccharide and octasaccharide are shown in FIG. 7.

Compound 24*: According to reaction conditions 3.1, the glycosyl donor 20* (417 mg, 0.30 mmol, 1.2 equiv) and the glycosyl receptor 23* (452 mg, 0.243 mmol, 1 equiv) reacted to obtain the compound 24* (488 mg, 65%). R$_f$=0.18, petroleum ether/EtOAc=2:1. [α]$^{25}_D$=+14.8 (c 1.0, CH$_3$Cl). $^1$H NMR (400 MHz, Chloroform-d) δ 8.04 (d, J=7.7 Hz, 2H, arom. H), 7.93 (d, J=7.6 Hz, 2H, arom. H), 7.69-6.82 (m, 96H, arom. H), 5.73 (t, J=2.4 Hz, 1H), 5.61 (t, J=2.5 Hz, 1H), 5.49 (d, J=1.8 Hz, 1H, 1-H), 5.45 (dd, J=9.8, 3.2 Hz, 1H), 5.41 (dd, J=9.0, 2.9 Hz, 1H), 5.37 (d, J=2.3 Hz, 1H), 5.22 (s, 1H, 1-H), 5.10 (d, J=4.5 Hz, 2H), 4.94 (s, 1H, 1-H), 4.91 (d, J=2.5 Hz, 1H, 1-H), 4.90-4.81 (m, 3H), 4.80 (d, J=1.4 Hz, 1H, 1-H), 4.79-4.70 (m, 4H), 4.70-4.49 (m, 7H), 4.49-4.08 (m, 23H), 4.04 (d, J=9.8 Hz, 1H), 4.00-3.64 (m, 16H), 3.62-3.50 (m, 2H), 3.45 (tq, J=7.5, 4.2, 3.2 Hz, 3H), 3.39-3.15 (m, 2H), 3.16-2.93 (m, 2H), 2.94-2.70 (m, 1H), 2.61 (dt, J=18.2, 7.3 Hz, 1H), 2.50 (dt, J=18.2, 6.4 Hz, 1H), 2.35 (q, J=6.8 Hz, 2H), 2.08 (s, 3H, OAc), 2.02 (s, 3H, OAc), 1.77 (s, 3H, CH$_3$CO), 1.61-1.41 (m, 2H, CH$_2$). $^{13}$C NMR (101 MHz, Chloroform-d) δ 206.0, 171.6, 170.2, 169.5, 165.5, 165.2, 139.1, 139.1, 139.0, 138.9, 138.8, 138.7, 138.6, 138.6, 138.2, 138.2, 138.1, 138.0, 137.9, 137.8, 136.9, 133.3, 129.9, 129.7, 129.7, 129.5, 128.6, 128.5, 128.4, 128.3, 128.3, 128.3, 128.2, 128.2, 128.1, 128.1, 128.1, 128.0, 127.9, 127.8, 127.7, 127.7, 127.5, 127.5, 127.4, 127.3, 127.3, 127.3, 127.2, 127.2, 127.1, 127.1, 101.4, 100.3, 99.1, 98.3, 96.0, 80.1, 79.6, 79.3, 79.1, 78.9, 77.5, 76.0, 75.9, 75.3, 75.2, 75.0, 74.8, 74.7, 74.6, 74.2, 73.4, 73.4, 73.3, 73.1, 73.1, 73.0, 73.0, 72.9, 72.9, 72.7, 72.7, 72.4, 72.3, 72.3, 72.3, 72.2, 72.1, 72.1, 71.6, 71.5, 71.4, 70.5, 70.4, 69.8, 67.1, 65.0, 50.6, 43.7, 37.8, 29.6, 28.5, 28.0, 20.6, 20.6, 7.9. IR (film): ν=3030, 2917, 1748, 1722, 1453, 1365, 1265, 1240, 1071, 1026, 988, 734, 696 cm$^{-1}$. HRMS (ESI) m/z calcd for C$_{188}$H$_{195}$NO$_{39}$Na$_2$ [M+2Na]$^{2+}$ 1568.1545, found 1568.1525.

Compound 25*: According to the reaction conditions 4.1, the Lev group of the compound 24* (393 mg, 0.127 mmol) was removed to obtain the compound 25* (353 mg, 93%). R$_f$=0.48, petroleum ether/EtOAc=2:1. [α]$^{25}_D$=+19.2 (c 1.0, CH$_3$Cl). $^1$H NMR (600 MHz, Chloroform-d) δ 8.03 (d, J=7.7 Hz, 2H, arom. H), 7.92 (d, J=7.7 Hz, 2H, arom. H), 7.69-6.87 (m, 94H, arom. H), 5.77 (s, 1H), 5.53 (s, 1H), 5.47 (dd, J=9.9, 3.1 Hz, 1H), 5.44 (d, J=3.2 Hz, 1H), 5.38 (d, J=3.1 Hz, 1H), 5.31 (s, 1H), 5.13 (d, J=9.9 Hz, 2H), 4.98 (d, J=22.1 Hz, 1H), 4.94-4.85 (m, 5H), 4.84-4.59 (m, 14H), 4.59-4.47 (m, 5H), 4.47-4.10 (m, 24H), 4.06 (d, J=9.8 Hz, 1H), 4.02-3.93 (m, 7H), 3.90 (t, J=9.7 Hz, 1H), 3.87-3.68 (m, 8H), 3.62 (t, J=9.3 Hz, 1H), 3.58-3.47 (m, 4H), 3.44 (dd, J=10.4, 4.2 Hz, 1H), 3.37-3.21 (m, 1H), 3.18-2.96 (m, 3H), 2.98-2.72 (m, 1H), 2.08 (s, 3H, CH$_3$CO), 1.97 (d, J=5.0 Hz, 1H, 3-OH), 1.76 (s, 3H, CH$_3$CO), 1.64-1.46 (m, 2H, CH$_2$). $^{13}$C NMR (101 MHz, Chloroform-d) δ 170.1, 169.5, 165.9, 165.4, 139.2, 139.1, 139.0, 138.9, 138.8, 138.7, 138.6, 138.2, 138.2, 138.1, 138.0, 137.9, 136.9, 133.3, 133.2, 129.8, 129.8, 129.6, 128.6, 128.5, 128.4, 128.4, 128.3, 128.3, 128.3, 128.1, 128.0, 127.9, 127.9, 127.8, 127.8, 127.7, 127.6, 127.6, 127.5, 127.4, 127.4, 127.3, 127.2, 127.2, 127.2, 127.1, 101.4, 100.0, 99.1, 98.3, 96.0, 80.1, 79.5, 79.3, 78.9, 78.6, 78.4, 77.5, 76.0, 75.7, 75.5, 75.2, 75.0, 74.8, 74.6, 74.1, 73.4, 73.3, 73.2, 73.2, 73.1, 73.0, 73.0, 72.8, 72.4, 72.4, 72.3, 72.2, 72.1, 72.1, 71.6, 71.6, 71.3, 70.8, 70.5, 69.8, 67.1, 65.0, 60.4, 50.7, 31.6, 29.1, 22.6, 20.6, 20.6, 14.1, 14.1. IR (film): ν=3030, 2918, 1749, 1722, 1453, 1266, 1071, 1027, 734, 696 cm$^{-1}$. HRMS (ESI) m/z calcd for C$_{183}$H$_{189}$NO$_{37}$Na$_2$ [M+2Na]$^{2+}$ 1519.1361, found 1519.1348.

Compound 26*: According to reaction conditions 3.1, the glycosyl donor 22* (228 mg, 0.126 mmol) and the glycosyl receptor 25* (314 mg, 0.105 mmol) reacted to obtain the compound 26* (306 mg, 61%). $R_f$=0.29, petroleum ether/EtOAc=2:1. $[\alpha]^{25}{}_D$=+4.6 (c 0.5, CH$_3$Cl). $^1$H NMR (600 MHz, Chloroform-d) δ 8.02 (d, J=7.7 Hz, 2H, arom. H), 7.98 (d, J=7.7 Hz, 2H, arom. H), 7.88 (dd, J=12.9, 7.8 Hz, 4H, arom. H), 7.82 (d, J=7.7 Hz, 2H, arom. H), 7.62-6.72 (m, 150H), 5.67 (s, 1H), 5.61 (s, 1H), 5.46 (s, 3H), 5.41 (d, J=9.8 Hz, 1H), 5.37 (s, 1H), 5.33 (s, 2H), 5.09 (d, J=8.0 Hz, 3H), 5.03 (s, 1H), 4.99 (d, J=10.7 Hz, 1H), 4.93 (d, J=21.1 Hz, 1H), 4.85 (s, 3H), 4.77 (s, 1H), 4.68 (ddd, J=16.6, 11.0, 6.0 Hz, 4H), 4.63-4.55 (m, 5H), 4.55-4.42 (m, 8H), 4.34 (tdd, J=28.2, 17.9, 10.5 Hz, 11H), 4.25-4.10 (m, 10H), 4.10-3.92 (m, 9H), 3.92-3.82 (m, 4H), 3.82-3.64 (m, 15H), 3.60-3.22 (m, 9H), 3.17 (d, J=10.1 Hz, 1H), 3.12-3.02 (m, 1H), 2.97 (s, 1H), 2.92-2.79 (m, 3H), 2.75 (d, J=8.8 Hz, 1H), 2.55 (dt, J=18.2, 7.3 Hz, 1H), 2.45 (dt, J=18.2, 6.5 Hz, 1H), 2.30 (tt, J=18.1, 8.8 Hz, 3H, CH$_3$CO), 2.05 (s, 3H, CH$_3$CO), 1.98 (s, 3H, CH$_3$CO), 1.70 (s, 3H, CH$_3$CO), 1.54 (tt, J=14.6, 6.7 Hz, 1H, CH$_2$), 1.48-1.38 (m, 1H, CH$_2$). $^{13}$C NMR (101 MHz, Chloroform-d) δ 206.0, 171.6, 170.3, 169.6, 165.4, 165.4, 165.2, 165.1, 139.5, 139.5, 139.2, 139.2, 138.9, 138.9, 138.8, 138.8, 138.7, 138.6, 138.6, 138.2, 138.1, 137.9, 137.8, 137.6, 137.6, 136.9, 133.2, 129.9, 129.9, 129.7, 129.5, 129.5, 129.3, 128.6, 128.6, 128.5, 128.4, 128.3, 128.3, 128.2, 128.1, 128.0, 127.9, 127.8, 127.7, 127.6, 127.5, 127.4, 127.3, 127.3, 127.2, 127.2, 127.1, 127.1, 126.9, 126.8, 101.4, 99.9, 99.6, 99.1, 99.0, 98.3, 96.0, 80.6, 80.5, 80.1, 79.6, 79.2, 78.9, 75.9, 75.5, 75.1, 75.0, 74.6, 74.1, 73.9, 73.8, 73.6, 73.6, 73.5, 73.3, 73.1, 72.9, 72.9, 72.8, 72.7, 72.6, 72.6, 72.5, 72.3, 72.2, 72.1, 71.8, 71.7, 71.5, 71.4, 70.5, 70.3, 69.8, 67.1, 65.0, 60.4, 50.6, 37.7, 29.6, 27.9, 21.0, 20.6. IR (film): v=3030, 2922, 2360, 1722, 1452, 1365, 1264, 1092, 1026, 733, 696 cm$^{-1}$. HRMS (ESI) m/z calcd for C$_{293}$H$_{305}$N$_3$O$_{60}$ [M+2NH$_4$]$^{2+}$ 2412.5448, found 2412.5464.

Compound 27*: According to the reaction conditions 4.1, the Lev group of the compound 26* (300 mg, 0.063 mmol) was removed to obtain the compound 27* (264 mg, 90%). $R_f$=0.46, petroleum ether/EtOAc=2:1. $[\alpha]^{25}{}_D$=+25.6 (c 1.0, CH$_3$Cl). $^1$H NMR (600 MHz, Chloroform-d) δ 8.02 (d, J=7.7 Hz, 2H, arom. H), 7.98 (d, J=7.7 Hz, 2H, arom. H), 7.91 (d, J=7.6 Hz, 2H, arom. H), 7.86 (d, J=7.7 Hz, 2H, arom. H), 7.81 (d, J=7.7 Hz, 2H, arom. H), 7.51 (t, J=7.5 Hz, 2H, arom. H), 7.43 (q, J=7.9 Hz, 3H, arom. H), 7.37-6.79 (m, 145H, arom. H), 5.68 (s, 1H), 5.61 (s, 1H), 5.48-5.45 (m, 2H), 5.44 (s, 1H), 5.41 (dd, J=10.0, 2.9 Hz, 1H), 5.33 (s, 2H), 5.13-5.07 (m, 5H), 5.03 (s, 1H), 4.99 (d, J=10.6 Hz, 1H), 4.95 (s, OH), 4.90 (s, 1H), 4.88-4.80 (m, 5H), 4.80-4.73 (m, 3H), 4.72-4.64 (m, 5H), 4.63-4.55 (m, 5H), 4.55-4.48 (m, 6H), 4.48-4.25 (m, 16H), 4.24-4.11 (m, 10H), 4.11-3.82 (m, 15H), 3.81-3.63 (m, 18H), 3.53 (t, J=9.1 Hz, 1H), 3.47 (t, J=9.0 Hz, 1H), 3.44-3.37 (m, 1H), 3.35 (dd, J=10.5, 3.6 Hz, 1H), 3.28 (dq, J=20.0, 9.8 Hz, 3H), 3.17 (d, J=10.2 Hz, 1H), 3.07 (s, 1H), 3.01-2.93 (m, 2H), 2.87 (d, J=10.1 Hz, 3H), 2.75 (s, 1H), 2.05 (s, 3H, CH$_3$CO), 1.76 (d, J=5.3 Hz, 1H, 3-OH), 1.69 (s, 3H, CH$_3$CO), 1.47-1.40 (m, 1H, CH$_2$). $^{13}$C NMR (101 MHz, Chloroform-d) δ 170.4, 169.7, 165.7, 165.4, 165.3, 165.3, 165.2, 156.5, 139.5, 139.4, 139.2, 139.1, 138.9, 138.8, 138.7, 138.7, 138.6, 138.5, 138.2, 138.1, 138.0, 137.8, 137.7, 137.6, 137.5, 136.8, 133.3, 129.9, 129.9, 129.8, 129.6, 129.4, 129.3, 128.7, 128.6, 128.5, 128.4, 128.3, 128.3, 128.3, 128.2, 128.2, 128.2, 128.1, 128.1, 128.0, 127.9, 127.9, 127.8, 127.8, 127.7, 127.7, 127.6, 127.4, 127.4, 127.4, 127.3, 127.2, 127.2, 127.1, 127.1, 127.01, 126.9, 126.9, 101.4, 99.5, 99.0, 98.2, 95.9, 80.6, 80.4, 80.2, 80.0, 79.7, 79.6, 79.2, 78.9, 75.7, 75.5, 75.1, 75.0, 74.7, 74.5, 74.1, 73.8, 73.6, 73.6, 73.5, 73.2, 73.1, 72.9, 72.8, 72.8, 72.6, 72.6, 72.5, 72.4, 72.3, 72.2, 72.1, 71.8, 71.7, 71.4, 70.5, 69.7, 67.1, 50.6, 50.4, 44.4, 43.6, 28.2, 27.7, 20.7, 20.7. IR (film): v=3033, 2932, 1726, 1498, 1455, 1267, 1096, 737, 698 cm$^{-1}$. HRMS (ESI) m/z calcd for C$_{288}$H$_{299}$N$_3$O$_{60}$ [M+2NH$_4$]$^{2+\circ}$ 2363.5264, found 2363.5398.

Example 5. Synthesis of O-antigen tridecasaccharide of *Helicobacter pylori* serotype O:6

Figure 8A:
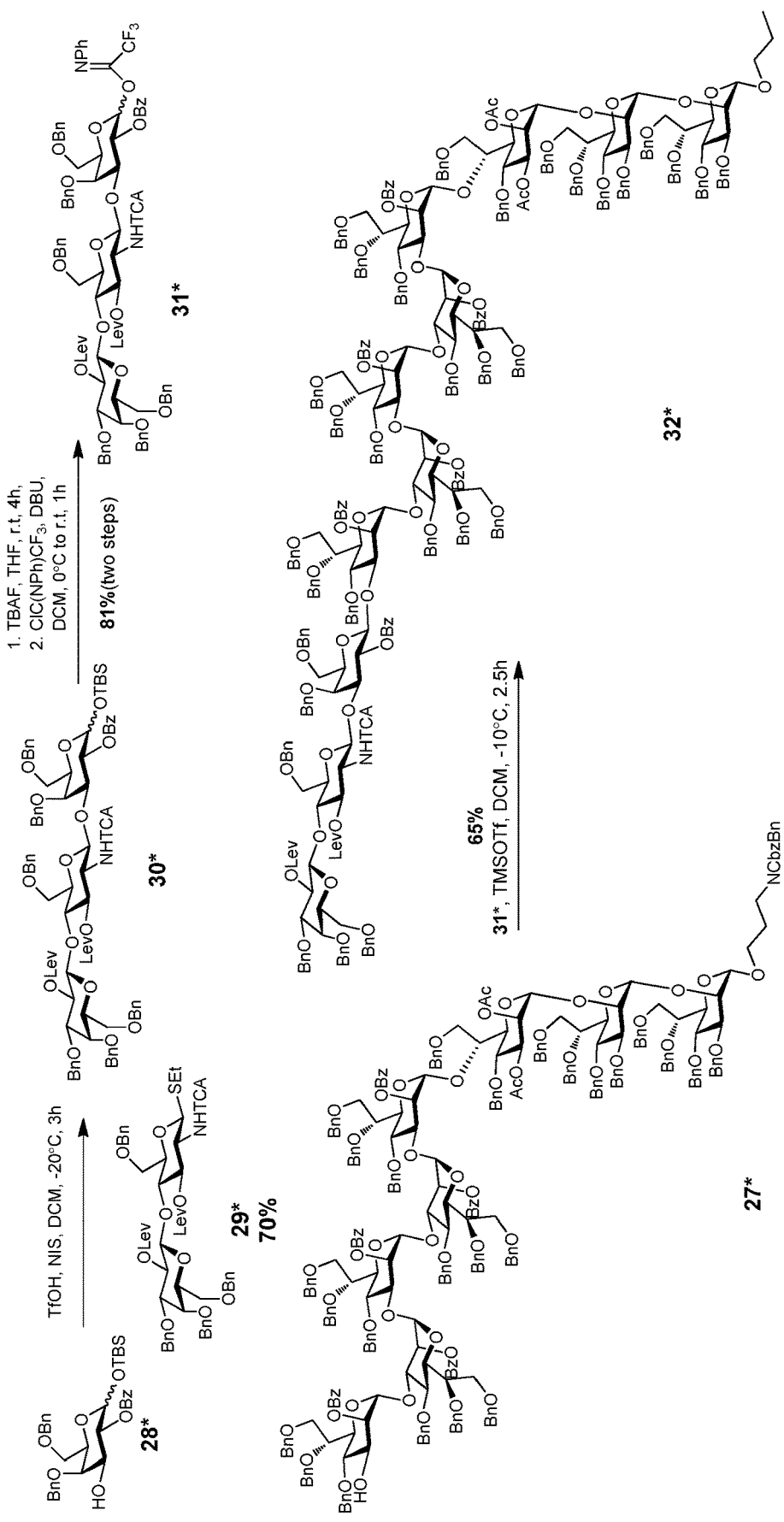
FIGS. 8A and 8B are a synthetic route diagram of O-antigen tridecasaccharide of *Helicobacter pylori* serotype O:6.
Figure 8B:
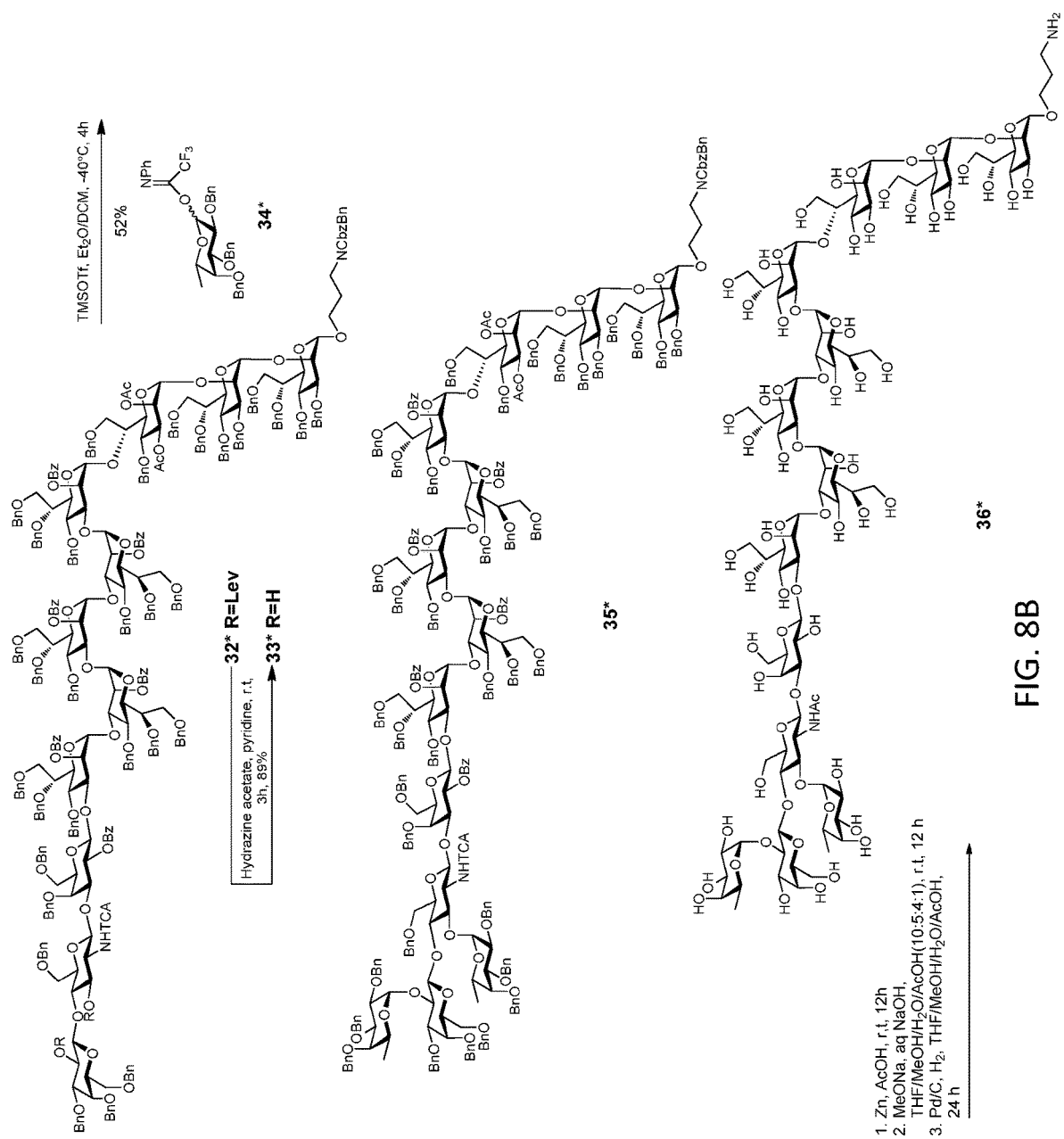

The synthetic route is shown in FIG. 8.

Compound 30*: According to reaction conditions 3.1, the activating reagents TfOH (0.2 eq) and NIS (1.2 eq) were used, and the glycosyl donor 29* (39 mg, 0.036 mmol) and the glycosyl receptor 28* (22 mg, 0.043 mmol) reacted to obtain the compound 30* (41 mg, 70%). $R_f$=0.35, Hexane/EtOAc=3:2. $[\alpha]^{25}{}_D$=−12.0 (c 1.0, CH$_3$Cl). $^1$H NMR (400 MHz, Chloroform-d) δ 8.00-7.94 (m, 2H, arom. H), 7.65-7.10 (m, 33H, arom. H), 6.36 (d, J=9.3 Hz, 1H, NH), 5.49 (dd, J=10.0, 7.6 Hz, 1H), 5.11 (dd, J=10.0, 7.9 Hz, 1H), 5.00 (d, J=11.6 Hz, 1H, Ph-CH$_2$), 4.84 (d, J=11.4 Hz, 1H, Ph-CH$_2$), 4.67 (d, J=7.8 Hz, 1H, 1-H), 4.64-4.56 (m, 3H), 4.48-4.39 (m, 6H), 4.37 (d, J=11.7 Hz, 1H, Ph-CH$_2$), 4.31 (d, J=7.9 Hz, 1H, 1-H), 4.03 (dd, J=10.2, 3.1 Hz, 1H), 4.01-3.88 (m, 5H), 3.81 (dd, J=11.1, 3.5 Hz, 1H), 3.73 (dd, J=11.1, 1.8 Hz, 1H), 3.65 (t, J=6.1 Hz, 1H), 3.61-3.48 (m, 5H), 3.38 (dd, J=8.3, 5.1 Hz, 1H), 3.33 (dd, J=10.1, 2.8 Hz, 1H), 2.77 (ddd, J=18.3, 8.0, 5.7 Hz, 1H, CH$_2$), 2.57 (dt, J=18.3, 6.0 Hz, 1H, CH$_2$), 2.52-2.41 (m, 2H, CH$_2$), 2.40-2.26 (m, 4H, CH$_2$), 2.15 (s, 3H, CH$_3$CO), 1.88 (s, 3H, CH$_3$CO), 0.69 (s, 9H, CH$_3$), 0.01 (s, 3H, SiCH$_3$), −0.07 (s, 3H, SiCH$_3$). $^{13}$C NMR (101 MHz, Chloroform-d) δ 206.5, 206.4, 172.5, 171.1, 164.7, 162.0, 138.6, 138.5, 138.1, 138.0, 137.9, 137.7, 133.2, 130.0, 129.7, 128.9, 128.6, 128.5, 128.5, 128.4, 128.4, 128.2, 128.1, 128.1, 128.0, 128.0, 127.9, 127.8, 127.7, 127.5, 127.5, 127.4, 101.2, 100.5, 96.7, 91.9, 80.2, 78.9, 75.9, 75.0, 74.8, 74.6, 74.2, 74.1, 74.0, 73.5, 73.1, 72.3, 72.2, 71.9, 71.7, 69.2, 67.8, 67.7, 55.9, 37.8, 37.7, 30.0, 29.6, 27.9, 27.8, 25.4, 17.7, −4.1, −5.4. IR (film): v=1720, 1071, 838, 700 cm$^{-1}$.

Compound 31*: The compound 30* (40 mg, 0.025 mmol) was dissolved in THF (1 mL), and then acetic acid (14 μL, 0.25 mmol) was added and stirred. TBAF/THF (1 M, 0.25 mL) was added at 0° C., and then the reaction was performed under stirring at room temperature for 4 h. After it was detected by TLC that the reaction was complete, an appropriate amount of DCM was added for dissolution. Then the reaction solution was washed with saturated NaHCO$_3$ and a saturated saline solution, dried with anhydrous Na$_2$SO$_4$, filtered, concentrated, and separated and purified by column chromatography to obtain corresponding hemiacetal.

The obtained hemiacetal was dissolved in CH$_2$Cl$_2$ (2 mL), CCl$_3$CN (18 μL, 0.125 mmol) and DBU (11 μL, 0.075 mmol) were added at 0° C., and the reaction was performed under stirring at room temperature for 1.5 min. After it was detected by TLC that the reaction was complete, the reaction solution was concentrated at 30° C., and then separated and purified by silica gel column chromatography (n-hexane/ethyl acetate: 2/1→1/1) to obtain the compound 31* (37 mg, 87%). $R_f$=0.44, Hexane/EtOAc=1:1. $[\alpha]^{25}{}_D$=7.3 (c 1.0, CH$_3$Cl). $^1$H NMR (400 MHz, Chloroform-d) δ 8.03 (d, J=7.8 Hz, 2H, arom. H), 7.72-6.96 (m, 38H, arom. H), 6.57 (d, J=7.7 Hz, 2H), 6.41 (d, J=9.3 Hz, 1H), 5.91 (s, 1H), 5.77 (t, J=9.1 Hz, 1H), 5.21-5.01 (m, 2H), 5.00-4.77 (m, 2H), 4.77-4.56 (m, 4H), 4.55-4.26 (m, 9H), 4.26-3.88 (m, 5H), 3.90-3.69 (m, 2H), 3.70-3.49 (m, 6H), 3.37 (ddd, J=22.6, 9.1, 4.0 Hz, 2H), 2.79 (ddd, J=18.3, 8.3, 5.4 Hz, 1H, CH$_2$), 2.67-2.26 (m, 7H, CH$_2$), 2.17 (s, 3H, CH$_3$CO), 1.90 (s, 3H, CH$_3$CO). $^{13}$C NMR (101 MHz, Chloroform-d) δ 206.5, 206.3, 172.6, 171.1, 164.6, 162.0, 143.2, 138.5, 138.3, 137.9, 137.8, 137.7, 137.6, 133.7, 129.8, 129.2, 128.9, 128.8, 128.6, 128.5, 128.4, 128.2, 128.0, 128.0, 127.9, 127.8, 127.8, 127.6, 127.6, 127.4, 124.2, 119.2, 101.4, 100.5, 95.4, 91.9, 80.2, 78.6, 75.4, 75.1, 75.0, 74.6, 74.0, 73.5, 73.1, 72.3, 72.0, 71.9, 71.8, 71.6, 67.7, 55.9, 37.7, 37.7, 30.0, 29.6, 27.9, 27.8. IR (film): v=2873, 1719, 1456, 1266 1210, 1164, 1096, 820, 737, 698 cm$^{-1}$.

Compound 32*: According to reaction conditions 3.1, only the activating reagent TMSOTf (0.15 eq) was added, and the glycosyl donor 31* (37 mg, 0.0223 mmol, 1.5 eq) and the glycosyl receptor 27* (70 mg, 0.0149 mmol, 1 eq) reacted to obtain the compound 32* (59 mg, 65%). R$_f$=0.26, Hexane/EtOAc=3:2. [α]$^{25}_D$=+11.8 (c 1.0, CH$_3$Cl). $^1$H NMR (700 MHz, Chloroform-d) δ 8.04 (d, J=7.6 Hz, 2H, arom. H), 7.98 (d, J=7.6 Hz, 2H, arom. H), 7.93 (d, J=7.7 Hz, 2H, arom. H), 7.85 (d, J=7.6 Hz, 2H, arom. H), 7.62-6.56 (m, 187H, arom. H), 6.06 (d, J=9.2 Hz, 1H, NH), 5.69 (s, 1H), 5.62 (d, J=3.1 Hz, 1H), 5.48 (s, 1H), 5.47 (s, 1H), 5.43 (d, J=12.4 Hz, 2H), 5.39-5.32 (m, 3H), 5.18-5.09 (m, 4H), 5.09-5.04 (m, 2H), 5.00 (d, J=10.6 Hz, 1H), 4.97-4.92 (m, 2H), 4.91-4.57 (m, 27H), 4.56-4.29 (m, 33H), 4.27-4.08 (m, 17H), 4.05-3.85 (m, 18H), 3.84-3.65 (m, 15H), 3.63 (d, J=8.8 Hz, 1H), 3.60-3.47 (m, 7H), 3.46-3.33 (m, 7H), 3.30 (t, J=9.5 Hz, 1H), 3.25 (t, J=9.6 Hz, 1H), 3.18 (d, J=9.8 Hz, 1H), 3.10 (dd, J=8.9, 5.0 Hz, 2H), 2.98 (q, J=9.3, 6.7 Hz, 2H), 2.87 (d, J=9.7 Hz, 1H), 2.84-2.75 (m, 1H), 2.73 (d, J=9.9 Hz, 1H), 2.65-2.57 (m, 2H), 2.50 (ddd, J=14.2, 8.2, 5.4 Hz, 1H), 2.44 (dd, J=16.4, 7.5 Hz, 1H), 2.41-2.26 (m, 4H, CH$_2$), 2.18 (s, 3H, CH$_3$CO), 2.07 (s, 3H, CH$_3$CO), 1.87 (s, 3H, CH$_3$CO), 1.72 (s, 3H, CH$_3$CO), 1.50-1.41 (m, 1H). $^{13}$C NMR (176 MHz, Chloroform-d) δ 206.2, 206.1, 172.4, 171.1, 170.3, 169.6, 165.3, 165.2, 165.0, 164.0, 161.8, 139.6, 139.5, 139.5, 139.2, 139.1, 139.0, 138.9, 138.9, 138.8, 138.8, 138.7, 138.6, 138.6, 138.5, 138.5, 138.1, 138.1, 138.0, 138.0, 137.9, 137.9, 137.8, 137.7, 137.4, 132.5, 129.9, 129.9, 129.6, 129.4, 129.3, 129.2, 129.1, 129.0, 128.8, 128.6, 128.6, 128.5, 128.5, 128.4, 128.3, 128.3, 128.2, 128.2, 128.1, 128.1, 128.1, 128.0, 128.0, 128.0, 127.9, 127.9, 127.8, 127.8, 127.8, 127.7, 127.7, 127.6, 127.6, 127.5, 127.5, 127.4, 127.4, 127.3, 127.3, 127.3, 127.2, 127.1, 127.1, 127.0, 127.0, 126.9, 126.9, 126.8, 126.7, 101.3, 101.1, 100.5, 99.5, 99.0, 98.8, 91.7, 80.8, 80.3, 80.0, 79.2, 78.5, 75.9, 75.8, 75.1, 75.0, 75.0, 74.7, 74.5, 74.5, 74.3, 74.0, 73.9, 73.7, 73.5, 73.5, 73.2, 73.1, 73.1, 72.9, 72.8, 72.7, 72.6, 72.4, 72.4, 72.3, 72.2, 72.2, 72.1, 72.0, 71.8, 71.7, 71.3, 70.5, 69.7, 69.0, 67.7, 67.5, 67.0, 55.7, 37.7, 29.9, 29.5, 27.8, 20.6, 20.6. IR (film): v=2928, 1724, 1455, 1267, 1097, 737, 698 cm$^{-1}$.

Compound 33*: The compound 32* (20 mg, 0.0032 mmol) was dissolved in pyridine (0.5 mL), hydrazine acetate (2 mg, 0.016 mmol) was added, and the reaction was performed under stirring at room temperature for 3 h. After it was detected by TLC that the reaction was complete, the pyridine was removed by concentration, and an appropriate amount of DCM was added for dilution. Then the reaction mixture was sequentially washed with 1 M HCl, a saturated NaHCO$_3$ and a saline solution, dried with anhydrous Na$_2$SO$_4$, concentrated, and separated and purified by silica gel column chromatography (petroleum ether/ethyl acetate: 2/1→3/2) to obtain the compound 33* (17 mg, 89%). R$_f$=0.34, Hexane/EtOAc=3:2. [α]$^{25}_D$=+13.4 (c 1.0, CH$_3$Cl). $^1$H NMR (700 MHz, Chloroform-d) δ 8.04 (d, J=7.6 Hz, 2H, arom. H), 7.98 (d, J=7.7 Hz, 2H, arom. H), 7.93 (d, J=7.7 Hz, 2H, arom. H), 7.86 (d, J=7.5 Hz, 2H, arom. H), 7.53-6.55 (m, 187H, arom. H), 6.04 (d, J=8.6 Hz, 1H, NH), 5.69 (s, 1H), 5.63 (s, 1H), 5.48 (s, 1H), 5.47 (s, 2H), 5.42 (q, J=10.5 Hz, 3H), 5.34 (d, J=7.8 Hz, 2H), 5.12 (d, J=10.4 Hz, 3H), 5.08 (s, 2H), 5.01 (d, J=10.7 Hz, 1H), 4.98-4.90 (m, 3H), 4.90-4.45 (m, 40H), 4.37 (ddt, J=45.4, 24.8, 10.6 Hz, 13H), 4.28-4.15 (m, 11H), 4.15-4.07 (m, 6H), 4.01 (dt, J=20.8, 9.3 Hz, 10H), 3.94-3.84 (m, 6H), 3.83-3.65 (m, 16H), 3.62 (d, J=9.1 Hz, 2H), 3.52 (tq, J=28.2, 9.6, 8.4 Hz, 7H), 3.37 (dtt, J=50.0, 18.4, 10.2 Hz, 7H), 3.25 (t, J=9.7 Hz, 1H), 3.19 (t, J=13.6 Hz, 1H), 3.10 (d, J=6.6 Hz, 2H), 2.99 (q, J=8.3, 6.7 Hz, 2H), 2.88 (t, J=15.7 Hz, 1H), 2.81-2.75 (m, 1H), 2.72 (d, J=10.0 Hz, 1H), 2.62 (d, J=10.3 Hz, 1H), 2.07 (s, 3H, CH$_3$CO), 1.72 (s, 3H, CH$_3$CO), 1.50-1.41 (m, 1H). $^{13}$C NMR (176 MHz, Chloroform-d) δ 170.3, 169.6, 165.3, 165.3, 165.2, 165.2, 165.1, 164.1, 161.8, 139.6, 139.5, 139.5, 139.2, 139.1, 139.0, 139.0, 138.8, 138.8, 138.7, 138.6, 138.6, 138.5, 138.4, 138.1, 138.1, 138.1, 137.9, 137.9, 137.8, 137.8, 137.7, 137.4, 137.4, 137.3, 133.2, 133.1, 132.8, 132.6, 129.9, 129.9, 129.6, 129.4, 129.3, 129.2, 129.2, 129.1, 129.0, 128.7, 128.6, 128.6, 128.5, 128.5, 128.3, 128.3, 128.3, 128.2, 128.2, 128.2, 128.2, 128.1, 128.1, 128.0, 128.0, 128.0, 127.9, 127.9, 127.9, 127.8, 127.8, 127.7, 127.7, 127.6, 127.6, 127.4, 127.4, 127.3, 127.3, 127.2, 127.1, 127.1, 127.0, 127.0, 127.0, 126.9, 126.9, 126.8, 126.7, 104.2, 101.3, 100.3, 99.5, 99.0, 98.8, 97.7, 95.9, 92.1, 82.7, 81.9, 81.2, 81.1, 80.8, 80.5, 80.0, 79.6, 79.2, 78.9, 77.9, 75.8, 75.5, 75.1, 75.0, 74.7, 74.5, 74.5, 74.4, 74.0, 74.0, 73.9, 73.8, 73.7, 73.6, 73.4, 73.2, 73.2, 73.1, 72.9, 72.8, 72.8, 72.6, 72.5, 72.4, 72.3, 72.3, 72.2, 72.1, 71.9, 71.8, 71.7, 71.4, 71.3, 71.0, 70.5, 69.7, 69.0, 68.9, 68.4, 67.5, 67.1, 57.3, 50.6, 45.3, 29.7, 20.6, 20.6. IR (film): v=3432, 3066, 3033, 2926, 2869, 1725, 1603, 1498, 1455, 1367, 1267, 1218, 1096, 1028, 912, 820, 736, 698 cm$^{-1}$.

Compound 35*: The glycosyl donor 34* (7 mg, 0.0107 mmol) and the glycosyl receptor 33* (15 mg, 0.00268 mmol, 1 eq) were mixed, dissolved in toluene and steamed twice. Dry DCM/Et$_2$O (v/v, 1:1) (0.2 mL) was added, and activated 3 Å or 4 Å molecular sieves were added. 10 eq of thiophene was added, the reaction temperature was lowered to −40° C., and the reaction mixture was stirred for 15 min. Then the activating reagent TMSOTf (0.4 eq) was added, and the reaction was performed under stirring at −40° C. for 3 h. After it was detected by TLC that the reaction was complete, an appropriate amount of Et$_3$N was added to terminate the reaction. The reaction solution was filtered, diluted with DCM, washed with saturated NaHCO$_3$ and a saturated saline solution, dried with anhydrous Na$_2$SO$_4$, concentrated, separated and purified by silica gel column chromatography (n-hexane/ethyl acetate: 2/1→3/2) to obtain the compound 35* (9 mg, 52%). R$_f$=0.48, Hexane/EtOAc=3:2. [α]$^{25}_D$=−1.5 (c 1.0, CH$_3$Cl). $^1$H NMR (700 MHz, Chloroform-d) δ 8.02 (d, J=7.7 Hz, 2H, arom. H), 7.96 (d, J=7.6 Hz, 2H, arom. H), 7.90 (d, J=7.5 Hz, 2H, arom. H), 7.83 (d, J=7.5 Hz, 2H, arom. H), 7.60-6.52 (m, 217H, arom. H), 6.35 (d, J=7.6 Hz, 1H, NH), 5.68-5.66 (m, 1H), 5.65 (d, J=4.0 Hz, 1H), 5.62-5.57 (m, 1H), 5.46 (s, 1H), 5.45-5.39 (m, 4H), 5.35-5.30 (m, 1H), 5.32 (s, 2H), 5.12-5.08 (m, 3H), 5.05 (s, 1H), 5.01-4.92 (m, 5H), 4.89 (d, J=4.2 Hz, 1H), 4.87-4.81 (m, 5H), 4.80-4.74 (m, 7H), 4.67 (ddd, J=13.6, 11.0, 6.7 Hz, 5H), 4.62-4.42 (m, 23H), 4.41-4.25 (m, 16H), 4.25-4.04 (m, 22H), 4.03-3.95 (m, 9H), 3.95-3.88 (m, 3H), 3.87-3.56 (m, 23H), 3.55-3.45 (m, 5H), 3.44-3.30 (m, 4H), 3.30-3.25 (m, 2H), 3.22 (td, J=9.8, 5.1 Hz, 2H), 3.16 (d, J=10.2 Hz, 1H), 3.12 (d, J=2.5 Hz, 1H), 3.03 (tq, J=32.8, 11.5, 9.2 Hz, 3H), 2.84 (d, J=9.6 Hz, 1H), 2.79-2.73 (m, 1H), 2.73-2.66 (m, 1H), 2.62 (d, J=9.9 Hz, 1H), 2.05 (s, 3H, CH$_3$CO), 1.70 (s, 3H, CH$_3$CO), 1.45 (ddd, J=15.8, 7.5, 4.0 Hz, 1H), 1.12 (d, J=6.3 Hz, 3H, CH$_3$-Fucose), 1.02 (d, J=6.3 Hz, 3H, CH$_3$-Fucose). $^{13}$C NMR (176 MHz, Chloroform-d) δ 170.4, 169.7, 165.5, 165.5, 165.3, 165.2, 164.6, 161.2, 156.4, 156.4, 139.7, 139.7, 139.6, 139.4, 139.2, 139.1, 139.1, 139.0, 139.0, 138.9, 138.8, 138.8, 138.7, 138.6, 138.3, 138.3, 138.2, 138.1, 138.0, 138.0, 137.9, 137.9, 137.8, 137.6, 137.5, 133.4, 133.2, 132.8, 130.1, 130.0, 129.8, 129.6, 129.5, 129.4, 129.3, 129.1, 129.0, 128.8, 128.7, 128.7, 128.6, 128.6, 128.6, 128.5, 128.5, 128.5, 128.5, 128.4, 128.3, 128.3, 128.3, 128.3, 128.2, 128.2, 128.1, 128.1, 128.0, 128.0, 128.0, 127.9, 127.9, 127.9, 127.9, 127.8, 127.8, 127.7, 127.7, 127.6, 127.6, 127.5, 127.5, 127.4, 127.4, 127.4, 127.3, 127.3, 127.2, 127.2, 127.2, 127.1, 127.1, 127.1, 127.0, 126.9, 126.8, 126.2, 101.5, 100.3, 99.6, 99.5, 99.1, 99.0, 98.4, 98.1, 97.7, 97.5, 96.0, 91.8, 84.0, 81.3, 81.2, 81.0, 80.6, 80.1, 79.8, 79.7, 79.4, 79.3, 79.2, 79.1, 78.6, 78.4, 78.3, 76.7, 76.3, 75.9, 75.8, 75.7, 75.6, 75.4, 75.2, 75.1, 75.0, 75.0, 74.9, 74.8, 74.7, 74.6, 74.3, 74.2, 74.0, 73.9, 73.9, 73.8, 73.7, 73.7, 73.5, 73.5, 73.3, 73.3, 73.2, 73.2, 73.1, 73.0, 73.0, 72.9, 72.8, 72.7, 72.6, 72.6, 72.5, 72.4, 72.4, 72.3, 72.3, 72.2, 72.2, 72.1, 72.0, 71.9, 71.8, 71.6, 71.5, 71.2, 70.6, 70.2, 69.8, 68.8, 68.1, 67.8, 67.6, 67.2, 66.9, 66.9, 66.6, 66.3, 65.0, 50.8, 50.5, 44.5, 43.8, 28.3, 27.8, 20.8, 20.8, 16.5, 16.3. IR (film): v=1725, 1266, 1096, 734, 698 cm$^{-1}$.

Compound 36*: The compound 35* (9 mg, 0.0014 mmol, 52%) was dissolved in AcOH (1 mL), newly activated zinc powder (100 mg) was added, and the reaction was performed under stirring at room temperature for 12 h. After it was detected by TLC that the raw materials disappeared, the solution was filtered and concentrated under reduced pressure. Then the solution was diluted with an appropriate amount of DCM, washed with saturated NaHCO$_3$, and dried with anhydrous Na$_2$SO$_4$. The solution was filtered, concentrated under reduced pressure, and dried in vacuum to obtain the NAc intermediate. The intermediate was dissolved in THF/MeOH (1:1, 1 mL), MeONa (30 mg) was added, and the solution was stirred at room temperature for 15 min. Then NaOH (aq, 1 M, 100 μL) was added, and the reaction was performed under stirring at room temperature for 12 h. After it was detected by TLC that the reaction was complete, the reaction solution was neutralized with Amerlite IR 120 (H$^+$) resin to reach a pH of 7. The solution was filtered, concentrated under reduced pressure, and separated and purified by silica gel column chromatography (dichloromethane/methanol: 50/1) to obtain an intermediate. The deacylated compound was dissolved in MeOH/THF/H$_2$O/AcOH (10:5:4:1, 12 mL), 10% Pd/C (50 mg) was added, and the reaction mixture was stirred in hydrogen (1 bar) for 24 h. After time-of-flight mass spectrometry detected that the reaction was complete, the solution was filtered and concentrated, dried in vacuum, and then separated and purified on a Sephadex LH20 gel column to obtain the compound 36*. $^1$H NMR (700 MHz, Deuterium Oxide) δ 5.20 (d, J=2.8 Hz, 1H, 1-H), 5.13 (s, 1H, 1-H), 5.10 (s, 1H, 1-H), 5.09 (s, 1H, 1-H), 5.06-5.01 (m, 5H, 1-H), 4.95 (s, 1H, 1-H), 4.82-4.78 (m, 1H), 4.65 (d, J=8.6 Hz, 1H, 1-H), 4.44 (dd, J=7.8, 4.1 Hz, 2H), 4.21-4.14 (m, 6H), 4.12 (s, 1H), 4.06 (s, 1H), 3.99 (t, J=9.7 Hz, 12H), 3.95-3.86 (m, 10H), 3.86-3.68 (m, 44H), 3.64 (dt, J=21.4, 9.9 Hz, 15H), 3.60-3.50 (m, 6H), 3.41-3.36 (m, 1H), 3.11-3.01 (m, 2H, CH$_2$), 1.95 (s, 3H, CH$_3$CO), 1.94-1.89 (m, 2H, CH$_2$), 1.19 (d, J=6.5 Hz, 3H, Fucose-CH$_3$), 1.18-1.13 (d, J=6.5 Hz, 3H, Fucose-CH$_3$). $^{13}$C NMR (176 MHz, Deuterium Oxide) δ 158.8, 102.1, 102.0, 101.9, 101.7, 101.2, 100.5, 100.2, 99.4, 98.5, 98.1, 82.1, 79.7, 79.0, 78.6, 78.6, 78.2, 77.9, 77.8, 76.3, 75.4, 74.8, 74.8, 74.0, 73.9, 73.8, 73.7, 73.5, 73.2, 73.1, 72.1, 71.9, 71.7, 71.5, 71.4, 71.4, 71.3, 70.6, 70.4, 70.1, 69.9, 69.7, 69.5, 69.4, 69.1, 68.7, 68.4, 68.3, 67.7, 67.7, 67.5, 67.5, 66.9, 66.8, 66.8, 66.7, 66.0, 65.7, 64.9, 62.1, 62.0, 61.7, 61.6, 61.5, 61.5, 61.0, 59.8, 37.5, 26.6, 22.3, 15.4 (d, J=3.2 Hz).

Example 6. Different Synthesis Strategies of Tridecasaccharide

In the course of the experiment, the inventors also tried other different [5+8] and [4+9] synthesis strategies, using a tetrasaccharide (FIG. 10) or a pentasaccharide (FIG. 11) as donors to construct a tridecasaccharide.

(1) Synthesis of Glycosylation Donors Tetrasaccharide and Pentasaccharide

Figure 9:
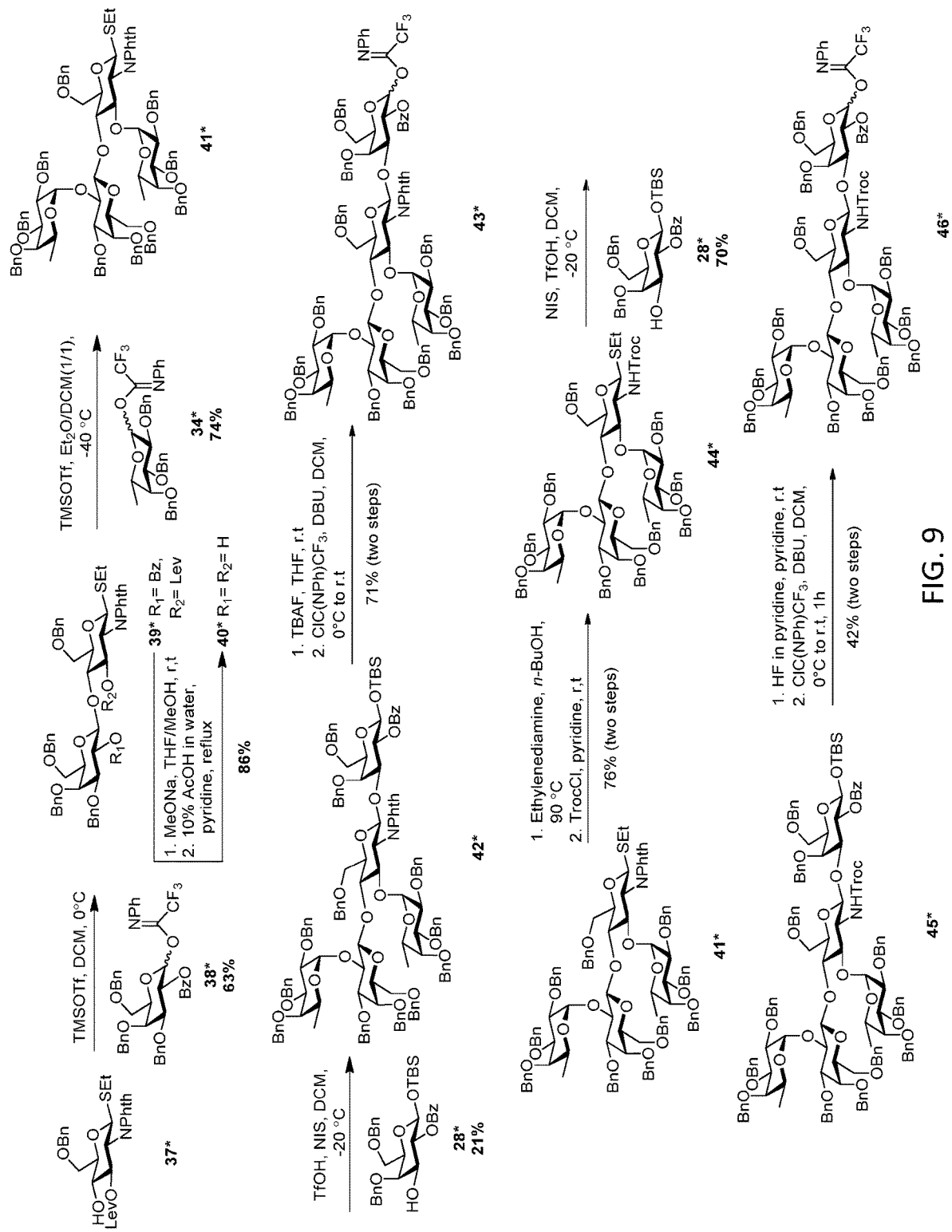
FIG. 9 is a synthetic route diagram of tetrasaccharide and pentasaccharide donors in Example 6.

The synthetic route is shown in FIG. 9.

The method uses the monosaccharide building block 37* as the receptor to react with the glycosylation donor 38* under the action of an activating reagent TMSOTf to obtain disaccharide 39*. Then the acyl groups Bz and Lev were removed using CH$_3$ONa to obtain the disaccharide receptor 40* to react with 4 equivalents of the glycosyl donor 34* to obtain the fully protected Le$^y$ tetrasaccharide. To further obtain a pentasaccharide donor, the compound 28* was used as a glycosylation receptor to react with the donor Le$^y$ tetrasaccharide to obtain pentasaccharide 42*. Since the amino protecting group Phth on the donor inactivated the activity of the donor, the reaction yield was only 21%. Then, TBS at the reducing end was removed by TBAF, and then the pentasaccharide 42* was converted into an NPh-based trifluoroacetimidate donor 43* for the subsequent glycosylation reaction.

To optimize the synthesis of the pentasaccharide, we decided to replace the amino protecting group Phth with Troc to increase the activity of the tetrasaccharide donor. First, the phthaloyl group was removed by ethylenediamine under a heating condition, and then the amino group was protected by Troc to obtain the compound 44*. Similarly, under the action of TfOH and NIS, the compound 44* reacted with the receptor 28* to obtain the compound 45*. Because part of the amino protecting group Troc was removed when TBS was removed by TBAF, we chose HF to remove TBS. Although we successfully removed TBS, we got the by-products with exposed amino groups. After separation and purification, the mixture was transformed into the NPh-based trifluoroacetimidate donor 43* for subsequent glycosylation.

The experimental procedure is as follows:

Compound 39*: The compounds 37* (270 mg, 0.50 mmol) and 38* (435 mg, 0.60 mmol) were dissolved in anhydrous CH$_2$Cl$_2$ (10 mL), and freshly activated 4 Å molecular sieves were added. The temperature was lowered to −10° C., and then TMSOTf (11 μL, 0.06 mmol) was added dropwise under argon protection. The reaction was performed at −10° C. for 3 h. After it was detected by TLC that the reaction was complete, an appropriate amount of Et$_3$N was added to quench the reaction. After being filtered and concentrated, the reaction solution was purified by silica gel column chromatography (petroleum ether/ethyl acetate: 20/1→8/1) to obtain the disaccharide compound 39* (330 mg, 63%).

Compound 40*: The compound 39* (214 mg, 0.20 mmol) was dissolved in THF/MeOH (1/1, v/v, 2 mL), and sodium methoxide (20 mg, 0.40 mmol) was added at room temperature. The reaction was performed overnight at room temperature. After it was detected by TLC that the raw materials reacted completely, methanol was added for dilution. The excess sodium methoxide was neutralized with the resin, the pH was adjusted to 0, and then the solution was filtered, concentrated, and dried in vacuum. The above crude compound was dissolved in pyridine (20 mL), 10% AcOH (2 mL) was added, and the mixture was heated to reflux for 16 h. After it was detected by TLC that the reaction was complete, the reaction solution was concentrated, dried, and purified by silica gel column chromatography (petroleum ether/ethyl acetate: 5/1→2/1) to obtain the compound 40* (150 mg, 86%).

Compound 41*: The compound 34* (412 mg, 0.68 mmol, 4 eq) and compound 40* (150 mg, 0.17 mmol, 1 eq) were dissolved in anhydrous $CH_2Cl_2/Et_2O$ (1/1, v/v, 3 mL), and 4 Å molecular sieves were added. The reaction temperature was lowered to −40° C., and then TMSOTf (12 μL) was added dropwise under the protection of argon. The reaction was performed for 2.5 h at −40° C. After it was detected by TLC that the reaction was complete, an appropriate amount of $Et_3N$ was added to quench the reaction. The solution was filtered, concentrated, and purified by silica gel column chromatography (petroleum ether/ethyl acetate: 4/1) to obtain the compound 41* (215 mg, 74%). $R_f$=0.40, Petroleum ether/EtOAc=2:1. $[\alpha]^{25}_D$=−51.2 (c 1.0, $CH_3Cl$). $^1H$ NMR (400 MHz, Chloroform-d) δ 7.91-7.65 (m, 4H, arom. H), 7.48-6.81 (m, 50H, arom. H), 5.73 (d, J=3.8 Hz, 1H, 1-H), 5.13 (d, J=10.5 Hz, 1H, 1-H), 5.00 (d, J=11.3 Hz, 1H, Ph-$CH_2$), 4.84-4.71 (m, 6H, Ph-$CH_2$), 4.68 (d, J=4.2 Hz, 1H, 1-H), 4.62 (d, J=8.3 Hz, 1H, 1-H), 4.60-4.42 (m, 9H), 4.42-4.33 (m, 2H), 4.29 (d, J=11.6 Hz, 2H), 4.23 (t, J=9.5 Hz, 1H), 4.16-4.07 (m, 2H), 4.02 (d, J=2.9 Hz, 1H), 3.92 (dd, J=11.6, 3.6 Hz, 1H), 3.89-3.82 (m, 2H), 3.81-3.65 (m, 6H), 3.62 (dd, J=9.6, 3.0 Hz, 1H), 3.41 (ddd, J=21.0, 9.6, 4.0 Hz, 2H), 3.11 (d, J=2.4 Hz, 1H), 2.83-2.63 (m, 2H, $SCH_2$), 1.43 (d, J=6.5 Hz, 3H, $CH_3$-Fucose), 1.22 (t, J=7.4 Hz, 3H, $CH_3$), 1.14 (d, J=6.4 Hz, 3H, $CH_3$-Fucose). $^{13}C$ NMR (101 MHz, Chloroform-d) δ 168.4, 167.1, 139.2, 138.8, 138.8, 138.7, 138.5, 138.4, 138.1, 138.0, 137.7, 134.3, 134.1, 131.8, 131.6, 128.7, 128.6, 128.4, 128.4, 128.3, 128.2, 128.1, 128.1, 128.0, 127.8, 127.8, 127.6, 127.5, 127.5, 127.4, 127.4, 127.3, 127.3, 127.2, 127.0, 126.9, 126.1, 123.8, 123.5, 100.0, 98.1, 97.9, 83.9, 81.5, 80.6, 79.7, 79.1, 78.3, 78.1, 75.6, 75.4, 74.9, 74.7, 73.9, 73.6, 73.3, 73.2, 73.1, 72.9, 72.8, 72.5, 72.4, 71.7, 70.9, 68.2, 67.7, 67.0, 66.8, 55.6, 23.5, 16.4, 16.2, 14.9. IR (film): v=3032, 2870, 2351, 1778, 1716, 1498, 1455, 1385, 1365, 1208, 1095, 1044, 1028, 912, 815, 735, 697 $cm^{-1}$. HRMS (ESI) m/z calcd for $C_{104}H_{109}NO_{19}SNa$ $[M+Na]^+$ 1730.7207, found 1730.7238.

Compound 42*: The donor tetrasaccharide 41* (35 mg, 0.019 mmol) and the receptor 28* (21 mg, 0.038 mmol) were dissolved in anhydrous $CH_2Cl_2$ (1 mL), and 4 Å Amolecular sieves and NIS (5 mg, 0.023 mmol) were added. The reaction temperature was lowered to −20° C., and then TfOH (0.34 μL, 0.0038 mmol) was added dropwise under argon protection. The reaction was performed at −20° C. for 3 h. After it was detected by TLC that the reaction was complete, an appropriate amount of $Et_3N$ was added to quench the reaction. The solution was filtered, washed with a 10% $Na_2S_2O_3$ solution until the solution was colorless, then sequentially washed with saturated $NaHCO_3$ and a saturated saline solution, and dried with anhydrous $Na_2SO_4$. The solution was concentrated and purified by silica gel column chromatography (n-hexane/ethyl acetate: 4/1) to obtain the compound 42* (5.5 mg, 13%).

Compound 43*: The compound 42* (11 mg, 0.005 mmol) was dissolved in THF (0.5 mL), and then acetic acid (3 μL, 0.05 mmol) was added and stirred. TBAF/THF (1 M, 0.05 mL) was added at 0° C., and then the reaction was performed at room temperature for 4 h. After it was detected by TLC that the reaction was complete, an appropriate amount of DCM was added for dissolution. Then the reaction solution was washed with saturated $NaHCO_3$ and a saturated saline solution, dried with anhydrous $Na_2SO_4$, filtered, concentrated, and separated and purified by column chromatography to obtain corresponding hemiacetal.

The obtained hemiacetal was dissolved in $CH_2Cl_2$ (0.5 mL), $CCl_3CN$ (4 μL, 0.025 mmol) and DBU (3 μL, 0.019 mmol) were added at 0° C., and the reaction was performed under stirring at room temperature for 1.5 h. After it was detected by TLC that the reaction was complete, the reaction solution was concentrated at 30° C., and then separated and purified by silica gel column chromatography (n-hexane/ethyl acetate: 5/1→/1) to obtain the compound 43* (8 mg, 71%).

Compound 44*: The compound 41* (164 mg, 0.096 mmol) was dissolved in n-BuOH (5 mL), ethylenediamine (5 mL) was added, and the reaction was performed at 95° C. for 6 h. The reaction mixture was concentrated under reduced pressure, and azeotropic evaporation was performed twice using toluene to obtain the crude compound. The crude product was dissolved in pyridine (2 mL), then TrocCl (33 μL, 0.24 mmol) was added, and the reaction was performed under stirring overnight at room temperature. After it was detected by TLC that the reaction was complete, the reaction was quenched by adding an appropriate amount of methanol at 0° C. The solution was concentrated and purified by silica gel column chromatography (n-hexane/ethyl acetate: 5:1→3:1) to obtain the compound 44* (128 mg, 76%). $R_f$=0.50, Hexane/EtOAc=2:1. $[\alpha]^{22}_D$=−45.3 (c 1.0, $CH_3Cl$). $^1H$ NMR (400 MHz, Chloroform-d) δ 7.47-6.96 (m, 50H, arom. H), 5.67 (d, J=3.9 Hz, 1H, 1-H), 5.33 (d, J=6.9 Hz, 1H, NH), 5.13 (d, J=10.2 Hz, 1H, 1-H), 4.98 (d, J=3.9 Hz, 1H, 1-H), 4.85-4.71 (m, 5H), 4.70-4.63 (m, 4H), 4.64-4.55 (m, 5H), 4.55-4.45 (m, 6H), 4.50 (d, J=8.3 Hz, 1H, 1-H), 4.41 (d, J=2.7 Hz, 2H), 4.36 (d, J=10.6 Hz, 1H), 4.26 (q, J=6.4 Hz, 1H), 4.10-4.02 (m, 3H), 4.01-3.94 (m, 3H), 3.89 (d, J=11.3 Hz, 1H), 3.85-3.73 (m, 3H), 3.73-3.67 (m, 1H), 3.66-3.61 (m, 2H), 3.61-3.58 (m, 1H), 3.55 (dd, J=9.8, 3.1 Hz, 1H), 3.32 (dd, J=8.9, 4.9 Hz, 1H), 3.22 (dd, J=10.2, 3.0 Hz, 1H), 3.16 (d, J=2.4 Hz, 1H), 3.04 (q, J=9.2 Hz, 1H), 2.74-2.53 (m, 2H), 1.32-1.18 (m, 6H, $CH_3/CH_3$-Fucose), 1.11 (d, J=6.4 Hz, 3H, $CH_3$-Fucose). $^{13}C$ NMR (101 MHz, Chloroform-d) δ 153.3, 139.3, 138.8, 138.8, 138.8, 138.7, 138.5, 138.4, 138.3, 138.1, 137.7, 128.8, 128.6, 128.5, 128.5, 128.4, 128.4, 128.3, 128.2, 128.1, 128.0, 127.8, 127.7, 127.5, 127.5, 127.4, 127.3, 127.2, 127.2, 127.1, 126.1, 100.0, 98.5, 97.9, 95.3, 83.9, 82.3, 80.2, 80.1, 79.0, 78.2, 78.2, 75.8, 75.6, 75.5, 75.4, 74.8, 74.4, 74.3, 73.5, 73.5, 73.2, 72.9, 72.7, 72.4, 72.4, 72.3, 71.9, 70.9, 68.1, 67.7, 59.1, 24.3, 16.4, 16.2, 15.3. IR (film): v=2871, 1741, 1498, 1455, 1364, 1096, 822, 736, 697 $cm^{-1}$. HRMS (ESI) m/z calcd for $C_{99}H_{112}Cl_3NO_{19}S$ $[M+NH_4]^+$ 1769.6640, found 1769.6631.

Compound 45*: The donor tetrasaccharide 44* (20 mg, 0.0114 mmol) and the receptor 28* (12 mg, 0.0228 mmol) were dissolved in anhydrous $CH_2Cl_2$ (1.1 mL), and 4 Å molecular sieves and NIS (3 mg, 0.0137 mmol) were added. The reaction temperature was lowered to −15° C., and then TfOH (0.11 μL, 0.0011 mmol) was added dropwise under argon protection. The reaction was performed at −20° C. for 3 h. After it was detected by TLC that the reaction was complete, an appropriate amount of $Et_3N$ was added to quench the reaction. The solution was filtered, washed with a 10% $Na_2S_2O_3$ solution until the solution was colorless, then sequentially washed with saturated $NaHCO_3$ and a saturated saline solution, and dried with anhydrous Na$_2$SO$_4$. The solution was concentrated and purified by silica gel column chromatography (n-hexane/ethyl acetate: 6/1→4/1) to obtain the compound 45* (18 mg, 70%).

Compound 46*: The compound 30* (50 mg, 0.022 mmol) was dissolved in pyridine (1 mL), HF/pyridine (1 M, 0.22 mL) was added at 0° C., and then the reaction was performed under stirring at room temperature for 5 h. After it was detected by TLC that the reaction was complete, an appropriate amount of DCM was added for dissolution. Then the reaction solution was washed with saturated NaHCO$_3$ and a saturated saline solution, dried with anhydrous Na$_2$SO$_4$, filtered, concentrated, and separated and purified by column chromatography to obtain corresponding hemiacetal.

The hemiacetal obtained above was dissolved in CH$_2$Cl$_2$ (2 mL), CCl$_3$CN (16 μL, 0.11 mmol) and DBU (10 μL, 0.066 mmol) were added at 0° C., and the reaction was performed under stirring at room temperature for 2 h. After it was detected by TLC that the reaction was complete, the reaction solution was concentrated at 30° C., and then separated and purified by silica gel column chromatography (n-hexane/ethyl acetate: 5/1→3/1) to obtain the compound 46* (21 mg, 42%).

Figure 10:
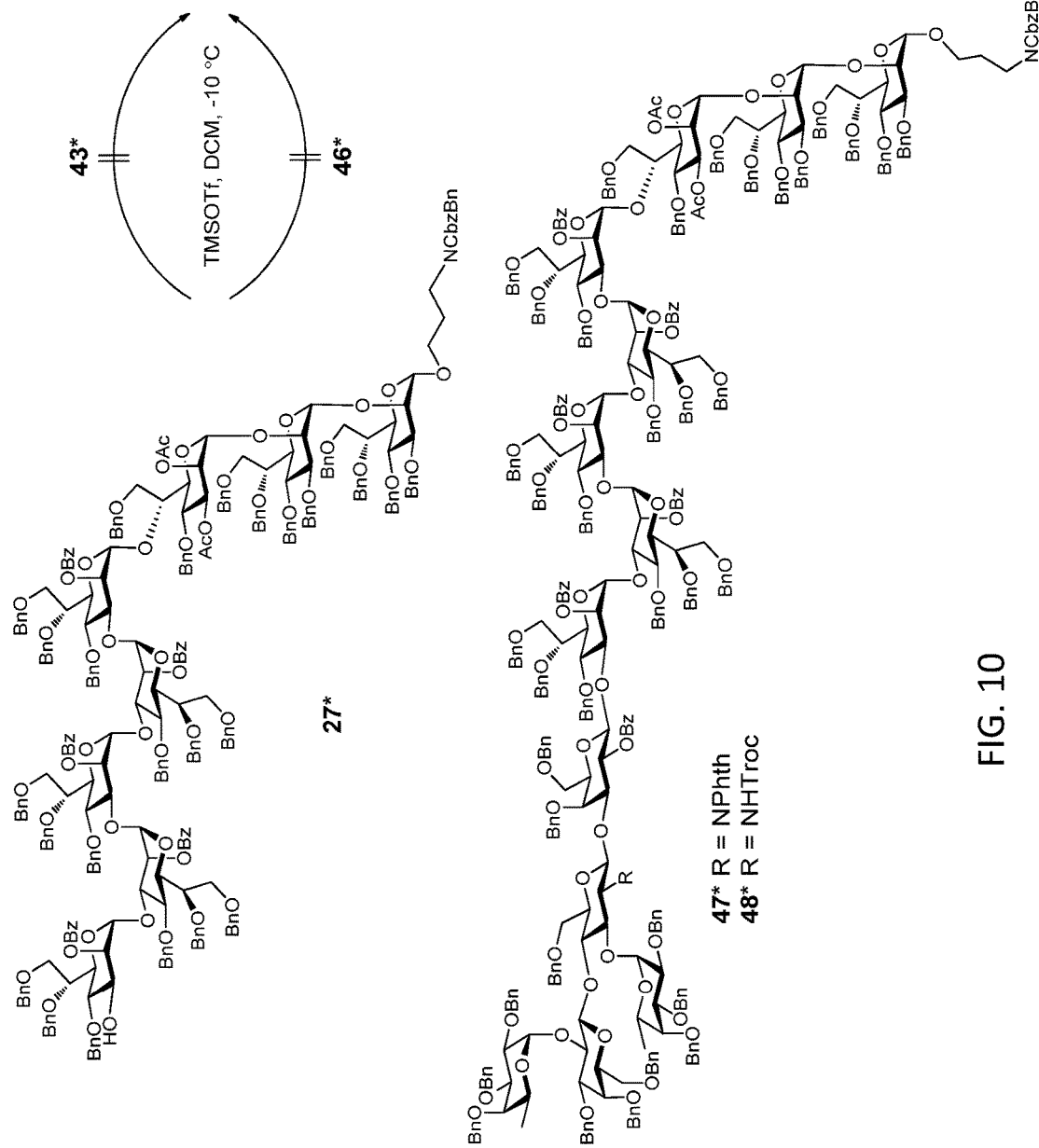
FIG. 10 is a reaction route diagram of a synthetic method [5+8] of the tridecasaccharide in Example 6.
Figure 11:
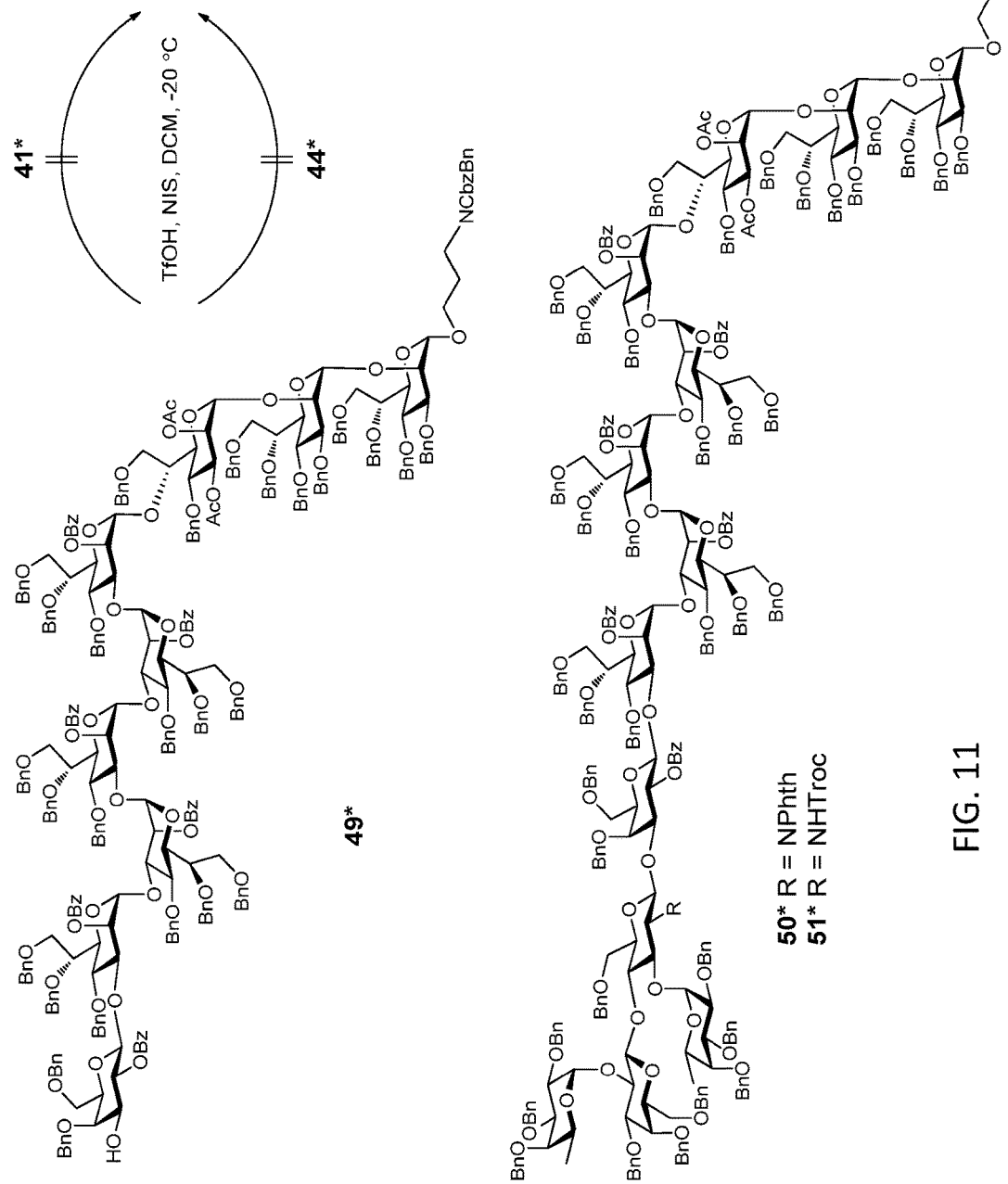
FIG. 11 is a reaction route diagram of a synthetic method [4+9] of the tridecasaccharide in Example 6.
Figure 12:
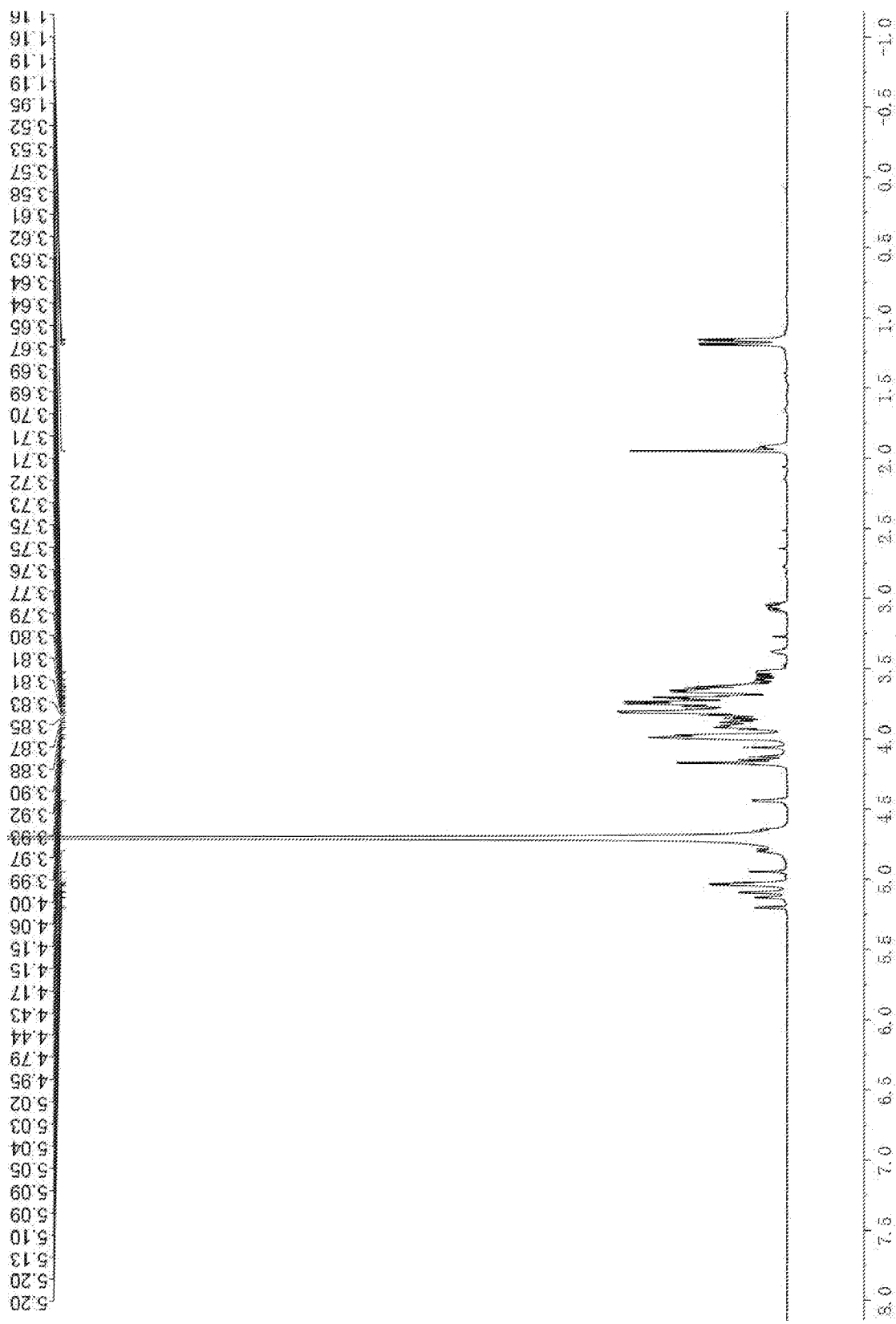
FIG. 12 is a $^1$H nuclear magnetic resonance (NMR) spectrogram of the O-antigen tridecasaccharide compound 36* of *Helicobacter pylori* serotype O:6.
Figure 13:
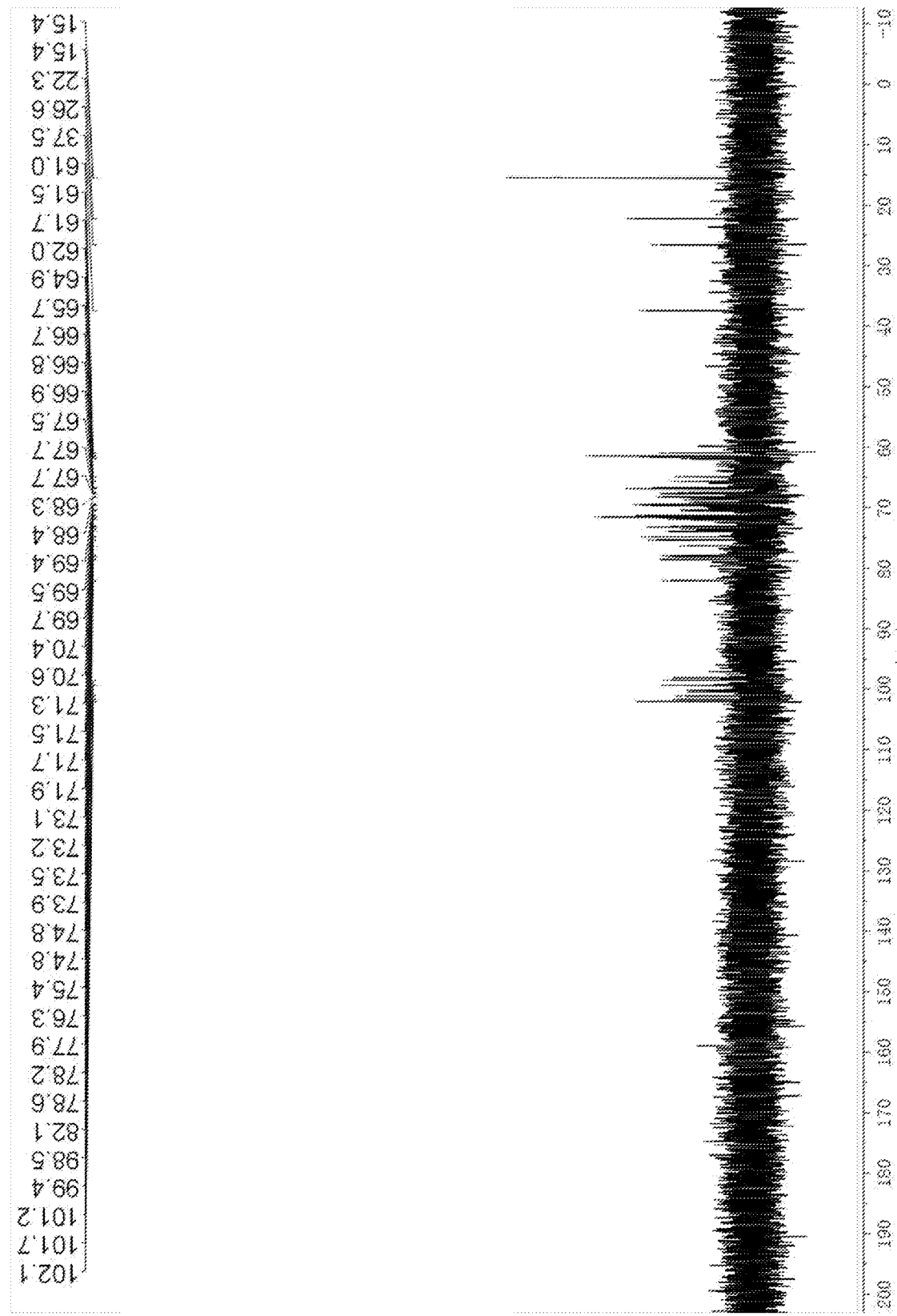
FIG. 13 is a carbon NMR spectrogram of the O-antigen tridecasaccharide compound 36* of *Helicobacter pylori* serotype O:6.
Figure 14:
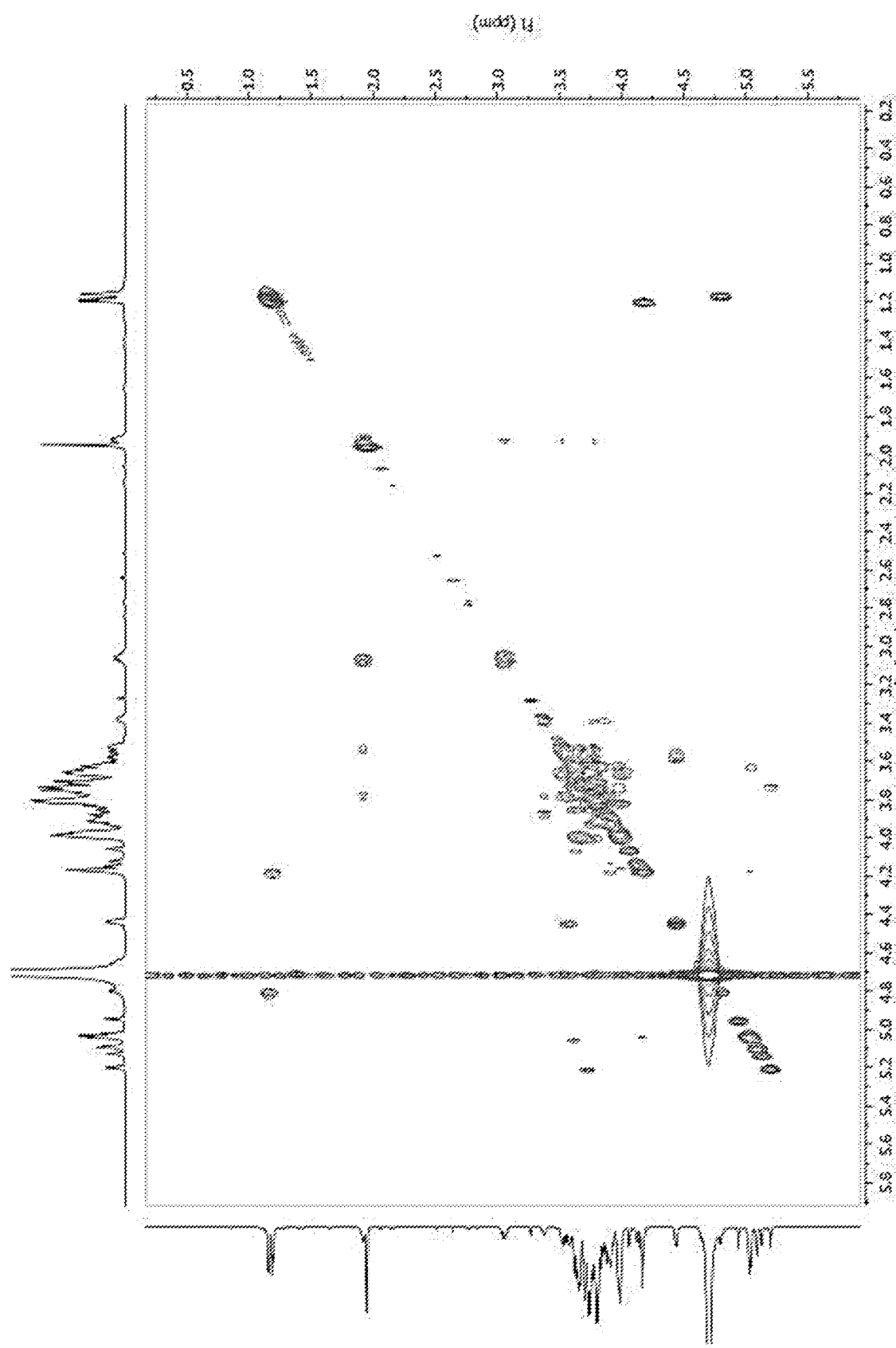
FIG. 14 is a hydrogen hydrogen correlation NMR spectrogram of the O-antigen tridecasaccharide compound 36* of *Helicobacter pylori* serotype O:6.
Figure 15:
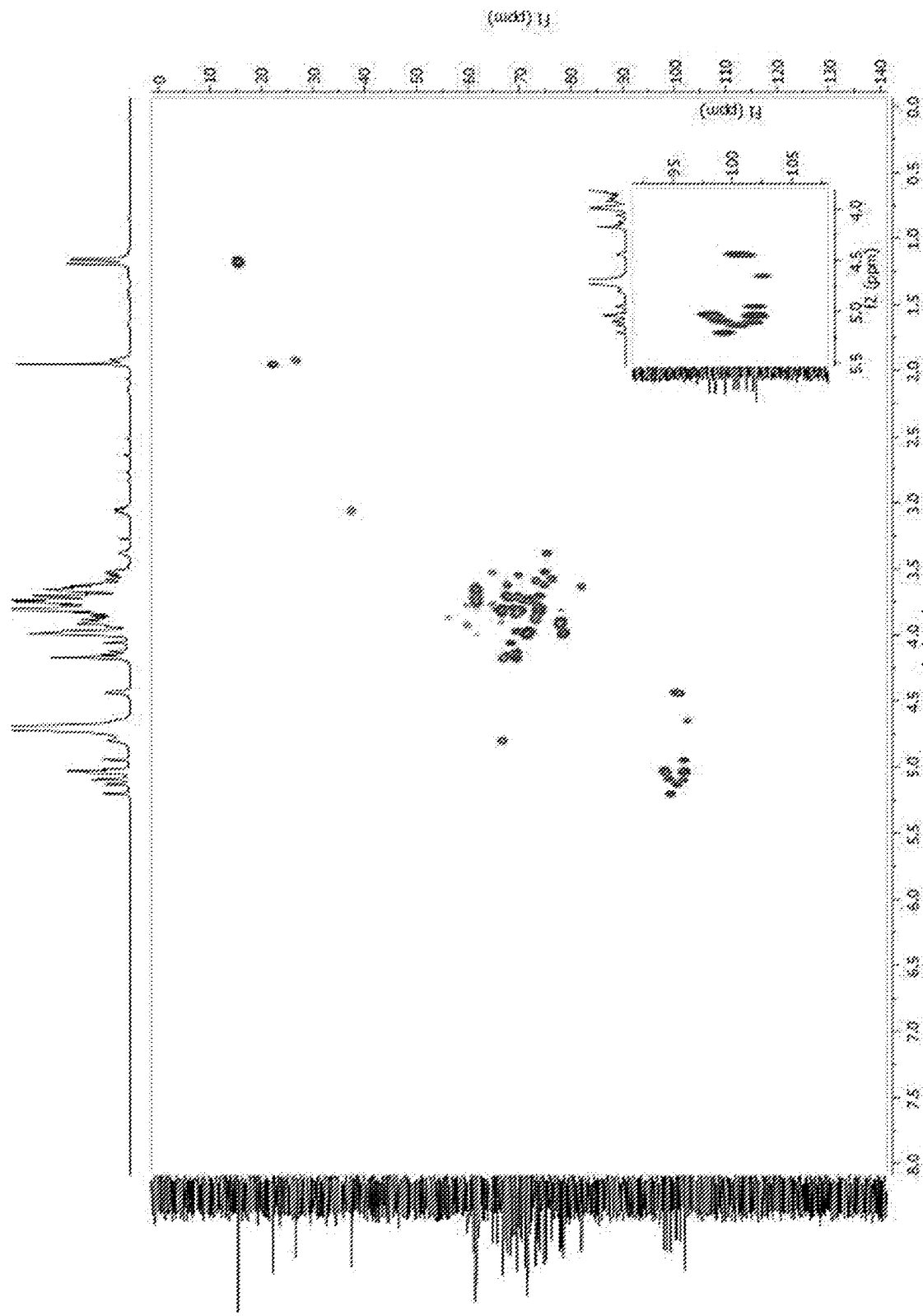
FIG. 15 is a carbon hydrogen correlation NMR spectrogram of the O-antigen tridecasaccharide compound 36* of *Helicobacter pylori* serotype O:6.

(2) Synthesis of Target Tridecasaccharide:

The synthetic routes are shown in FIGS. 10 and 11.

The implementation of the [5+8] synthesis strategy was carried out with 1.2 equivalent of glycosyl donor 43* or 46* and an octasaccharide receptor 27* under the action of an activating reagent TMSOTf. Unfortunately, the target molecule was not obtained, and the synthesis strategy [5+8] failed. Because considering that the reaction of the fully protected Le$^y$ tetrasaccharide with the galactose receptor 28* can be carried out successfully, the synthesis strategy of [4+9] was considered. 1.2 equivalent of glycosyl donor 41* or 44* reacted with the nonasaccharide receptor 49, the activating reagents were TfOH and NIS, and after the reaction was tried, the target molecule tridecasaccharide was still not obtained. Therefore, inferring the reasons for the failure of the above reaction strategy, the inventors have drawn two important conclusions: one is that the branched chain structure of the glycosylation donor increases the steric hindrance of the reaction, thereby leading to the failure of the reaction; and the second is the mismatch in activity between the glycosylation donor and the receptor, the donor activity is relatively high while the receptor activity is relatively low, thereby leading to the failure of the reaction. Therefore, the main solution strategy is to reduce the steric hindrance of the reaction and reduce the reactivity of the donor.

What is claimed is:

1. A process of the preparation of compound(28) of the following formula:

(28)

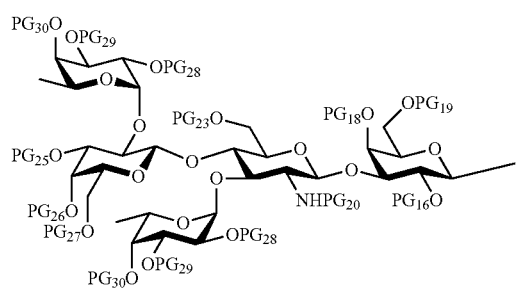

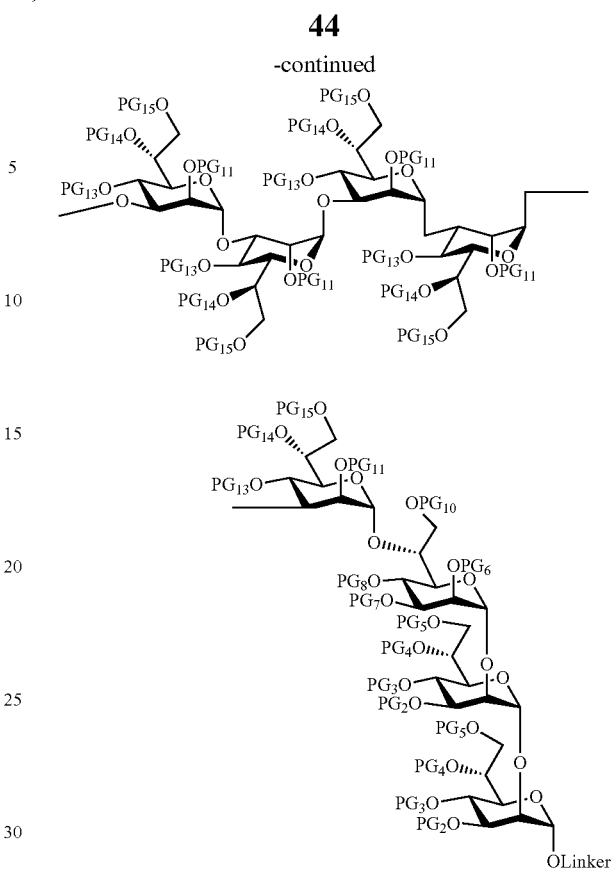

wherein PG$_1$, PG$_2$, PG$_3$, PG$_4$, PG$_5$, PG$_6$, PG$_7$ PG$_8$, PG$_9$, PG$_{10}$, PG$_{11}$, PG$_{12}$, PG$_{13}$a PG$_{14}$, PG$_{15}$, PG$_{18}$, PG$_{19}$, PG$_{21}$, PG$_{23}$, PG$_{25}$, PG$_{26}$, PG$_{27}$, PG$_{28}$, PG$_{29}$ and PG$_{30}$ are independently selected from the group consisting of hydrogen, acyl, 2-naphthylmethyl and its derivatives, benzyl and its derivatives, allyl and silyl; PG$_{16}$ and PG$_{24}$ are independently selected from the group consisting of hydrogen, alkoxycarbonyl and alkoxycarbonyl(acyl); PG$_{20}$ is selected from the group consisting of alkanoyl, diformyl, carbobenzyloxy(Cbz) and its derivatives; the leaving groups LG are independently selected from the group consisting of halogen, iminoester group, thio group and phosphonic acid group;

wherein the linker is an amino linker —(CH$_2$)$_n$—N—Y$_1$Y$_2$, wherein n=2-40, Y$_1$ is H or benzyl (Bn), and Y$_2$ is H or Cbz;

and said process comprising:

1) synthesizing a disaccharide compound (9) by coupling a compound (1) as a glycosyl donor and a compound (8) as a glycosyl receptor in an organic solvent following the synthetic route below:

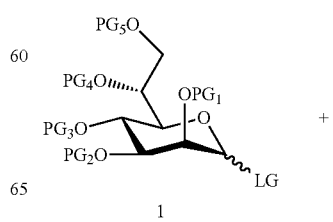

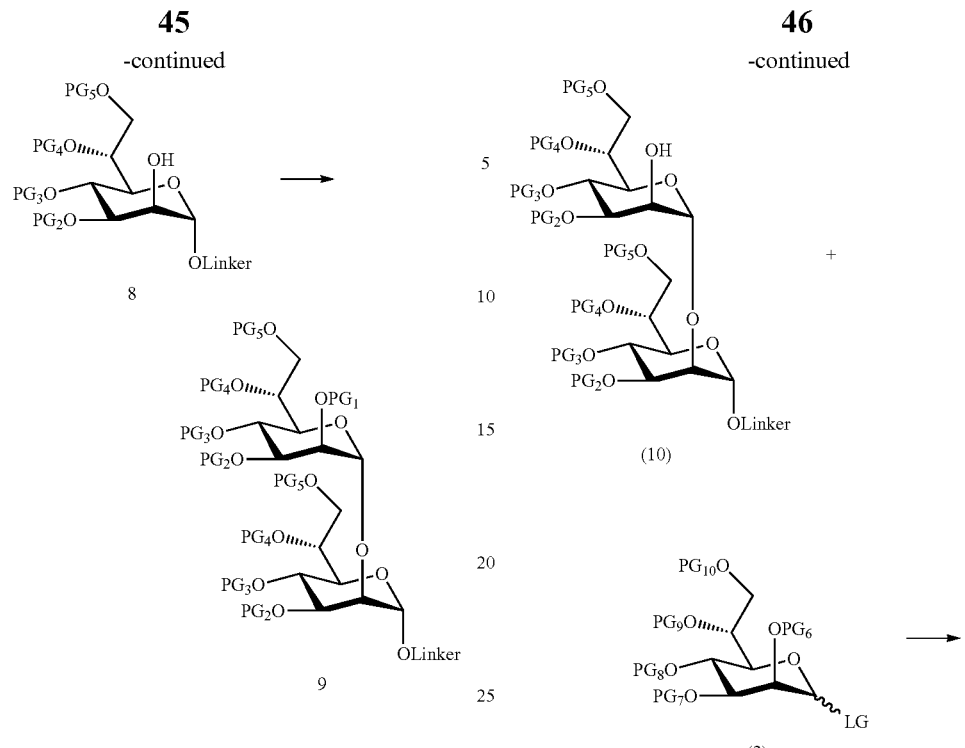

2) synthesizing a trisaccharide compound (11) by a deprotection reaction and a coupling reaction following the synthetic route below:

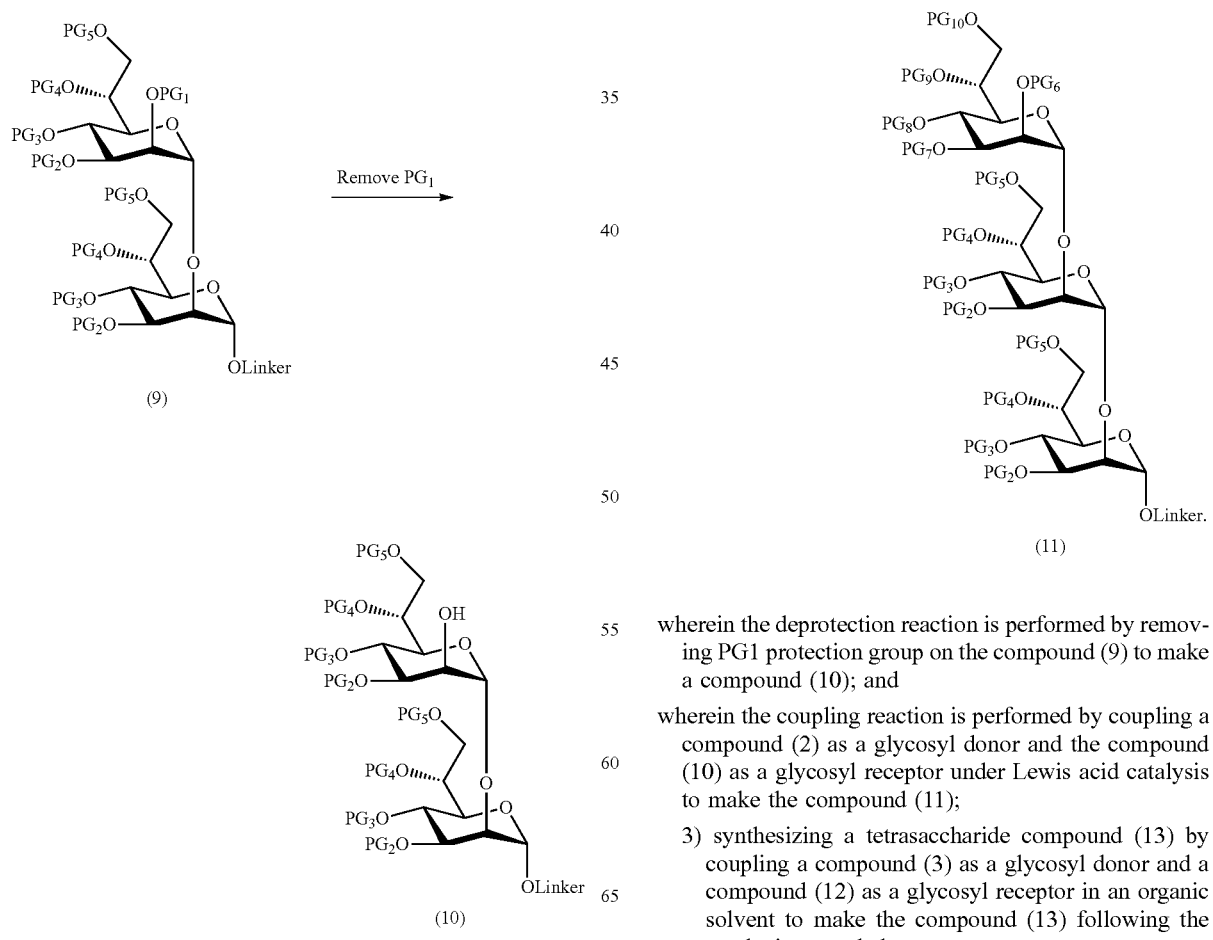

wherein the deprotection reaction is performed by removing PG1 protection group on the compound (9) to make a compound (10); and wherein the coupling reaction is performed by coupling a compound (2) as a glycosyl donor and the compound (10) as a glycosyl receptor under Lewis acid catalysis to make the compound (11);

3) synthesizing a tetrasaccharide compound (13) by coupling a compound (3) as a glycosyl donor and a compound (12) as a glycosyl receptor in an organic solvent to make the compound (13) following the synthetic route below:

4) synthesizing a pentasaccharide compound (16) by a first and a second coupling reactions following the synthetic route below:

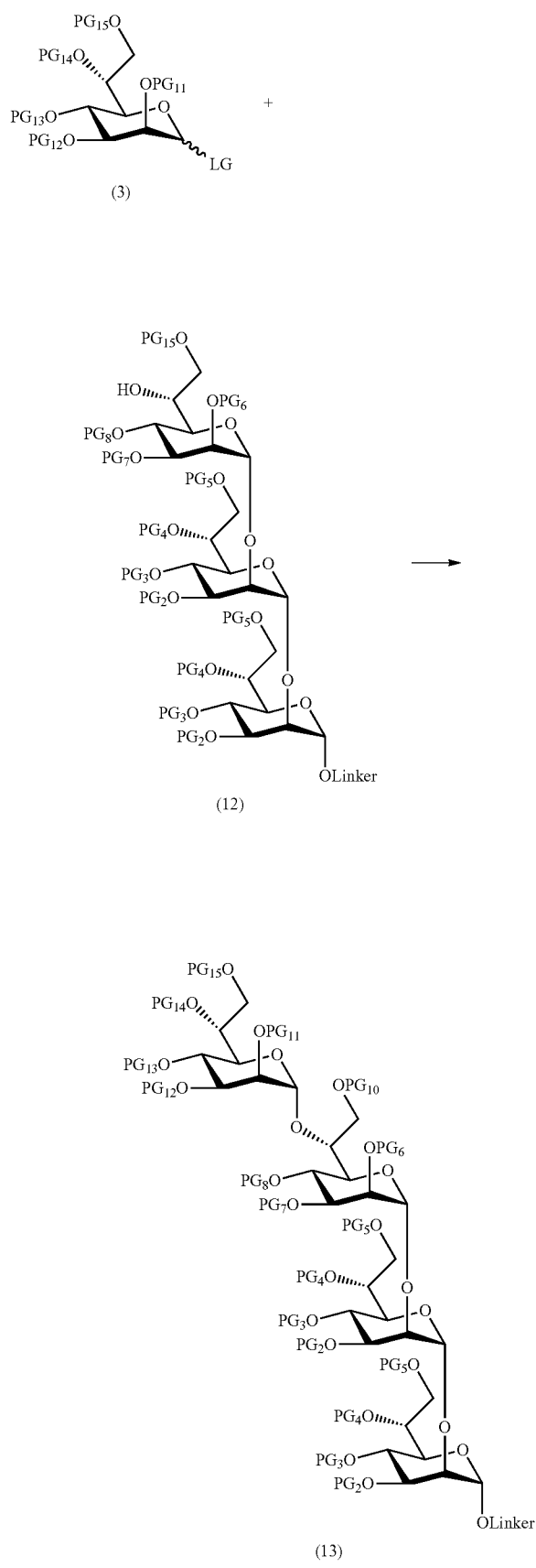

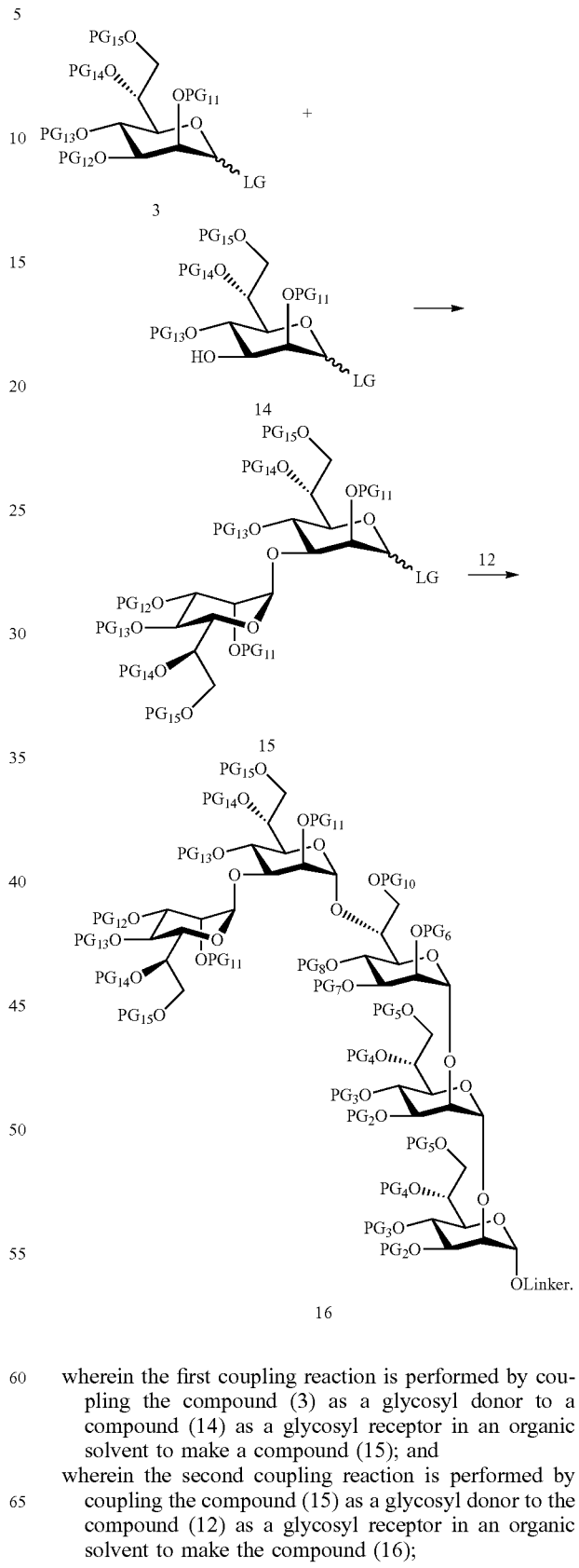

wherein the first coupling reaction is performed by coupling the compound (3) as a glycosyl donor to a compound (14) as a glycosyl receptor in an organic solvent to make a compound (15); and wherein the second coupling reaction is performed by coupling the compound (15) as a glycosyl donor to the compound (12) as a glycosyl receptor in an organic solvent to make the compound (16);

5) synthesizing an octasaccharide compound (20) by a third and a fourth coupling reactions following the synthetic route below:

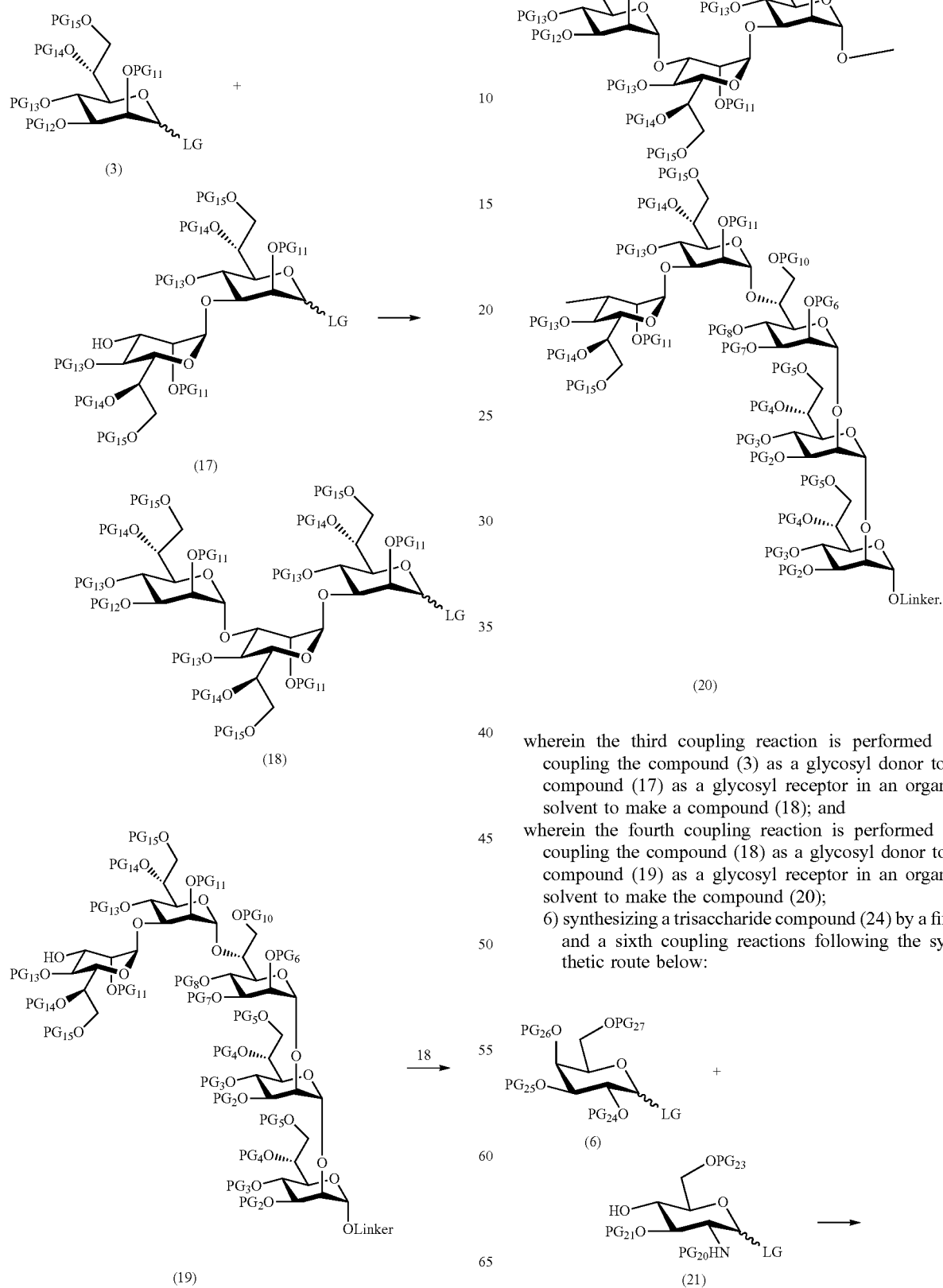

wherein the third coupling reaction is performed by coupling the compound (3) as a glycosyl donor to a compound (17) as a glycosyl receptor in an organic solvent to make a compound (18); and wherein the fourth coupling reaction is performed by coupling the compound (18) as a glycosyl donor to a compound (19) as a glycosyl receptor in an organic solvent to make the compound (20);

6) synthesizing a trisaccharide compound (24) by a fifth and a sixth coupling reactions following the synthetic route below:

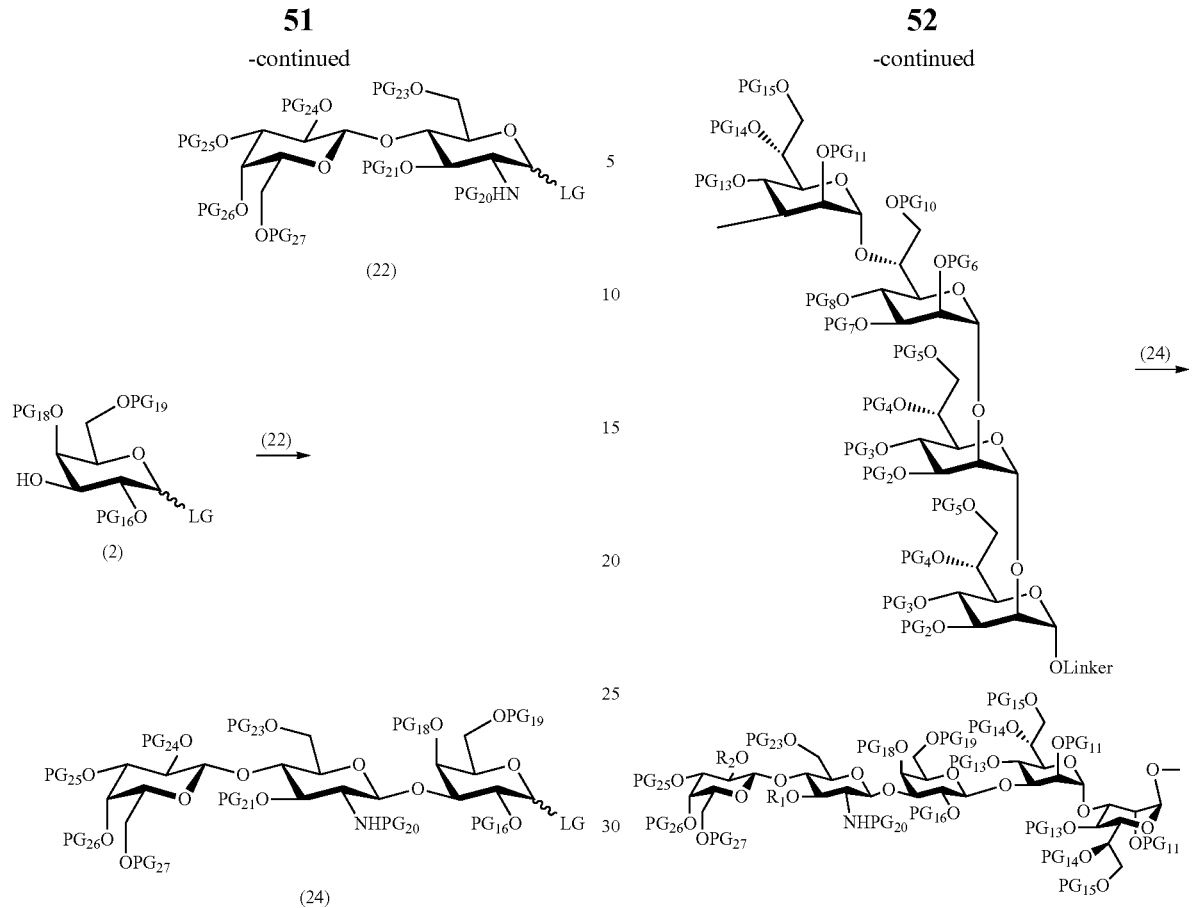

wherein the fifth coupling reaction is performed by coupling a compound (6) as a glycosyl donor to a compound (21) as a glycosyl receptor in an organic solvent to make a compound (22); and wherein the sixth coupling reaction is performed by coupling the compound (22) as a glycosyl donor to a compound (23) as a glycosyl receptor in an organic solvent to make the compound (24);

and 7) synthesizing the compound (28) following the synthetic route below:

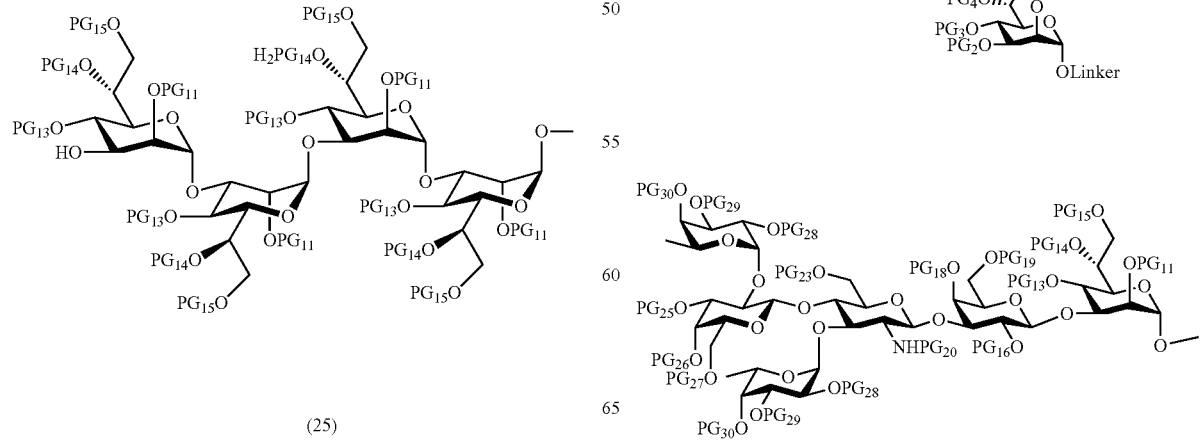

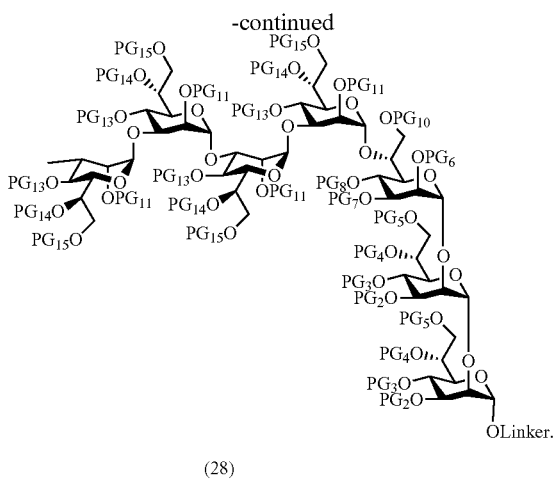

(28)

wherein the compound (24) as a glycosyl donor is coupled to a compound (25) as a glycosyl receptor under Lewis acid catalysis to obtain a compound (26);

wherein protection groups $PG_{21}$ and $PG_{24}$ are selectively removed from the compound (26) to obtain a compound (27); and wherein the compound (7) as a glycosyl donor is coupled to the compound (27) as a glycosyl receptor under Lewis acid catalysis to make the compound (28).

2. The method of claim 1, wherein the LG is selected from the group consisting of halogen, trichloroacetimidate, N-phenyl trifluoroacetimidate glycoside, ethylthio, phenylthio, p-tolylthio, and dibutylphosphonic acid group.

3. The method of claim 1, wherein the $PG_{20}$ is selected from the group consisting of trichloroacetyl, trichloroethoxycarbonyl, phthaloyl, and carbobenzyloxy.

4. The method of claim 1, wherein the $PG_{16}$ and $PG_{24}$ are selected from the group consisting of hydrogen, acetyl, benzoyl, pivaloyl, chloroacetyl, levulinyl, 9-fluorenylmethoxycarbonyl, and allyloxycarbonyl.

5. The method of claim 1, wherein the $PG_1$, $PG_9$, $PG_{12}$, $PG_{21}$, and $PG_{24}$ are independently selected from the group consisting of hydrogen, acetyl, benzoyl, pivaloyl, chloroacetyl (ClAc), levulinyl, 9-fluorenylmethoxycarbonyl, allyloxycarbonyl, 2-naphthylmethyl, p-methoxybenzyl and allyl.

6. The method of claim 3, wherein the $PG_1$, $PG_9$, $PG_{12}$, $PG_{21}$, and $PG_{24}$ are independently selected from the group consisting of hydrogen, acetyl, benzoyl, pivaloyl, chloroacetyl (ClAc), levulinyl, 9-fluorenylmethoxycarbonyl, allyloxycarbonyl, 2-naphthylmethyl, p-methoxybenzyl and allyl.

7. The method according to claim 1, wherein the $PG_2$, $PG_3$, $PG_4$, $PG_6$, $PG_7$, $PG_8$, $PG_{11}$, $PG_{13}$, $PG_{14}$, $PG_{18}$, $PG_{25}$, $PG_{26}$, $PG_{29}$ and $PG_{30}$ are independently selected from the group consisting of hydrogen, acetyl, benzoyl, pivaloyl, chloroacetyl, allyloxycarbonyl, benzyl, 2-naphthylmethyl, p-methoxybenzyl and allyl.

8. The method of claim 1, wherein the $PG_5$, $PG_{10}$, $PG_{15}$, $PG_{19}$, $PG_{23}$, $PG_{27}$ and $PG_{28}$ are selected from the group consisting of hydrogen, acetyl, benzoyl, pivaloyl, chloroacetyl, allyloxycarbonyl, benzyl, 2-naphthylmethyl, p-methoxybenzyl, allyl, tert-butyldimethylsilyl, tert-butyldiphenylsilyl and triethylsilyl.

9. The method of claim 7, wherein the $PG_5$, $PG_{10}$, $PG_{15}$, $PG_{19}$, $PG_{23}$, $PG_{27}$ and $PG_{28}$ are selected from the group consisting of hydrogen, acetyl, benzoyl, pivaloyl, chloroacetyl, allyloxycarbonyl, benzyl, 2-naphthylmethyl, p-methoxybenzyl, allyl, tert-butyldimethylsilyl, tert-butyldiphenylsilyl and triethylsilyl.

10. A method for preparing a reaction of synthesizing a saccharide-protein conjugate, comprising:

preparing a reaction to conjugate the compound (28) of claim 1 with a protein.

* * * * *